US009647220B2

(12) United States Patent
Yoshinaga et al.

(10) Patent No.: US 9,647,220 B2
(45) Date of Patent: May 9, 2017

(54) ORGANIC MULTICOLOR LIGHT-EMITTING APPARATUS

(71) Applicant: Sony Corporation, Minato-ku, Tokyo (JP)

(72) Inventors: Tadahiko Yoshinaga, Tokyo (JP); Mitsuru Eida, Sodegaura (JP); Hironori Kawakami, Sodegaura (JP)

(73) Assignees: SONY CORPORATION, Tokyo (JP); IDEMITSU KOSAN CO., LTD., Tokyo (JP)

( * ) Notice: Subject to any disclaimer, the term of this patent is extended or adjusted under 35 U.S.C. 154(b) by 27 days.

(21) Appl. No.: 14/442,652

(22) PCT Filed: Nov. 8, 2013

(86) PCT No.: PCT/JP2013/006598
§ 371 (c)(1),
(2) Date: May 13, 2015

(87) PCT Pub. No.: WO2014/076917
PCT Pub. Date: May 22, 2014

(65) Prior Publication Data
US 2016/0276602 A1  Sep. 22, 2016

(30) Foreign Application Priority Data
Nov. 15, 2012  (JP) ................. 2012-251600

(51) Int. Cl.
*H01L 51/00* (2006.01)
*C07D 487/04* (2006.01)
(Continued)

(52) U.S. Cl.
CPC ........ *H01L 51/0073* (2013.01); *C07D 487/04* (2013.01); *C07D 491/048* (2013.01);
(Continued)

(58) Field of Classification Search
CPC ........ H01L 51/0071–51/0073; H01L 51/0052; H01L 51/0054; H01L 51/0058;
(Continued)

(56) References Cited

U.S. PATENT DOCUMENTS 8,318,323 B2  11/2012  Kato et al.
9,024,521 B2  5/2015  Yoshinaga et al.
(Continued)

FOREIGN PATENT DOCUMENTS

JP  10-153967 A  6/1998
JP  2011-233855 A  11/2011
(Continued)

OTHER PUBLICATIONS

T. Higo et al., "A High-Performance Hybrid OLED Device Assisted by Evaporated Common Organic Layers", OLED2-2, Proceedings of the 17th International Display Workshops, vol. 1 (Dec. 1, 2010).
(Continued)

*Primary Examiner* — Sheng Zhu
(74) *Attorney, Agent, or Firm* — Foley & Lardner LLP

(57) ABSTRACT

An organic electroluminescence multicolor light-emitting apparatus including:
a substrate; and a first light-emitting device and a second light-emitting device being arranged in parallel relative to the surface of the substrate; wherein the first light-emitting device includes, between an anode and a cathode, a first organic layer, a second organic layer and a third organic layer in this sequence from the anode side in a direction perpendicular to the surface of the substrate,
the second light-emitting device includes, between an anode and a cathode, a second organic layer and a third organic layer in this sequence from the anode side in a direction perpendicular to the surface of the substrate, the first
(Continued)

organic layer includes a first emitting dopant, the third organic layer includes a second emitting dopant, and the second organic layers independently comprise any one of compounds represented by the following formulas (1) to (6).

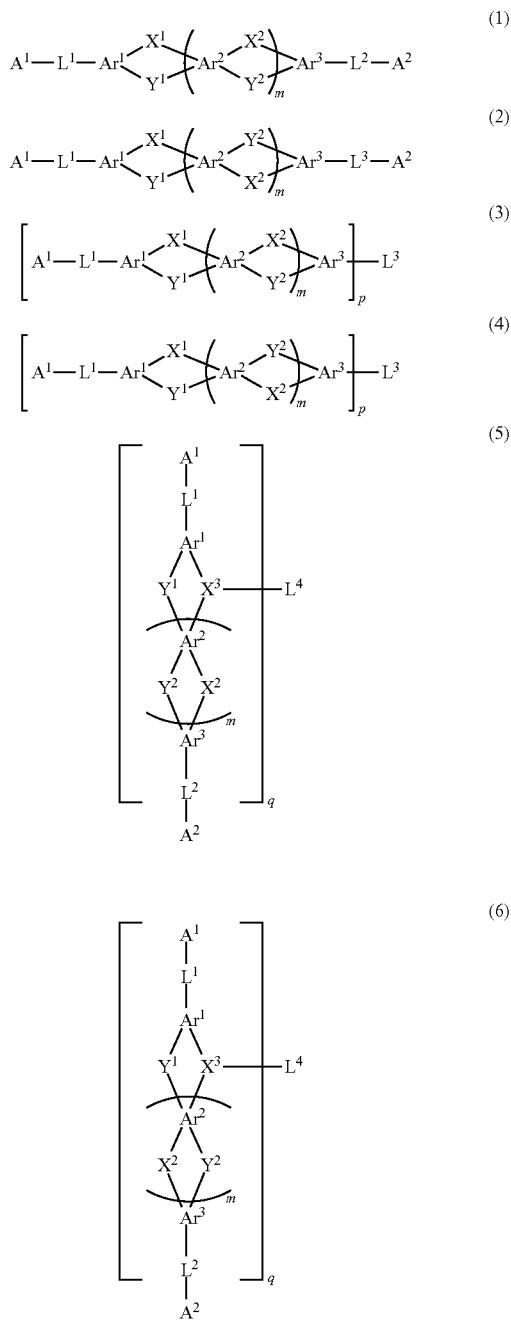

23 Claims, 2 Drawing Sheets

(51) Int. Cl.
    C07D 491/048    (2006.01)
    C07D 493/04     (2006.01)
    C09K 11/06      (2006.01)
    H01L 51/50      (2006.01)
    H01L 27/32      (2006.01)

(52) U.S. Cl.
    CPC ............ *C07D 493/04* (2013.01); *C09K 11/06* (2013.01); *H01L 51/006* (2013.01); *H01L 51/0052* (2013.01); *H01L 51/0054* (2013.01); *H01L 51/0058* (2013.01); *H01L 51/0059* (2013.01); *H01L 51/0061* (2013.01); *H01L 51/0067* (2013.01); *H01L 51/0071* (2013.01); *H01L 51/0072* (2013.01); *H01L 51/0074* (2013.01); *H01L 51/0085* (2013.01); *C09K 2211/1007* (2013.01); *C09K 2211/1029* (2013.01); *C09K 2211/185* (2013.01); *H01L 27/3211* (2013.01); *H01L 51/504* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 2251/558* (2013.01)

(58) Field of Classification Search
    CPC ............... H01L 51/006; H01L 51/0061; H01L 51/0067; H01L 51/0085; H01L 51/5056; H01L 2251/558
    USPC .............................................. 257/40; 313/504
    See application file for complete search history.

(56) References Cited

U.S. PATENT DOCUMENTS

| | | | |
|---|---|---|---|
| 2001/0001050 A1 | 5/2001 | Miyashita et al. | |
| 2002/0041926 A1 | 4/2002 | Miyashita et al. | |
| 2002/0136823 A1 | 9/2002 | Miyashita et al. | |
| 2002/0155215 A1 | 10/2002 | Miyashita et al. | |
| 2003/0054186 A1 | 3/2003 | Miyashita et al. | |
| 2005/0042477 A1 | 2/2005 | Miyashita et al. | |
| 2010/0012931 A1 | 1/2010 | Kato et al. | |
| 2010/0120185 A1 | 5/2010 | Miyashita et al. | |
| 2011/0248247 A1 | 10/2011 | Matsumoto et al. | |
| 2012/0223633 A1* | 9/2012 | Yoshinaga et al. | ........... 313/504 |
| 2013/0092915 A1 | 4/2013 | Matsumoto et al. | |
| 2013/0187138 A1 | 7/2013 | Matsumoto et al. | |
| 2014/0159023 A1 | 6/2014 | Matsumoto et al. | |

FOREIGN PATENT DOCUMENTS

| | | |
|---|---|---|
| JP | 2012-140365 A | 7/2012 |
| JP | 2012-186021 A | 9/2012 |
| WO | WO 2009/148015 A1 | 12/2009 |
| WO | WO 2009/148016 A1 | 12/2009 |
| WO | WO 2009/148062 A1 | 12/2009 |
| WO | WO 2012/157211 A1 | 11/2012 |

OTHER PUBLICATIONS

Translation of the International Preliminary Report on Patentability dated May 28, 2015 and the Written Opinion dated Feb. 10, 2014 corresponding to PCT/JP2013/006598.

* cited by examiner

ORGANIC MULTICOLOR LIGHT-EMITTING APPARATUS

TECHNICAL FIELD

The invention relates to an organic EL multicolor light-emitting apparatus.

BACKGROUND ART

An organic electroluminescence (EL) device has many attractive features as a display (multicolor light-emitting apparatus) such as low consumption power, small thickness, high-response speed, wide viewing angle or the like. As for an organic EL display using such an organic EL device, an all-deposition type display in which an emitting layer or the like are formed by depositing a low-molecular weight organic material has been put into practical use in a small-sized display such as a mobile phone.

In an all-deposition type organic EL display, materials are not used efficiently. In addition, a vacuum system or a color-coding mask for a deposition layer is required for production, and hence, film formation for a large-sized screen is difficult, whereby it has problems regarding a reduction in cost and an increase in size.

On the other hand, if a coating-type organic EL display in which an emitting layer or the like are formed by coating a high-molecular organic material by ink-jetting, nozzle printing, gravure printing or the like can be realized, there is a possibility that the problems associated with a deposition method as mentioned above can be solved (a display in FIG. 2, for example, HIL: hole-injecting layer, IL: interlayer (hole-transporting layer), LEP: high-molecular light-emitting polymer, ETL: electron-transporting layer). However, a coating-type organic EL display has an insufficient luminous efficiency and a shorter lifetime as compared with an all-deposition type display. In particular, it has a serious problem in blue emission.

Patent Document 1 discloses a hybrid-type organic EL display which is a combination of a coating-type display which is inexpensive and enables the screen size to be increased and a high-performance deposition type display (FIG. 3).

The organic EL display shown in FIG. 3 is an organic EL display obtained by a method in which a red-emitting layer and a green-emitting layer (LEP) are separately provided by a coating method, and a blue-emitting layer is allowed to be a common layer (Blue Common layer) by depositing a low-molecular material. The display shown in FIG. 3 can enhance the blue emission performance, and it is possible to reduce color-coding steps from 3 to 2 steps. However, since a coating type hole-transporting layer (IL) is in contact with the anode of the blue-emitting layer, emission performance of blue color was not sufficient.

The display shown in FIG. 4 which is disclosed in Non-Patent Document 1, Patent Document 2 or Patent Document 3 exhibits a significant improvement in blue emission performance due to the provision of a hybrid connecting layer (HCL) between the blue common layer as a deposition layer and a coating layer.

As the material of HCL, in order to improve the blue emission performance, not only matching between the hole-injecting and transporting properties and the blue-emitting layer, electron-injecting and transporting properties to a red-emitting layer and a green or yellow-emitting layer formed by coating are required; in particular, when a red-emitting layer and a green or yellow-emitting layer formed by coating are phosphorescent emitting layers, a higher triplet energy (T1) is also required in order to prevent diffusion of triplet energy. As the material for HCL, when a common hole-transporting material, a common electron-transporting material or a common high T1 material are independently used singly, there is a problem that comprehensive improvement in performance or color reproducibility, in particular, suppression of change in chromaticity by current of an organic EL multicolor light-emitting apparatus cannot be attained satisfactorily. That is, due to diffusion of triplet energy from the red, green or yellow-emitting layer when an organic EL multicolor light-emitting apparatus is driven (i.e. when driving current is changed), the blue common layer emits light, and as a result, blue emission is mixed with red, green or yellow emission, whereby color mixing occurs.

RELATED ART DOCUMENTS

Patent Documents

Patent Document 1: JP-A-H10-153967
Patent Document 2: JP-A-2011-233855
Patent Document 3: JP-A-2012-186021

Non-Patent Document

Non-Patent Document 1: IDW2010 Digest, P311

SUMMARY OF THE INVENTION

An object of the invention is to provide an organic EL multicolor light-emitting apparatus which has a high luminous efficiency, a long life and a high quality.

As a result of intensive studies, the inventors have found that, by providing a layer (second organic layer) formed of a prescribed material that can function as an electron-transporting layer or a triplet blocking layer for a red and yellow phosphorescent light-emitting device or a green phosphorescent light-emitting device and can function as a hole-injecting and transporting layer for a blue fluorescent emitting device, a highly efficient, long-lived and high-quality organic EL multicolor light-emitting apparatus can be obtained.

According to the invention, the following organic multicolor light-emitting apparatus is provided.

1. An organic electroluminescence multicolor light-emitting apparatus comprising:
    a substrate; and
    a first light-emitting device and a second light-emitting device being arranged in parallel on the surface of the substrate;
    wherein the first light-emitting device comprises, between an anode and a cathode, a first organic layer, a second organic layer and a third organic layer in this sequence from the anode side in a direction perpendicular to the surface of the substrate,
    the second light-emitting device comprises, between an anode and a cathode, a second organic layer and a third organic layer in this sequence from the anode side in a direction perpendicular to the surface of the substrate,
    the first organic layer comprises a first emitting dopant,
    the third organic layers comprise a second emitting dopant, and
    the second organic layers independently comprise any one of compounds represented by the following formulas (1) to (6):

(1)

(2)

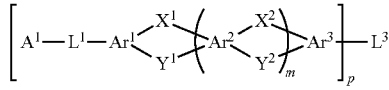
(3)

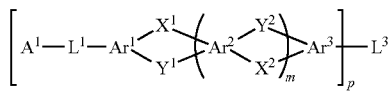
(4)

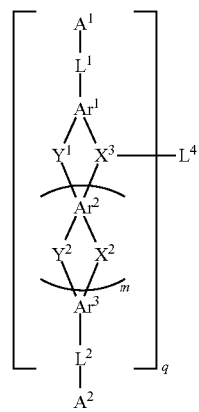
(5)

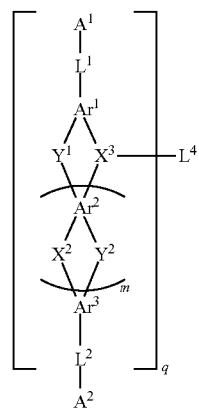
(6)

wherein in the formulas (1) to (6), $Ar^1$, $Ar^2$ and $Ar^3$ are independently a substituted or unsubstituted aromatic hydrocarbon group including 6 ring carbon atoms or a substituted or unsubstituted aromatic heterocyclic group including 6 ring atoms;

in the formulas (1) to (4), $X^1$ and $X^2$ are independently oxygen (O), sulfur (S), $>N—R^1$, $>CR^2R^3$, $>BR^4$, $>SiR^5R^6$, $>C=NR^7$, $>C=CR^8R^9$, $>S=O$, $>SO_2$, $>PR^{10}$ or $>P(=O)R^{11}$; and $Y^1$ and $Y^2$ are independently a single bond, oxygen (O), sulfur (S), $>N—R^1$, $>CR^2R^3$, $>BR^4$, $>SiR^5R^6$, $>C=NR^7$, $>C=CR^8R^9$, $>S=O$, $>SO_2$, $>PR^{10}$ or $>P(=O)R^{11}$;

in the formulas (5) and (6), $X^3$ is nitrogen (N), $>CR^2$, (boron) B, $>SiR^5$, phosphorus (P) or $>P=O$; $X^2$ is oxygen (O), sulfur (S), $>N—R^1$, $>CR^2R^3$, $>BR^4$, $>SiR^5R^6$, $>C=NR^7$, $>C=CR^8R^9$, $>S=O$, $>SO_2$, $>PR^{10}$ or $>P(=O)$ $R^{11}$; and $Y^1$ and $Y^2$ are independently a single bond, oxygen (O), sulfur (S), $>N—R^1$, $>CR^2R^3$, $>BR^4$, $>SiR^5R^6$, $>C=NR^7$, $>C=CR^8R^9$, $>S=O$, $>SO_2$, $>PR^{10}$ or $>P(=O)$ $R^{11}$;

$R^1$ to $R^{11}$ are independently a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms;

m is an integer of 0 to 3; and p and q are independently an integer of 2 to 4;

in the formulas (1), (2), (5) and (6), $L^1$ and $L^2$ are independently a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (3) and (4), $L^1$ is a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (3) and (4), $L^3$ is, when p is 2, a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (5) and (6), $L^4$ is, when q is 2, a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (3) and (4), $L^3$ is, when p is 3, a substituted or unsubstituted trivalent saturated hydrocarbon group including 1 to 20 carbon atoms, a substituted or unsubstituted trivalent cyclic saturated hydrocarbon group including 3 to 20 carbon atoms, a trivalent silyl group or a trivalent substituted silyl group including 3 to 20 carbon atoms, a substituted or unsubstituted trivalent aromatic hydrocarbon group including 6 to 30 ring carbon atoms or a substituted or unsubstituted trivalent aromatic heterocyclic group including 5 to 30 ring atoms;

in the formulas (5) and (6), $L^4$ is, when q is 3, a substituted or unsubstituted trivalent saturated hydrocarbon group including 1 to 20 carbon atoms, a substituted or unsubstituted trivalent cyclic saturated hydrocarbon group including 3 to 20 carbon atoms, a trivalent silyl group or a trivalent substituted silyl group including 3 to 20 carbon atoms, a substituted or unsubstituted trivalent aromatic hydrocarbon group including 6 to 30 ring carbon atoms or a substituted or unsubstituted trivalent aromatic heterocyclic group including 5 to 30 ring atoms;

in the formulas (3) and (4), $L^3$ is, when p is 4, a substituted or unsubstituted tetravalent saturated hydrocarbon group including 1 to 20 carbon atoms, a substituted or unsubstituted tetravalent cyclic saturated hydrocarbon group including 3 to 20 carbon atoms, a tetravalent silyl group or a substituted tetravalent silyl group including 3 to 20 carbon atoms, a substituted or unsubstituted tetravalent aromatic hydrocarbon group including 6 to 30 ring carbon atoms or a substituted or unsubstituted tetravalent aromatic heterocyclic group including 5 to 30 ring atoms;

in the formulas (5) and (6), $L^4$ is, when q is 4, a substituted or unsubstituted tetravalent saturated hydrocarbon group including 1 to 20 carbon atoms, a substituted or unsubstituted tetravalent cyclic saturated hydrocarbon group including 3 to 20 carbon atoms, a tetravalent silyl group or a substituted tetravalent silyl group including 3 to 20 carbon atoms, a substituted or unsubstituted tetravalent aromatic hydrocarbon group including 6 to 30 ring carbon atoms or a substituted or unsubstituted tetravalent aromatic heterocyclic group including 5 to 30 ring atoms;

in the formulas (1), (2), (5) and (6), $A^1$ and $A^2$ are independently a hydrogen atom, a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms;

in the formulas (3) and (4), $A^1$ is a hydrogen atom, a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms, or a substituted or unsubstituted aromatic heterocyclic group including 5 to 30 ring atoms;

provided that, when both $X^1$ and $X^2$ are >N—$R^1$, when both $Y^1$ and $Y^2$ are >N—$R^1$, or when $X^2$ is >N—$R^1$ and $X^3$ is nitrogen (N), $L^4$ or at least one of $R^1$ is selected from a group including a furan skeleton, a group including a thiophene skeleton, and a group including a fused aromatic hydrocarbon skeleton including 14 to 30 ring carbon atoms.

2. The organic electroluminescence multicolor light-emitting apparatus according to 1, wherein m of the compound represented by the formulas (1) to (6) is 1 and $Y^1$ and $Y^2$ are a single bond.

3. The organic electroluminescence multicolor light-emitting apparatus according to 1 or 2, wherein the compound represented by the formula (1) or (2) is a compound represented by the following formulas (7) to (12):

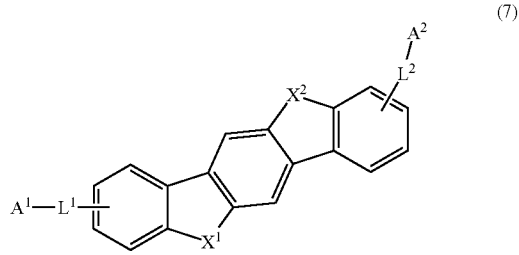

(7)

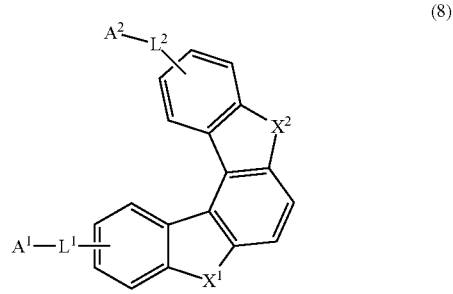

(8)

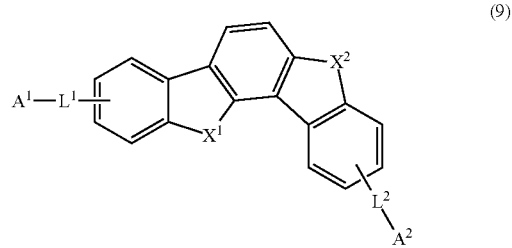

(9)

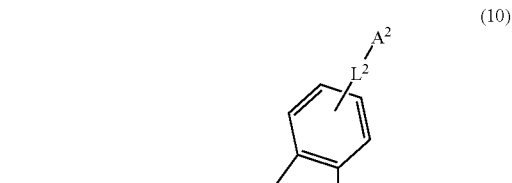

(10)

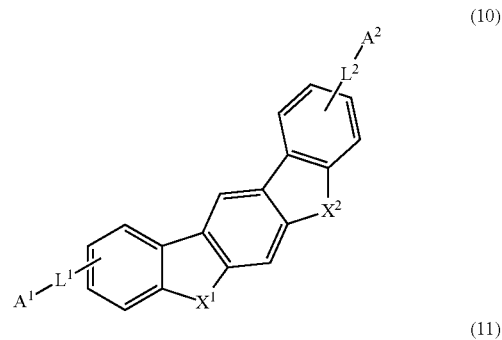

(11)

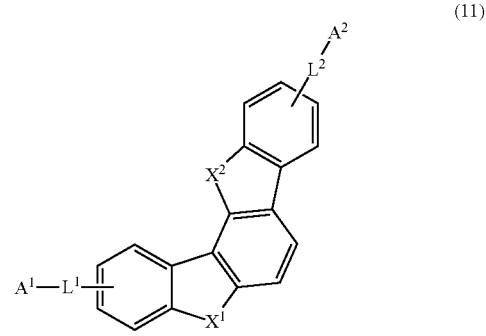

(12)

wherein $A^1$, $A^2$, $L^1$, $L^2$, $X^1$ and $X^2$ are independently the same as $A^1$, $A^2$, $L^1$, $L^2$, $X^1$ and $X^2$ in the formula (1).

4. The organic electroluminescence multicolor light-emitting apparatus according to 1 or 2, wherein the compound represented by the formula (3) or (4) is a compound represented by the following formulas (13) to (18):

represented by the formula (5) or (6) is a compound represented by the following formulas (19) to (24):

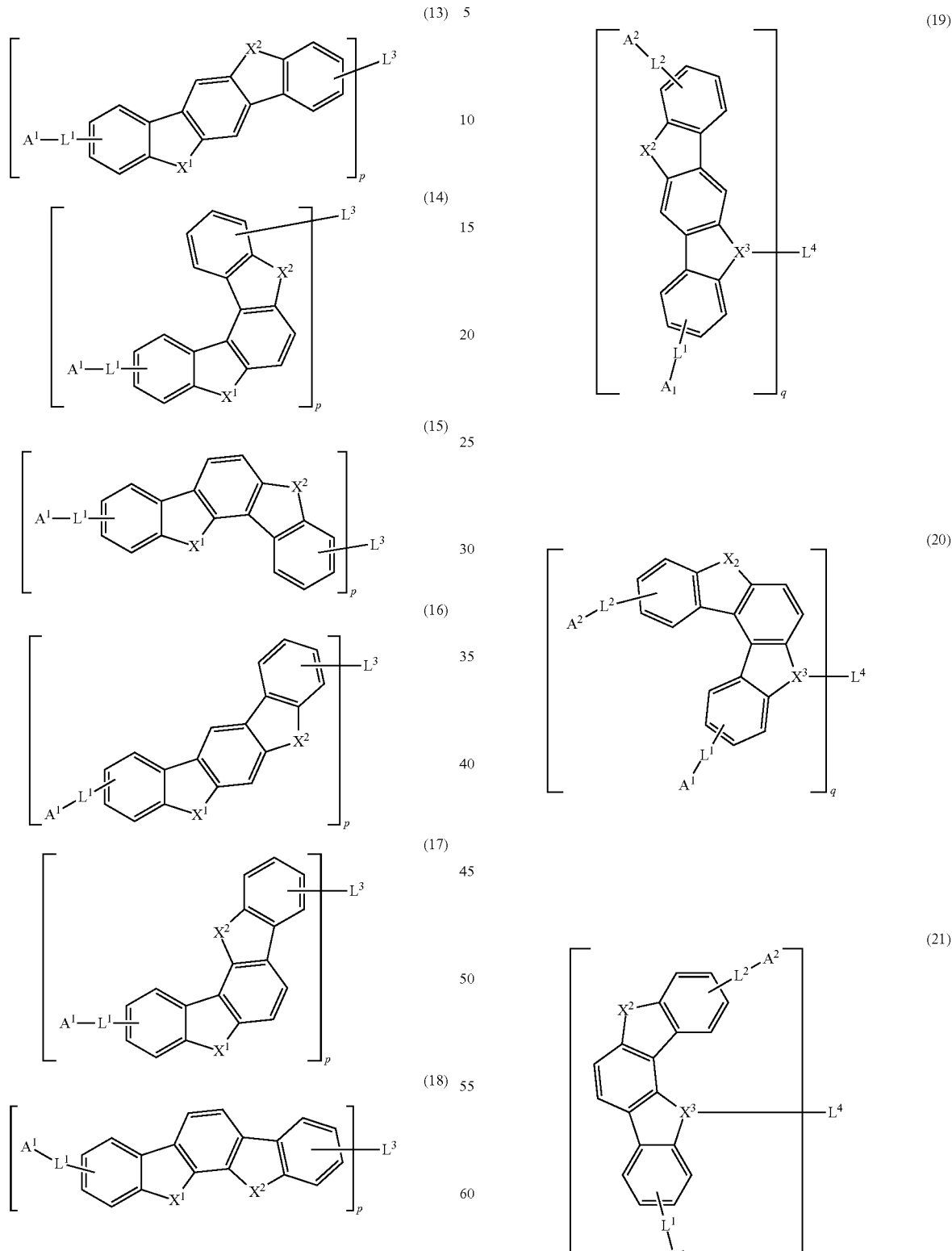

wherein $A^1$, $L^1$, $L^3$, $X^1$, $X^2$ and p are independently the same as $A^1$, $L^1$, $L^3$, $X^1$, $X^2$ and p in the formula (3).

5. The organic electroluminescence multicolor light-emitting apparatus according to 1 or 2, wherein the compound -continued

(22)
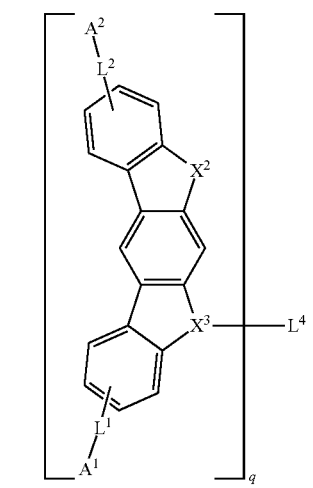

(23)
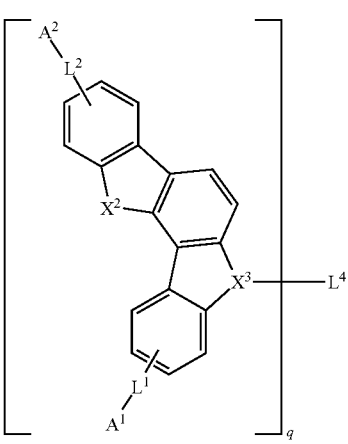

(24)
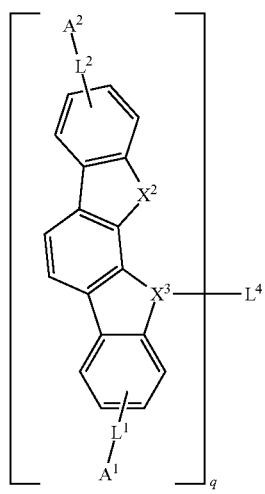

wherein $A^1$, $A^2$, $L^1$, $L^2$, $L^4$, $X^2$, $X^3$ and q are independently the same as $A^1$, $A^2$, $L^1$, $L^2$, $L^4$, $X^2$, $X^3$ and q in the formula (5).

6. The organic electroluminescence multicolor light-emitting apparatus according to any one of 1 to 5, wherein $X^1$ or $X^2$ is an element or a group selected from oxygen (O), sulfur (S) and >N—$R^1$ (wherein $R^1$ is the same as $R^1$ in the formulas (1) to (6)).

7. The organic electroluminescence multicolor light-emitting apparatus according to 6, wherein $X^1$ or $X^2$ is oxygen (O).

8. The organic electroluminescence multicolor light-emitting apparatus according to 6, wherein $R^1$ in the >N—$R^1$ is a group including a fused aromatic hydrocarbon skeleton including 10 to 30 ring carbon atoms or a group including an aromatic heterocyclic skeleton including 9 to 30 ring atoms.

9. The organic electroluminescence multicolor light-emitting apparatus according to any one of 1 to 6, wherein $X^3$ is nitrogen (N).

10. The organic electroluminescence multicolor light-emitting apparatus according to any one of 1 to 9, wherein p and q are 2.

11. The organic electroluminescence multicolor light-emitting apparatus according to 1, wherein m is 0, and at least one of $A^1$ and $A^2$ in the formula (1) or (2) is a group including a fused aromatic hydrocarbon skeleton including 10 to 30 ring carbon atoms or a group including an aromatic heterocyclic skeleton including 9 to 30 ring atoms.

12. The organic electroluminescence multicolor light-emitting apparatus according to 1, wherein m is 0 and $L^4$ in the formula (5) or (6) is a group including a fused aromatic hydrocarbon skeleton including 10 to 30 ring carbon atoms or a group including an aromatic heterocyclic skeleton including 9 to 30 ring atoms.

13. The organic electroluminescence multicolor light-emitting apparatus according to 11 or 12, wherein $Y^1$ and $Y^2$ are a single bond.

14. The organic electroluminescence multicolor light-emitting apparatus according to any one of 11 to 13, wherein the compound represented by the formulas (1) to (6) is a compound represented by the following formulas (25) to (27):

(25)
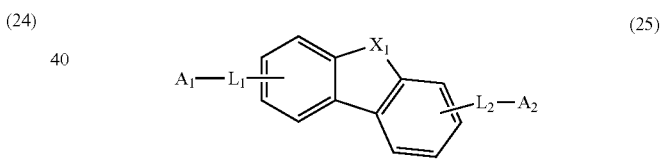

(26)
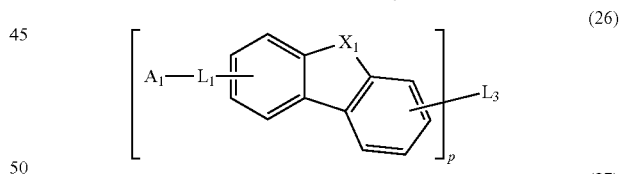

(27)
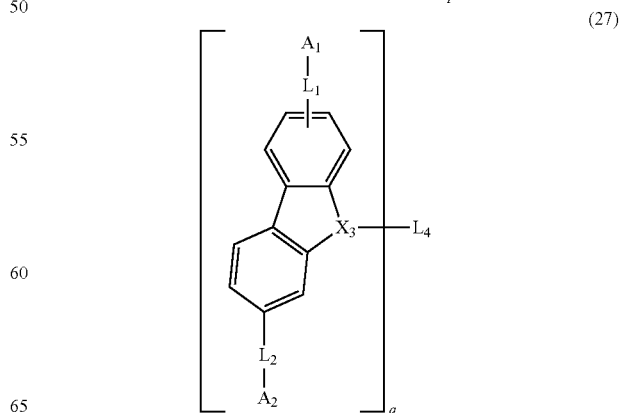

wherein $A^1$, $A^2$, $L^1$ to $L^4$, $X^1$, $X^3$, p and q are independently the same as $A^1$, $A^2$, $L^1$ to $L^4$, $X^1$, $X^3$, p and q in the formulas (1) to (6).

15. The organic electroluminescence multicolor light-emitting apparatus according to 14, wherein $X^1$ in the formulas (25) and (26) is oxygen (O) or sulfur (S).

16. The organic electroluminescence multicolor light-emitting apparatus according to 14, wherein $X^3$ in the formula (27) is nitrogen (N) and $L^4$ is selected from a group including a fused aromatic hydrocarbon skeleton including 14 to 30 ring carbon atoms.

17. The organic electroluminescence multicolor light-emitting apparatus according to any one of 1 to 16, wherein at least one of $A^1$ and $A^2$ as well as $R^1$ are a group selected from a naphthyl group, an anthracenyl group, a phenanthrenyl group, a naphthacenyl group, a benzophenanthrenyl group, a dibenzophenanthrenyl group, a chrysenyl group, a benzochrysenyl group, dibenzochrysenyl group, a fluoranthenyl group, a benzofluoranthenyl group, a triphenylenyl group, a benzotriphenylenyl group, a dibenzotriphenylenyl group, a picenyl group, a benzopicenyl group, a dibenzopicenyl group, a fluorenyl group, a 9,9-dimethytfluorenyl group, a 9,9-diphenylfluorenyl group and a 9,9-spirobifluorenyl group.

18. The organic electroluminescence multicolor light-emitting apparatus according to any one of 1 to 16, wherein $L^4$ is a group selected from a q-valent residue of naphthalene, anthracene, phenanthrene, naphthacene, benzophenanthrene, dibenzophenanthrene, chrysene, benzochrysene, dibenzochrysene, fluoranthene, benzofluoranthene, triphenylene, benzotriphenylene, dibenzotriphenylene, picene, benzopicene, dibenzopicene, 9,9-diphenylfluorene and 9,9-spirobifluorene.

19. The organic electroluminescence multicolor light-emitting apparatus according to any one of 1 to 18, wherein the second organic layer further comprises a hole-transporting material.

20. The organic electroluminescence multicolor light-emitting apparatus according to any one of 1 to 18, wherein the second organic layer is formed of at least a layer comprising the compound represented by the formulas (1) to (6) and a layer comprising a hole-transporting material.

21. The organic electroluminescence multicolor light-emitting apparatus according to 19 or 20, wherein the hole-transporting material comprises an amine skeleton or a carbazole skeleton.

22. The organic electroluminescence multicolor light-emitting apparatus according to any one of 1 to 21, wherein the second organic layer of the first light-emitting device and the second organic layer of the second light-emitting device comprise the same compound.

23. The organic electroluminescence multicolor light-emitting apparatus according to any one of 1 to 22, wherein the film thickness of the second organic layer of the first light-emitting device and the film thickness of the second organic layer of the second light-emitting device are the same.

24. The organic electroluminescence multicolor light-emitting apparatus according to any one of 1 to 23, wherein the first organic layer is a red, yellow or green phosphorescent emitting layer and the third organic layer is a blue fluorescent emitting layer.

25. The organic electroluminescence multicolor light-emitting apparatus according to any one of 1 to 24, wherein the first organic layer is a layer formed by a coating method and the third organic layer is a layer formed by a deposition method.

26. The organic electroluminescence multicolor light-emitting apparatus according to any one of 1 to 25, comprising a hole-injecting and transporting layer formed by a coating method on the anode side of the second organic layer of the second light-emitting device.

According to the invention, an organic EL multicolor light-emitting apparatus having a high efficiency, a long life and a high quality can be provided.

MODE FOR CARRYING OUT THE INVENTION

The organic EL multicolor light-emitting apparatus of the invention comprises a substrate, a cathode and an anode, and between the anode and the cathode, a first light-emitting device and a second light-emitting device being arranged in parallel relationship on the substrate surface.

The first light-emitting device is a stacked body comprising a first organic layer, a second organic layer and a third organic layer being stacked perpendicularly on the substrate in this sequence, for example. The second light-emitting device is a stacked body comprising a second organic layer and a third organic layer being stacked perpendicularly on the substrate in this sequence, for example.

The second organic layer of the first light-emitting device and the second organic layer of the second light-emitting device are preferably the same although they may be the same or different. The third organic layer of the first light-emitting device and the third organic layer of the second light-emitting device are preferably the same although they may be the same or different In the organic EL multicolor emitting apparatus of the invention, a first light-emitting device and a second light-emitting device are disposed on a substrate. It is preferred that the first organic layer of the first light-emitting device and the third organic layer of the second light-emitting device be emitting layers which emit light of different colors.

Each device may comprise other layers. For example, between the third organic layer of the first light-emitting device and the cathode, and between the third organic layer of the second light-emitting device and the cathode, an electron-transporting layer may further be provided. Further, for example, between the first organic layer of the first light-emitting device and the anode, and between the second organic layer of the second light-emitting device and the anode, a hole-transporting region (hole-transporting layer, a hole-injecting layer or the like) may be provided.

An insulating layer may be provided within each device and/or between devices. For example, an insulating layer which insulates the anode of the first light-emitting device and the first organic layer against the second light-emitting device.

Figure 1:
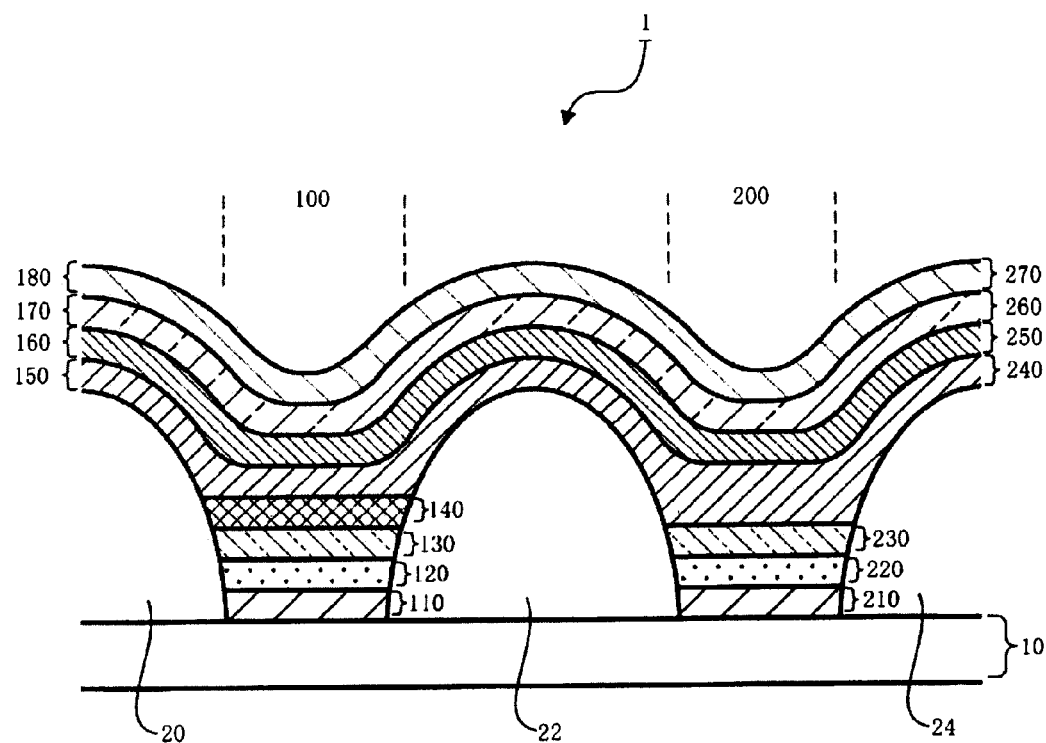
FIG. 1 is a view showing one embodiment of the organic EL multicolor light-emitting apparatus of the invention.
Figure 2:
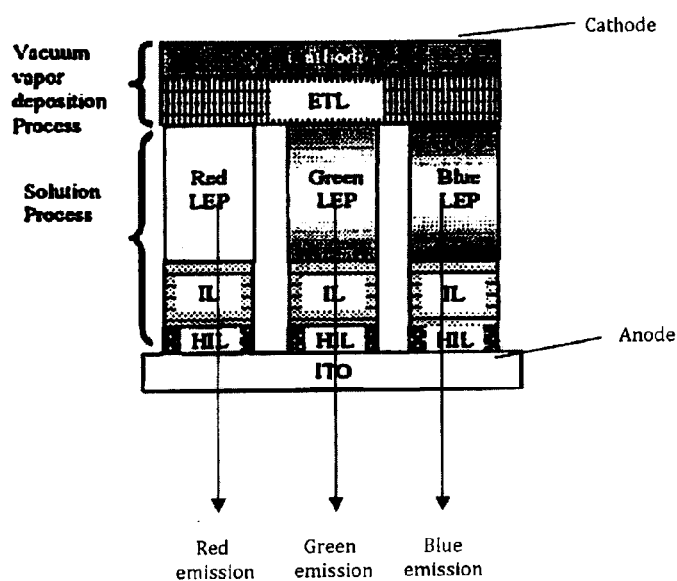
FIG. 2 is a schematic cross-sectional view of an all-coating-type organic EL display.
Figure 3:
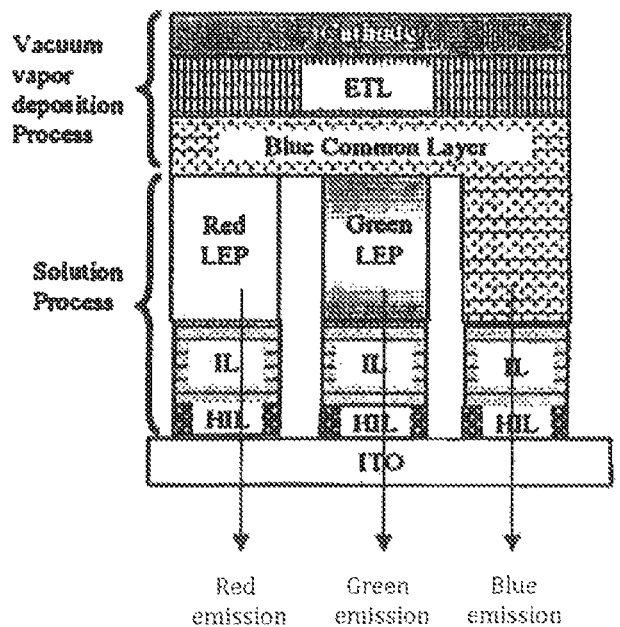
FIG. 3 is a schematic cross-sectional view of a coating type/deposition type hybrid organic EL display.
Figure 4:
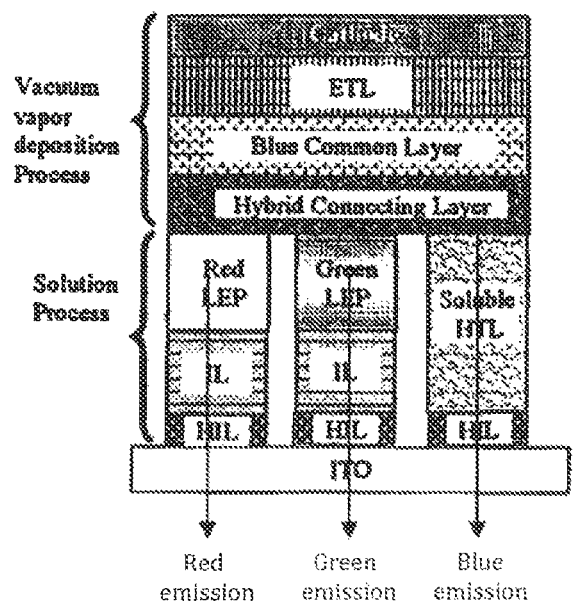
FIG. 4 is a schematic cross-sectional view of an organic EL display provided with a hybrid connecting layer.

FIG. 1 is a schematic cross-sectional view showing one embodiment of the organic EL multicolor light-emitting apparatus of the invention.

An organic EL multicolor light-emitting apparatus 1 is an apparatus in which a first light-emitting device 100 and a second light-emitting device 200 are provided in parallel on a substrate 10.

The first light-emitting device 100 is a stacked body in which, between an anode 110 and a cathode 180, a hole-injecting layer 120, a hole-transporting layer 130, a first emitting layer 140, a first adjacent layer 150, a second emitting layer 160 and an electron-transporting layer 170 are provided in this sequence. Further, a second light-emitting device 200 is a stacked body in which, between an anode 210 and a cathode 270, a hole-injecting layer 220, a hole-transporting layer 230, a second adjacent layer 240, a second emitting layer 250 and an electron-transporting layer 260 are provided in this sequence.

Between the first light-emitting device 100 and the second light-emitting device 200, interlayer insulating films 20, 22 and 24 are provided. The anode 110, the hole-injecting layer 120, the hole-transporting layer 130 and the first emitting layer 140 of the first light-emitting device 100 and the anode 210, the hole-injecting layer 220 and the hole-transporting layer 230 of the second light-emitting device 200 are stacked while being interposed by the interlayer insulating films 20, 22 and 24. On the other hand, the first adjacent layer 150, the second emitting layer 160 and the electron-transporting layer 170 of the first light-emitting device 100 are the same as the second adjacent layer 240, the second emitting layer 250 and the electron-transporting layer 260 of the second light-emitting device 200. These layers are provided such that they cover the interlayer insulating films 20, 22 and 24. The second emitting layer 160 of the first light-emitting device 100 also functions as the electron-transporting layer.

In the first light-emitting device 100 of the organic EL multicolor light-emitting apparatus 1, the first emitting layer 140 corresponds to the first organic layer of the first light-emitting device of the invention, the first adjacent layer 150 corresponds to the second organic layer of the first light-emitting device of the invention, and the second emitting layer 160 corresponds to the third organic layer of the first light-emitting device of the invention. Similarly, in the second light-emitting device 200 of the organic EL multicolor light-emitting apparatus 1, the second adjacent layer 240 corresponds to the second organic layer of the second light-emitting device, and the second emitting layer 250 corresponds to the third organic layer of the second light-emitting device. As shown in FIG. 1, the first and second light-emitting devices may contain other layers in addition to the first organic layer, the second organic layer and the third organic layer.

In the organic EL multicolor light-emitting apparatus 1, the first adjacent layer 150 and the second adjacent layer 240, the second emitting layer 160 and the second emitting layer 250, the electron-transporting layer 170 and the electron-transporting layer 260, and the cathode 180 and the cathode 270 are respectively the same layers and can be formed of the same compound. Therefore, these layers can be formed simultaneously by deposition without using a mask. This particularly leads to an improvement in productivity when the first light-emitting device and the second light-emitting device emit different colors.

In FIG. 1, the anode is formed on the substrate, and the layers are stacked thereon. However, it is possible to form the cathode on the substrate, and each layer may be formed thereon in a reverse order (from the electron-transporting layer to the hole-injecting layer).

In FIG. 1, the first light-emitting device is a green light-emitting device and the second light-emitting device is a blue light-emitting device. The first light-emitting device and the second light-emitting device may be a yellow light-emitting device and a blue light-emitting device, respectively.

In FIG. 1, a third light-emitting device (a red light-emitting device), which has the same configuration as that of the first light-emitting device except that the first emitting layer of the first light-emitting device is a red-emitting layer, may further be provided. Such a third light-emitting device is preferably provided in adjacent to the first light-emitting device.

It is preferred that the first light-emitting device be a green phosphorescent light-emitting device, the second light-emitting device be a blue fluorescent light-emitting device and the third light-emitting device be a red phosphorescent light-emitting device.

Hereinbelow, for each layer of the organic EL multicolor light-emitting apparatus of the invention, an explanation is made by referring to each layer of the organic EL multicolor light-emitting apparatus 1 shown in FIG. 1.

[Adjacent Layer]

In the organic EL multicolor light-emitting apparatus of the invention, a first adjacent layer and a second adjacent layer, i.e. two second organic layers of the first light-emitting device and the second light-emitting device, independently comprises any one of compounds represented by the following formulas (1) to (6):

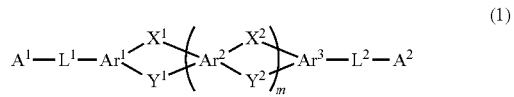

(1)

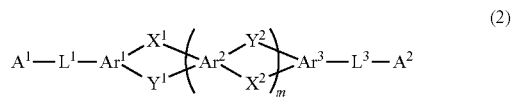

(2)

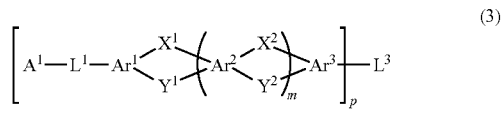

(3)

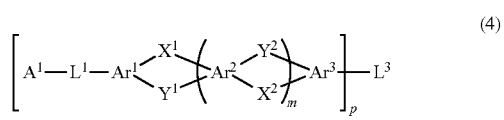

(4)

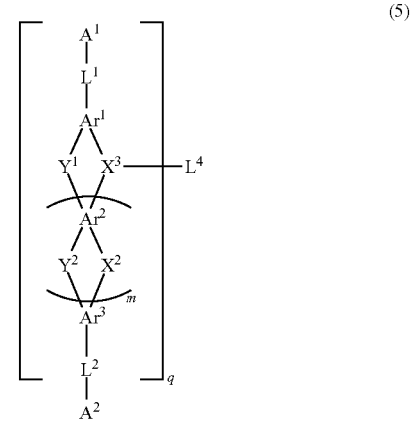

(5)

-continued

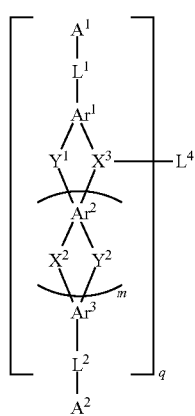

(6)

The compound represented by the formulas (1) to (6) have both of the following functions: hole-injecting properties and hole-transporting properties and electron-injecting properties and electron-transporting properties. As a result, the second organic layer of the first light-emitting device has electron-injection properties and electron-transporting properties, and the second organic layer of the second light-emitting device has hole-injecting properties and hole-transporting properties.

Further, the compound in the second organic layer has an effect of maintaining a high triplet energy, and can prevent diffusion of triplet energy from a red and yellow phosphorescent emitting layer or a green phosphorescent emitting layer, whereby phosphorescent emission efficiency can be increased.

The triplet energy means a difference in energy between the lowest excited triplet state and the ground state.

In the formulas (1) to (6), $Ar^1$, $Ar^2$ and $Ar^3$ are independently a substituted or unsubstituted aromatic hydrocarbon group including 6 carbon atoms that form a ring (hereinafter referred to as "ring carbon atoms") or a substituted or unsubstituted aromatic heterocyclic group including 6 atoms that form a ring (hereinafter referred to as "ring atoms").

$Ar^1$, $Ar^2$ and $Ar^3$ may have one or plural substituent(s) Y. If the number of Y is plural, Ys may be the same or different.

Y is a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms.

In the formulas (1) to (4), $X^1$ and $X^2$ are independently oxygen (O), sulfur (S), >N—$R^1$, >$CR^2R^3$, >$BR^4$, >$SiR^5R^6$, >C=$NR^7$, >C=$CR^8R^9$, >S=O, >$SO_2$, >$PR^{10}$ or >P(=O)$R^{11}$; and $Y^1$ and $Y^2$ are independently a single bond, oxygen (O), sulfur (S), >N—$R^1$, >$CR^2R^3$, >$BR^4$, >$SiR^5R^6$, >C=$NR^7$, >C=$CR^8R^9$, >S=O, >$SO_2$, >$PR^{10}$ or >P(=O) $R^{11}$.

Meanwhile, the ">X" indicates that the element forming the fused ring together with $Ar^1$ to $Ar^3$ is X. For example, in ">N—$R^1$", nitrogen (N) is the element constituting the fused ring.

In the formulas (5) and (6), $X^3$ is nitrogen (N), >$CR^2$, B (boron), >SiR5, phosphorus (P) or >P=0; $X^2$ is oxygen (O), sulfur (S), >N—$R^1$, >$CR^2R^3$, >$BR^4$, >$SiR^5R^6$, >C=$NR^7$, >C=$CR^8R^9$, >S=O, >$SO_2$, >$PR^{10}$ or >P(=O)$R^{11}$; and $Y^1$ and $Y^2$ are independently a single bond, oxygen (O), sulfur (S), >N—$R^1$, >$CR^2R^3$, >$BR^4$, >$SiR^5R^6$, >C=$NR^7$, >C=$CR^8R^9$, >S=O, >$SO_2$, >$PR^{10}$ or >P(=O)$R^{11}$.

$R^1$ to $R^{11}$ are independently a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms.

$X^3$ is preferably nitrogen (N). If $X^3$ is nitrogen, more stabilization for electrons and holes can be attained, whereby a light-emitting device having a long life can be obtained.

m is an integer of 0 to 3.

p and q are independently an integer of 2 to 4. That is, the formulas (3) to (6) are independently a dimer, a trimer or a tetramer of the compound in [ ] with $L^3$ or $L^4$ being a bonding group.

p and q are preferably 2.

In the formulas (1), (2), (5) and (6), $L^1$ and $L^2$ are independently a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms.

In the formulas (3) and (4), $L^1$ is a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms.

In the formulas (3) and (4), $L^3$ is, when p is 2, a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms.

In the formulas (5) and (6), $L^4$ is, when q is 2, a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms.

In the formulas (3) and (4), $L^3$ is, when p is 3, a substituted or unsubstituted trivalent saturated hydrocarbon group including 1 to 20 carbon atoms, a substituted or unsubstituted trivalent cyclic saturated hydrocarbon group including 3 to 20 carbon atoms, a trivalent silyl group or a trivalent substituted silyl group including 3 to 20 carbon atoms, a substituted or unsubstituted trivalent aromatic hydrocarbon group including 6 to 30 ring carbon atoms or a substituted or unsubstituted trivalent aromatic heterocyclic group including 5 to 30 ring atoms.

In the formulas (5) and (6), $L^4$ is, when q is 3, a substituted or unsubstituted trivalent saturated hydrocarbon group including 1 to 20 carbon atoms, a substituted or unsubstituted trivalent cyclic saturated hydrocarbon group including 3 to 20 carbon atoms, a trivalent silyl group or a trivalent substituted silyl group including 3 to 20 carbon atoms, a substituted or unsubstituted trivalent aromatic hydrocarbon group including 6 to 30 ring carbon atoms or a substituted or unsubstituted trivalent aromatic heterocyclic group including 5 to 30 ring atoms.

In the formulas (3) and (4), $L^3$ is, when p is 4, a substituted or unsubstituted tetravalent saturated hydrocarbon group including 1 to 20 carbon atoms, a substituted or unsubstituted tetravalent cyclic saturated hydrocarbon group including 3 to 20 carbon atoms, a tetravalent silyl group or a substituted tetravalent silyl group including 3 to 20 carbon atoms, a substituted or unsubstituted tetravalent aromatic hydrocarbon group including 6 to 30 ring carbon atoms or a substituted or unsubstituted tetravalent aromatic heterocyclic group including 5 to 30 ring atoms.

In the formulas (5) and (6), $L^4$ is, when q is 4, a substituted or unsubstituted tetravalent saturated hydrocarbon group including 1 to 20 carbon atoms, a substituted or unsubstituted tetravalent cyclic saturated hydrocarbon group including 3 to 20 carbon atoms, a tetravalent silyl group or a substituted tetravalent silyl group including 3 to 20 carbon atoms, a substituted or unsubstituted tetravalent aromatic hydrocarbon group including 6 to 30 ring carbon atoms or a substituted or unsubstituted tetravalent aromatic heterocyclic group including 5 to 30 ring atoms.

In the formulas (1), (2), (5) and (6), $A^1$ and $A^2$ are independently a hydrogen atom, a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms.

In the formulas (3) and (4), $A^1$ is a hydrogen atom, a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms, or a substituted or unsubstituted aromatic heterocyclic group including 5 to 30 ring atoms.

When both $X^1$ and $X^2$ are $>$N—$R^1$, when both $Y^1$ and $Y^2$ are $>$N—$R^1$, or when $X^2$ is $>$N—$R^1$ and $X^3$ is nitrogen (N), $L^4$ or at least one of $R^1$ is selected from a group including a furan skeleton, a group including a thiophene skeleton, and a group including a fused aromatic hydrocarbon skeleton including 14 to 30 ring carbon atoms.

Here, the group comprising a furan skeleton, the group comprising a thiophene skeleton and the group comprising a fused aromatic hydrocarbon skeleton including 14 to 30 ring carbon atoms are independently a group that comprises at least a furan skeleton represented by the following formula (I), a thiophene skeleton represented by the following formula (II) and a fused aromatic hydrocarbon skeleton including 14 to 30 ring carbon atoms.

(I)

(II)

As examples of the fused aromatic hydrocarbon skeleton including 14 to 30 ring carbon atoms, phenanthrene, naphthacene, benzophenanthrene, dibenzophenanthrene, chrysene, benzochrysene, dibenzochrysene, fluoranthene, benzofluoranthene, triphenylene, benzotriphenylene, dibenzotriphenylene, picene, benzopicene, dibenzopicene and 9,9-spirobifldorene can be given.

As for the furan skeleton, the thiophene skeleton and the fused aromatic hydrocarbon skeleton including 14 to 30 ring carbon atoms, they may be substituted by a substituent mentioned later; the ring may be fused; or may have a bonding group for bonding with other atoms (e.g. nitrogen (N)) (i.e. the substituent further contributes to bonding with other atoms).

As examples of the group comprising a furan skeleton, a furanyl group, a benzofuranyl group, a dibenzofuranyl group, a (2-dibenzofuranyl)phenyl group, a (4-dibenzofuranyl)phenyl group or the like can be given. In respect of stability of the skeleton, a dibenzofuranyl group, a (2-dibenzofuranyl)phenyl group and a (4-dibenzofuranyl)phenyl group are preferable.

As examples of the group comprising a thiophene skeleton, a thiophenyl group, a benzothiophenyl group, a dibenzothiophenyl group, a (2-dibenzothiophenyl)phenyl group, a (4-dibenzothiophenyl)phenyl group or the like can be given. In respect of stability of the skeleton, a benzothiophenyl group, a dibenzothiophenyl group, a (2-dibenzothiophenyl)phenyl group and a (4-dibenzothiophenyl)phenyl group are preferable.

As examples of the group including a fused aromatic hydrocarbon skeleton including 14 to 30 ring carbon atoms, a mono- to q-valent group of the fused aromatic hydrocarbon skeleton including 14 to 30 ring carbon atoms or one including a bonding group such as a phenylene group can be given. In respect of stability of the skeleton or high triplet energy, a mono- to q-valent group of phenanthrene, triphenylene or 9,9-spirobifluorene, a phenanthrenylphenyl group, a triphenylenylphenyl group and a 9,9-spirobifluorenylphenyl group are preferable.

Among the compounds represented by the formulas (1) to (6), a compound in which m is 1 and $Y^1$ and $Y^2$ are a single bond is preferable. For example, as the compound represented by the formula (1) or (2), a compound represented by the following formulas (7) to (12) can be given. As the compound represented by the formula (3) or (4), a compound represented by the following formulas (13) to (18) can be given. As the compound represented by the formula (5) or (6), a compound represented by the following formulas (19) to (24) can be given.

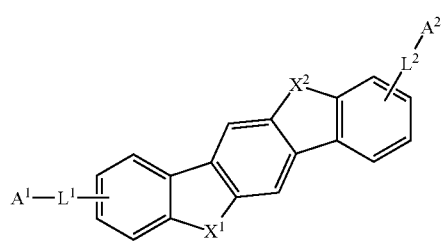
(7)
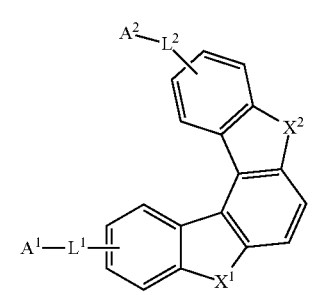
(8)
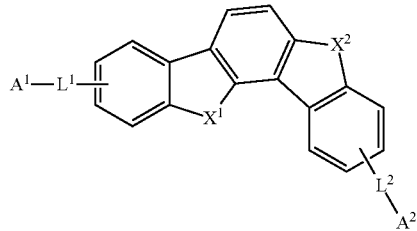
(9)
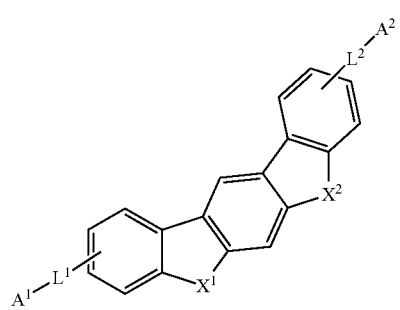
(10)
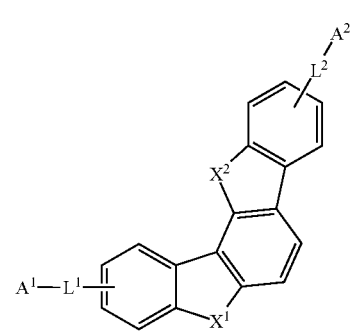
(11)
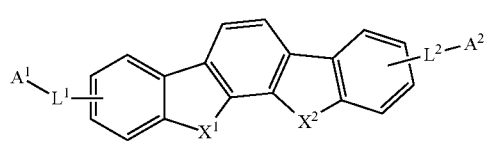
(12)
-continued
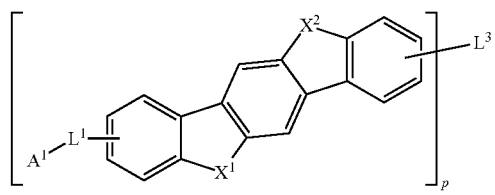
(13)
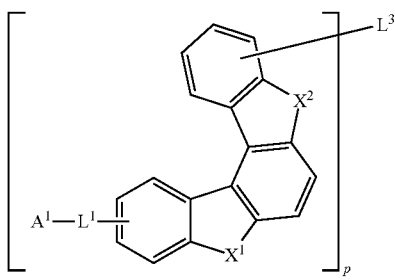
(14)
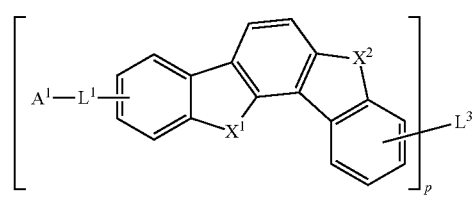
(15)
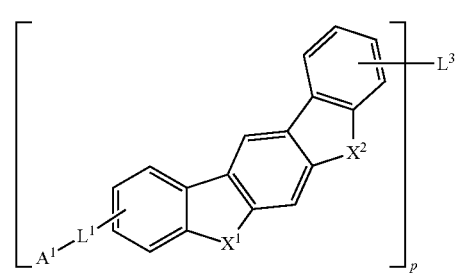
(16)
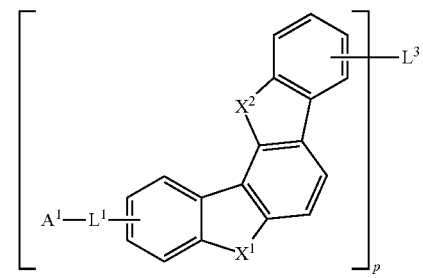
(17)
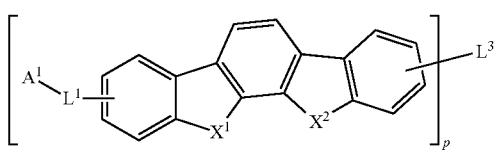
(18)

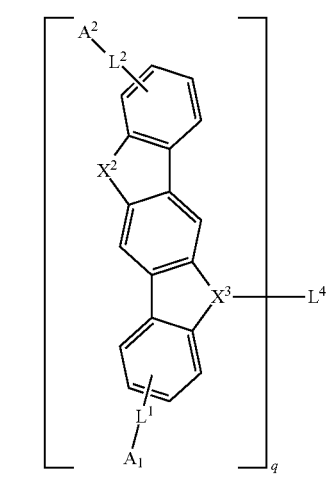

(19)

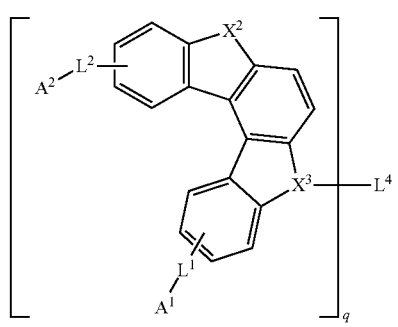

(20)

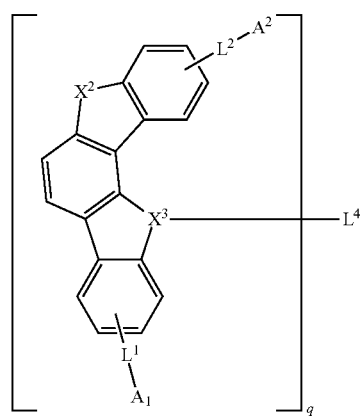

(21)

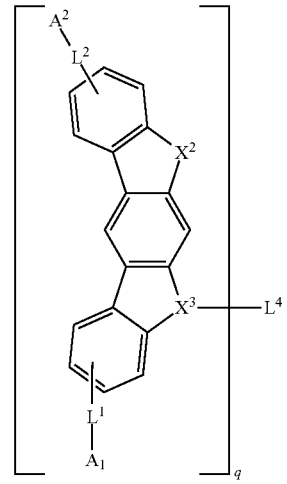

(22)

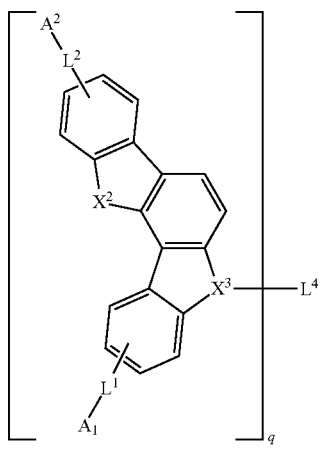

(23)

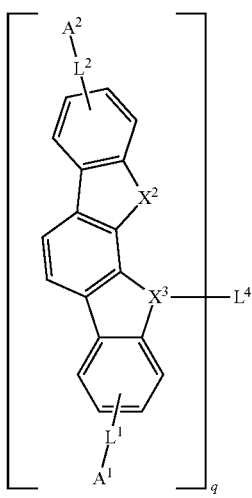

(24)

In the formulas (7) to (24). $A^1$, $A^2$, $L^1$ to $L^4$, $X^1$ to $X^3$, p and q are independently the same as that in formulas (1) to (6).

$X^1$ or $X^2$ is preferably an element or a group selected from oxygen (O), sulfur (S) and $>$N—$R^1$ (wherein $R^1$ is the same as $R^1$ in the formulas (1) to (6)). It is particularly preferred that $X^1$ or $X^2$ be oxygen (O). As a result, as compared with a case when $X^1$ or $X^2$ is S or $>$N—$R^1$, more stabilization can be attained for electrons and holes, whereby a further long-lived light-emitting device can be obtained.

It is preferred that $R^1$ in $>N-R^1$ be a group including a fused aromatic hydrocarbon skeleton including 10 to 30 ring carbon atoms or a group including an aromatic heterocyclic skeleton including 9 to 30 ring atoms. By this, the compound can be not only structurally fast and can be stable for electrons and holes, but also have increased heat resistance, whereby a more reliable light-emitting device can be obtained.

In the compound represented by the formula (1) or (2), when m is 0, at least one of $A^1$ and $A^2$ is preferably a group including a fused aromatic hydrocarbon skeleton including 10 to 30 ring carbon atoms or a group including an aromatic heterocyclic skeleton including 9 to 30 ring atoms. It is particularly preferred that $Y^1$ and $Y^2$ be a single bond.

Similarly, in the compound represented by the formula (5) or (6), when m is 0, $L^4$ is preferably a group including a fused aromatic hydrocarbon skeleton including 10 to 30 ring carbon atoms or a group including an aromatic heterocyclic skeleton including 9 to 30 ring atoms. It is particularly preferred that $Y^1$ and $Y^2$ be a single bond.

By this, the compound can be not only structurally fast and can be stable for electrons and holes, but also have increased heat resistance, whereby a more reliable light-emitting device can be obtained.

Here, the group including a fused aromatic hydrocarbon skeleton including 10 to 30 ring carbon atoms or the group including an aromatic heterocyclic skeleton including 9 to 30 ring atoms are independently a group that includes at least a fused aromatic hydrocarbon skeleton including 10 to 30 ring carbon atoms or a group that includes at least aromatic heterocyclic skeleton including 9 to 30 ring atoms.

As the fused aromatic hydrocarbon skeleton including 10 to 30 ring carbon atoms, naphthalene, anthracene, phenanthrene, naphthacene, benzophenanthrene, dibenzophenanthrene, chrysene, benzochrysene, dibenzochrysene, fluoranthene, benzofluoranthene, triphenylene, benzotriphenylene, dibenzotriphenylene, picene, benzopicene, dibenzopicene and 9,9-spirobifluorene or the like can be given.

As the aromatic heterocyclic skeleton including 9 to 30 ring atoms, an isoindole ring, a benzofuran ring, an isobenzofuran ring, a dibenzothiophene ring, an isoquinoline ring, a quinoxaline ring, a phenanthridine ring, a phenanthroline ring, an indole ring, a quinoline ring, a quinazoline ring, an acridine ring, a benzoxazole ring, a benzothiazole ring, a benzoimidazole ring, a dibenzofuran ring, a carbazole ring or the like can be given.

As for the fused aromatic hydrocarbon skeleton including 10 to 30 ring carbon atoms or the aromatic heterocyclic ring skeleton including 9 to 30 ring atoms, they may be substituted by a substituent mentioned later the ring may be fused, or may have a bonding group for bonding with other atoms (e.g. nitrogen (N) and carbon (C)) (i.e. the substituent further contributes to bonding with other atoms).

As examples of the group including the fused aromatic hydrocarbon skeleton including 10 to 30 ring carbon atoms, a mono- to q-valent group of the above-mentioned fused aromatic hydrocarbon skeleton including 10 to 30 ring carbon atoms, and further, one having a bonding group such as phenylene can be given. In respect of stability of the skeleton or high triplet energy, a mono- to q-valent group of naphthalene, phenanthrene, triphenylene or 9,9-spirobifluorene; a naphthylphenyl group, a phenanthrenylphenyl group, a triphenylenylphenyl group and a 9,9-spirobifluorenylphenyl group are preferable.

As examples of the group including the aromatic heterocyclic ring skeleton including 9 to 30 ring atoms, a mono- to q-valent group of the aromatic heterocyclic ring skeleton including 9 to 30 ring atoms, or one including a bonding group such as a phenylene group can be given. In respect of stability of the skeleton or high triplet energy, a mono- to q-valent group of a dibenzothiophenyl group, an isoquinolinyl group, a quinoxalinyl group, a phenanthrolinyl group, a quinolinyl group, a quinazolinyl group, an acridinyl group, a dibenzofuranyl group or a carbazolyl group, a dibenzothiophenylphenyl group, an isoquinolinylphenyl group, a quinoxalinylphenyl group, a phenanthrolinylphenyl group, a quinolinylpropyl group, a quinazolinylphenyl group, an acridinylphenyl group, a dibenzofuranyl phenyl group and a carbazolylphenyl group are preferable.

When m is 0, the formula (1) and the formula (2) show the same compound. Similarly, the formula (3) and the formula (4) show the same compound, and the formula (5) and the formula (6) show the same compound.

In the case where m is 0, compounds represented by the following formulas (25) to (27) can be given.

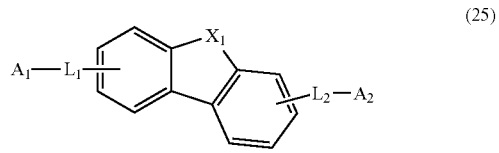

(25)

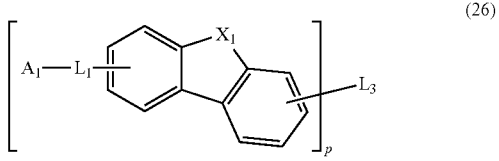

(26)

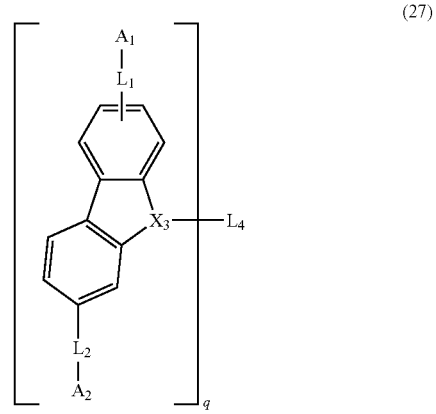

(27)

In the formulas (25) to (27), $A^1$, $A^2$, $L^1$ to $L^4$, $X^1$, $X^3$, p and q are independently the same as that in the formulas (1) to (6).

$X^1$ in the formula (25) and (26) is preferably oxygen (O) or sulfur (S). By this, more stabilization for electrons and holes can be attained, whereby a long-lived light-emitting device can be obtained.

In the formula (27), $X^3$ is preferably nitrogen (N) and $L^4$ is preferably selected from a group including a fused aromatic hydrocarbon skeleton including 14 to 30 ring carbon atoms. By this, more stabilization for electrons and holes can be attained, whereby a long-lived light-emitting device can be obtained.

The group including a fused aromatic hydrocarbon skeleton including 14 to 30 ring carbon atoms is the same as those mentioned above.

In the formulas (1) to (27), it is preferred that at least one of $A^1$ and $A^2$ as well as $R^1$ be a group selected from a naphthyl group, an anthracenyl group, a phenanthrenyl group, a naphthacenyl group, a benzophenanthreny group, a dibenzophenanthrenyl group, a chrysenyl group, a benzochrysenyl group, a dibenzochrysenyl group, a fluoranthenyl group, a benzofluoranthenyl group, a triphenylenyl group, a benzotriphenylenyl group, a dibenzotriphenylenyl group, a picenyl group, a benzopicenyl group, a dibenzopicenyl group, a fluorenyl group, a 9,9-dimethylfluorenyl group, a 9,9-diphenylfluorenyl group and a 9,9-spirobifluorenyl group.

In the formulas (5), (6) and (19) to (27), it is preferred that $L^4$ be a group selected from a q-valent residue of naphthalene, anthracene, phenanthrene, naphthacene, benzophenanthrene, dibenzophenanthrene, chrysene, benzochrysene, dibenzochrysene, fluoranthene, benzofluoranthene, triphenylene, benzotriphenylene, dibenzotriphenylene, picene, benzopicene, dibenzopicene, 9,9-diphenylfluorene and 9,9-spirobifluorene.

By this, the compound can be not only structurally fast and can be stable for electrons and holes, but also have increased heat resistance, whereby a more reliable light-emitting device can be obtained.

Hereinbelow, specific examples of each group in the formulas (1) to (27) will be explained.

In this specification, the "a to b carbon atoms" in the "substituted or unsubstituted XX group including a to b carbon atoms" mean the number of carbon atoms when the XX group is unsubstituted, and does not include the number of carbon atoms of the substituent when the XX group is substituted.

In the material for an organic EL device of the invention, the hydrogen atom includes isomers differing in number of neutrons, i.e. protium, deuterium and tritium.

As the alkyl group including 1 to 20 carbon atoms, the alkylene group including 1 to 20 carbon atoms or the trivalent or tetravalent saturated hydrocarbon group including 1 to 20 carbon atoms represented by Y, $A^1$, $A^2$, $L^1$ to $L^4$ and $R^1$ to $R^{11}$, a methyl group, an ethyl group, a propyl group, an isopropyl group, an n-butyl group, a s-butyl group, a t-butyl group, an isobutyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 2-methylpentyl group, a 1-pentylhexyl group, a 1-butylpentyl group, a 1-heptyloctyl group, a 3-methylpentyl group or a di- to tetravalent group of these can be given, for example. A methyl group, an ethyl group, a propyl group, an isopropyl group, an n-butyl group, a s-butyl group, an isobutyl group, a t-butyl group, a n-pentyl group, a n-hexyl group, a n-heptyl group, a n-octyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a neopentyl group, a 1-methylpentyl group, a 1-pentylhexyl group, a 1-butylpentyl group, a 1-heptyloctyl group or a di- to tetravalent group of these are preferable.

As the substituted or unsubstituted cycloalkyl group including 3 to 20 ring carbon atoms, the substituted or unsubstituted cycloalkylene group including 3 to 20 ring carbon atoms or the trivalent or tetravalent cyclic saturated hydrocarbon group including 3 to 20 ring carbon atoms represented by Y, $A^1$, $A^2$, $L^1$ to $L^4$ and $R^1$ to $R^{11}$, a cyclopropyl group, a cyclobutyl group, a cyclopentyl group, a cyclohexyl group or a di- to tetravalent group of these can be given, for example. A cyclobutyl group, a cyclopentyl group, a cyclohexyl group or a di- to tetravalent group of these are preferable.

As the alkoxy group including 1 to 20 carbon atoms represented by Y, $A^1$, $A^2$ and $R^1$ to $R^{11}$, a methoxy group, an ethoxy group, an i-propoxy group, a n-propoxy group, a n-butoxy group, a s-butoxy group, a t-butoxy group or the like can be given. A methoxy group, an ethoxy group, a methoxy group, an i-propoxy group and a n-propoxy group are preferable.

As the aralkyl group including 7 to 24 carbon atoms represented by Y, $A^1$, $A^2$ and $R^1$ to $R^{11}$, a benzyl group, a phenethyl group, a phenylpropyl group or the like can be given, for example.

As the mono- to tetravalent substituted silyl group including 3 to 20 carbon atoms represented by Y, $A^1$, $A^2$, $L^1$ to $L^4$ and $R^1$ to $R^{11}$, a trimethylsilyl group, a triethylsilyl group, a tributylsilyl group, a trioctylsilyl group, a triisobutylsilyl group, a dimethylethylsilyl group, a dimethylisopropylsilyl group, a dimethylpropylsilyl group, a dimethylbutylsilyl group, a dimethyl-tert-butylsilyl group, a diethylisopropylsilyl group, a phenyldimethylsilyl group, a diphenylmethylsilyl group, a diphenyl-tert-butylsilyl group, a triphenylsilyl group, or a di- to tetravalent group of these can be given, for example. A trimethylsilyl group, a triethylsilyl group, a tributylsilyl group, or a di- to tetravalent group of these are preferable.

As the substituted or unsubstituted aromatic hydrocarbon group including 6 to 30 ring carbon atoms represented by Y and the substituted or unsubstituted mono- to tetravalent aromatic hydrocarbon group including 6 to 30 ring carbon atoms represented by $A^1$, $A^2$, $L^1$ to $L^4$ and $R^1$ to $R^{11}$, a residue having a corresponding number of valence of substituted or unsubstituted benzene, naphthalene, biphenyl, terphenyl, fluorene, phenanthrene, triphenylene, perylene, chrysene, fluoranthene, benzofluorene, benzotriphenylene, benzochrysene or the like (including those indicated by the fused aromatic hydrocarbon skeleton including 10 to 30 ring carbon atoms) can be given, for example. Benzene, naphthalene, biphenyl, terphenyl, fluorene, phenanthrene, triphenylene and 9,9-spirobifluorenone are preferable The aromatic hydrocarbon group including 6 ring carbon atoms represented by $Ar^1$ to $Ar^3$ is a benzene ring.

As the substituted or unsubstituted aromatic heterocyclic group including 5 to 24 ring atoms represented by Y and the substituted or unsubstituted aromatic heterocyclic group including 5 to 30 ring carbon atoms represented by $A^1$, $A^2$, $L^1$ to $L^4$ and $R^1$ to $R^{11}$, a residue having a corresponding number of valence of pyridine, pyridazine, pyrimidine, pyrazine, 1,3,5-triazine, carbazole, dibenzofuran, dibenzothiophene, phenoxazine, phenothiazine, dihydroacridine, isoquinoline, quinoxaline, phenanthroline, quinoline, quinazoline, acridine or the like (including those indicated by the aromatic heterocyclic skeleton including 9 to 30 ring atoms) can be given, for example. Pyridine, pyridazine, pyrimidine, pyrazine, carbazole, dibenzofuran, dibenzothiophene, phenoxazine, dibenzothiophene, isoquinoline, quinoxaline, phenanthroline, quinoline, quinazoline and acridine are preferable.

As the aromatic heterocyclic group including 6 ring atoms represented by $Ar^1$ to $Ar^3$, pyridine, pyridazine, pyrimidine, pyrazine, 1,3,5-triazine or the like can be given.

As the substituent that may substitute each group of the formulas (1) to (27), for example, a substituted or unsubstituted alkyl group including 1 to 10 carbon atoms (a methyl group, an ethyl group, a propyl group, an isopropyl group, a n-butyl group, a s-butyl group, an isobutyl group, a t-butyl group, a n-pentyl group, a n-hexyl group, a n-heptyl group, a n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1, 3-dichloroisopropyl group, a 2, 3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, or the like; a substituted or unsubstituted cycloalkyl group including 3 to 40 ring carbon atoms (a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, or the like); an alkoxy group including 1 to 6 carbon atoms (an ethoxy group, a methoxy group, an i-propoxy group, a n-propoxy group, a s-butoxy group, a t-butoxy group, a pentoxy group, a hexyloxy group or the like), a cycloalkoxy group including 3 to 10 ring carbon atoms (a cyclopentoxy group, a cyclohexyloxy group or the like); an aromatic hydrocarbon group including 6 to 30 ring carbon atoms; an aromatic heterocyclic group including 5 to 30 ring atoms; an ester group including an aromatic hydrocarbon group including 6 to 30 ring carbon atoms; an ester group including an alkyl group including 1 to 6 carbon atoms; a cyano group; a nitro group; a halogen atom or the like can be given.

Among these, an alkyl group including 1 to 6 carbon atoms, a phenyl group, a pyridyl group, a carbazolyl group, a dibenzofuranyl group and a dibenzothiophenyl group are preferable. The number of a substituent is preferably 1 to 2.

These substituents may further be substituted by the above-mentioned substituents.

As specific examples of the compound represented by the formulas (1) to (6), compounds disclosed in WO2009/148015, WO2009/148016, WO2009/148062, JP-A-2012-140365 or the like can be mentioned. The compound can be synthesized by referring to the above-mentioned publications. The invention is not limited to the exemplified compounds.

More specifically, the following compounds can be given.

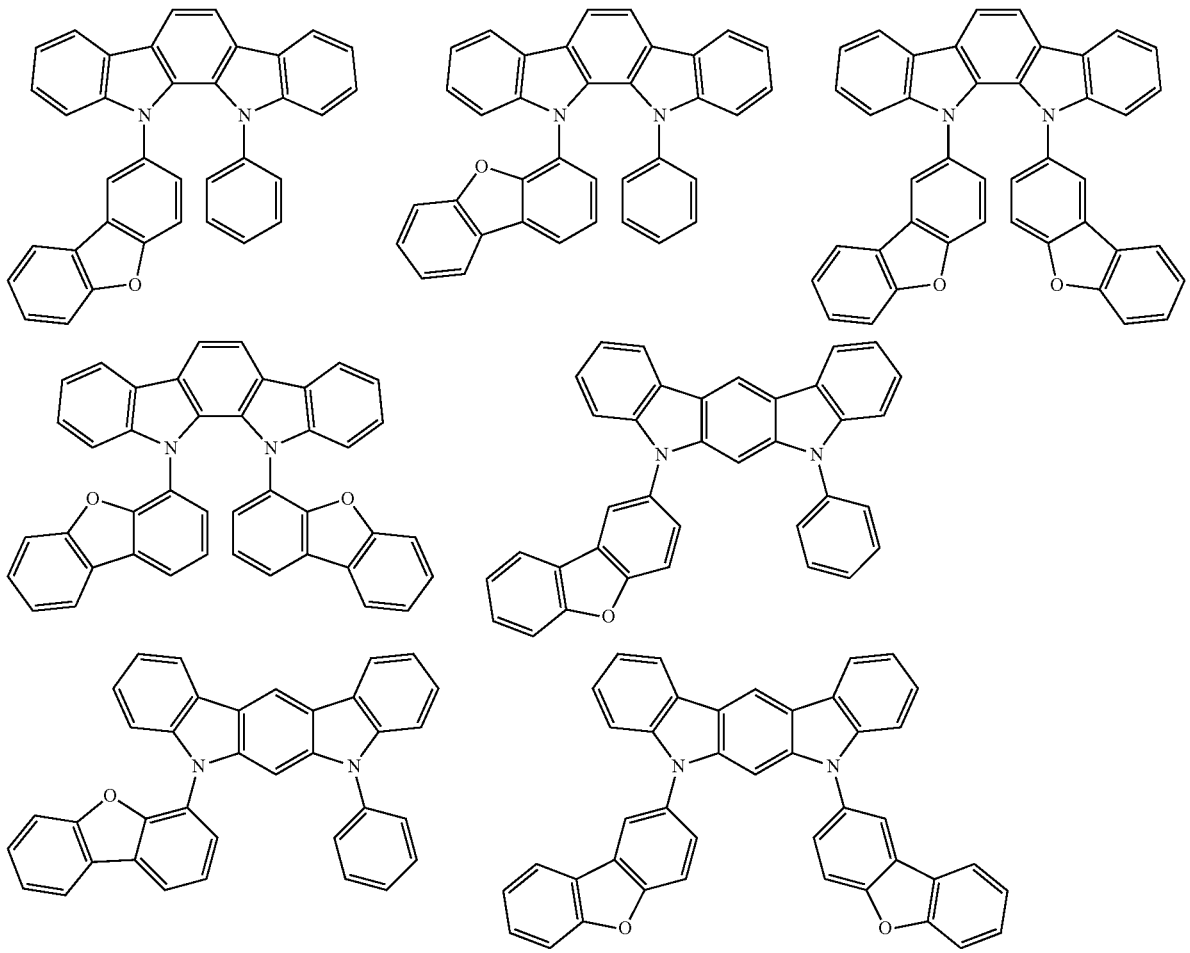

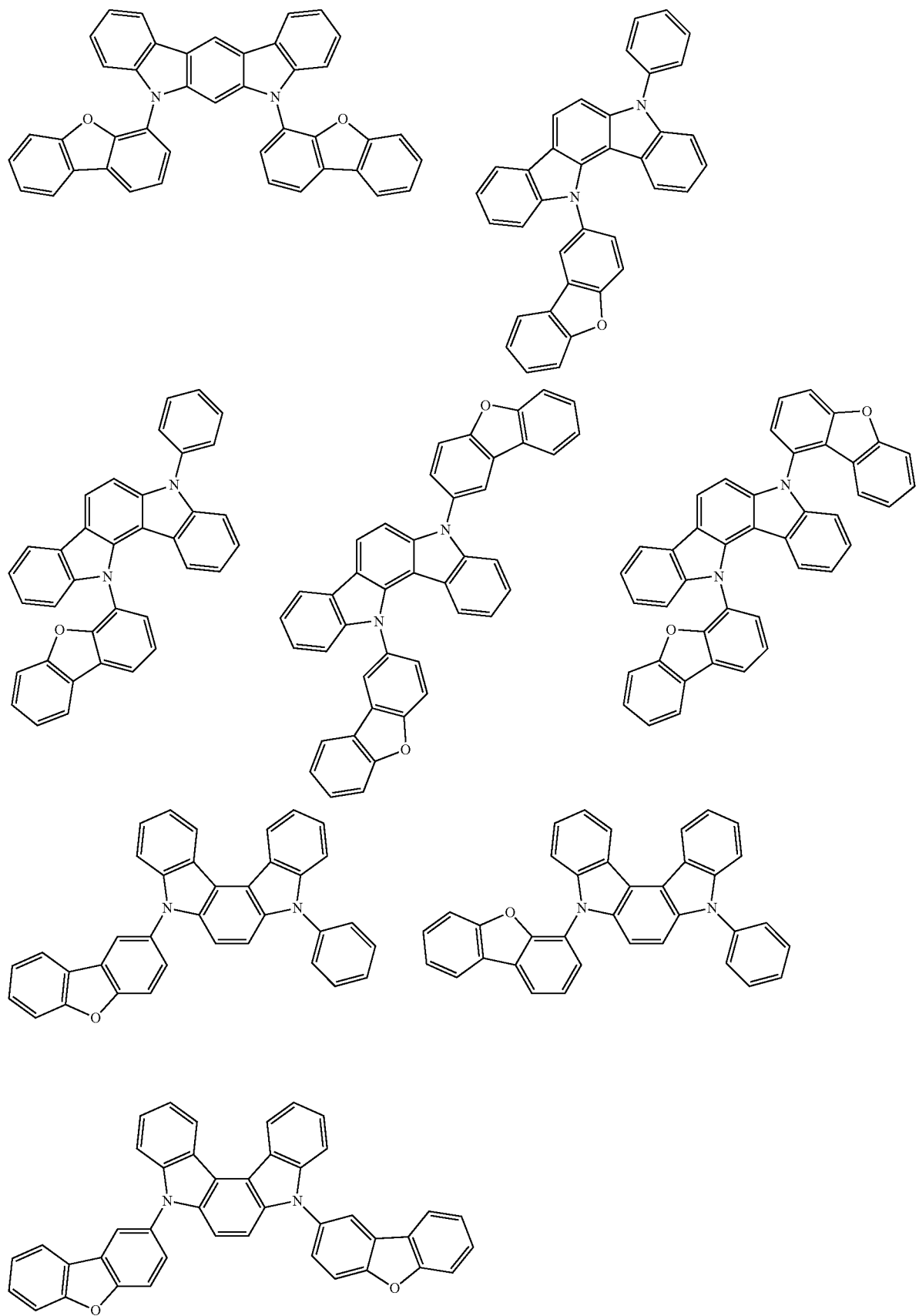

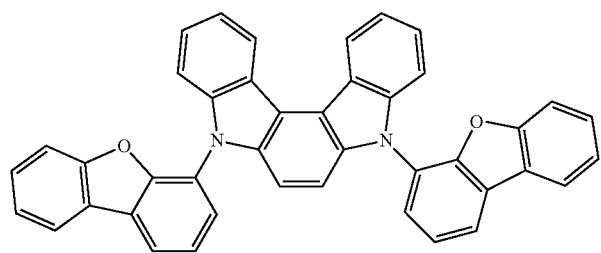

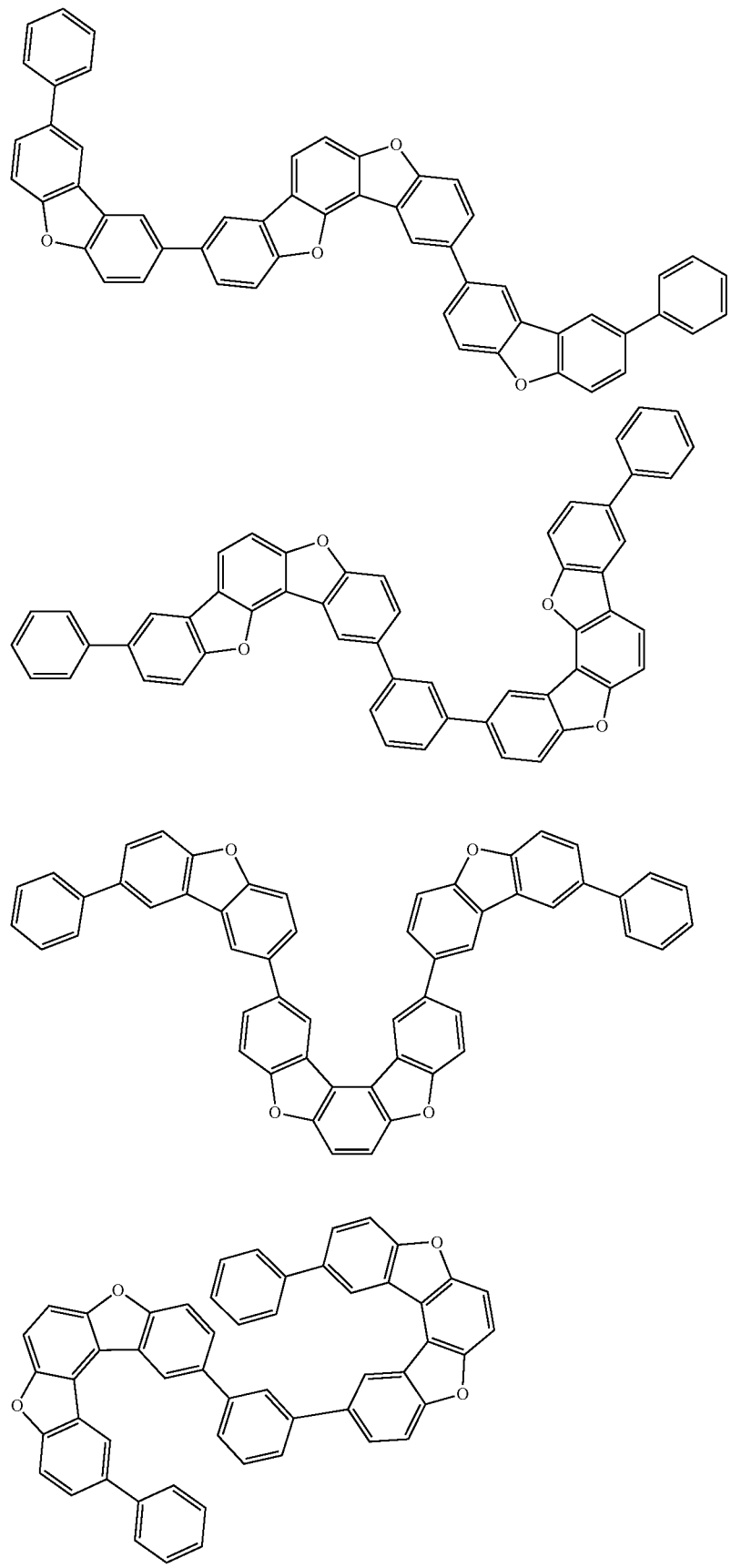

-continued
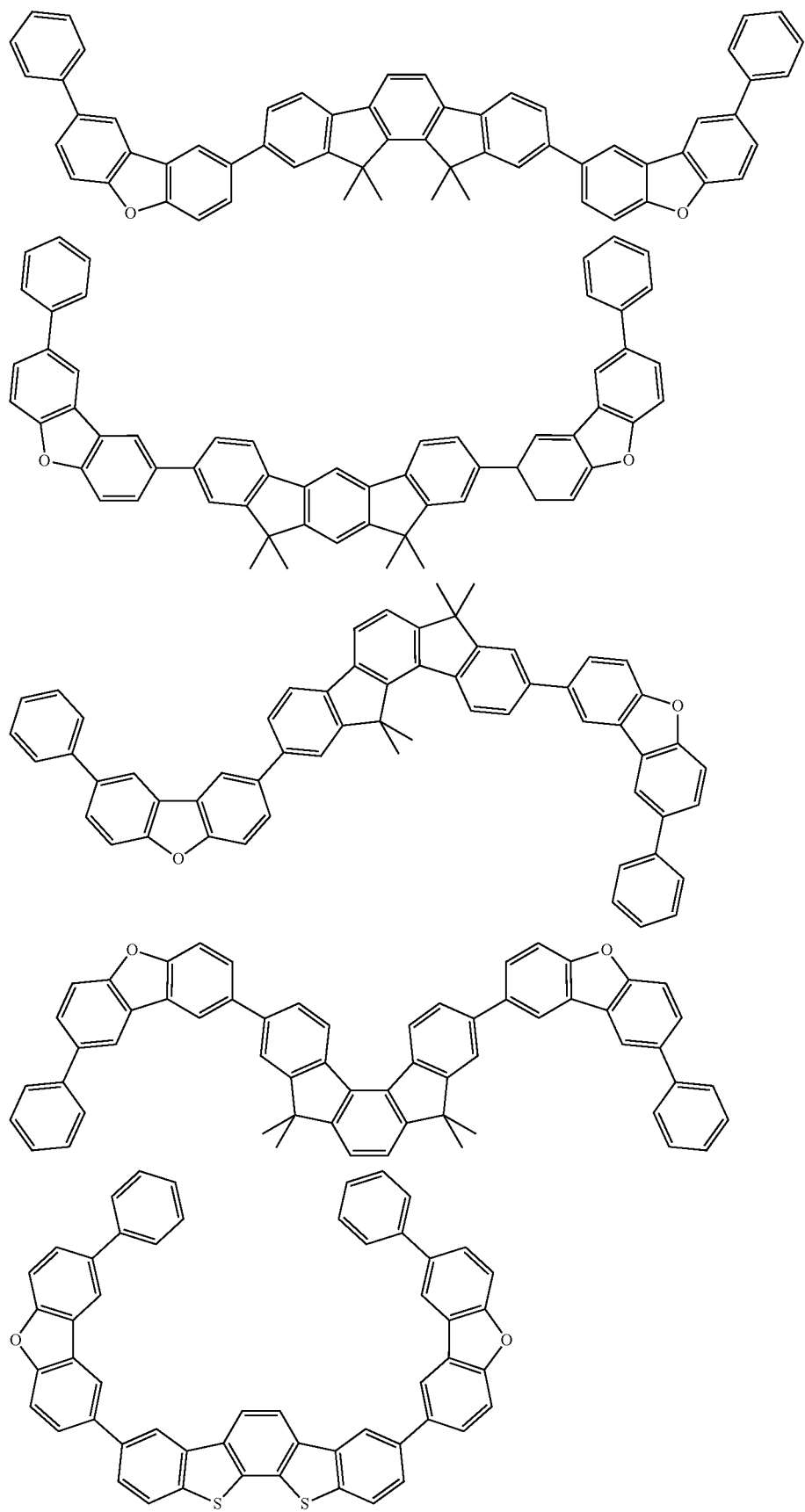

-continued
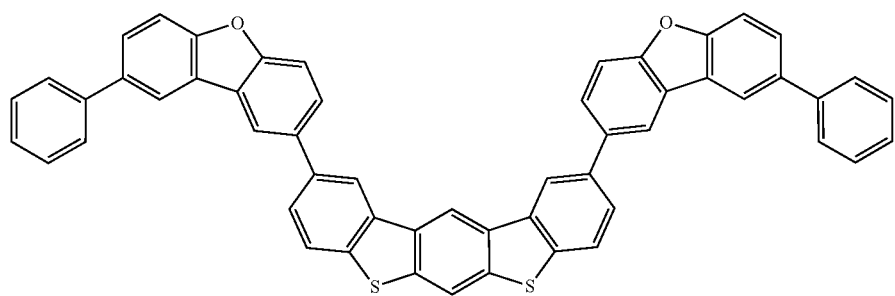
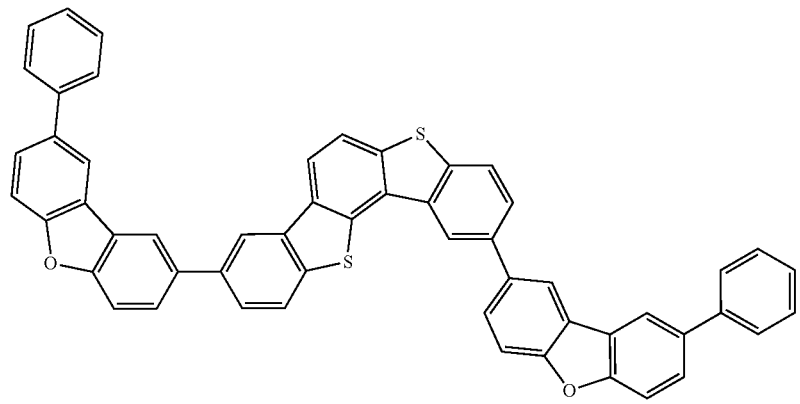
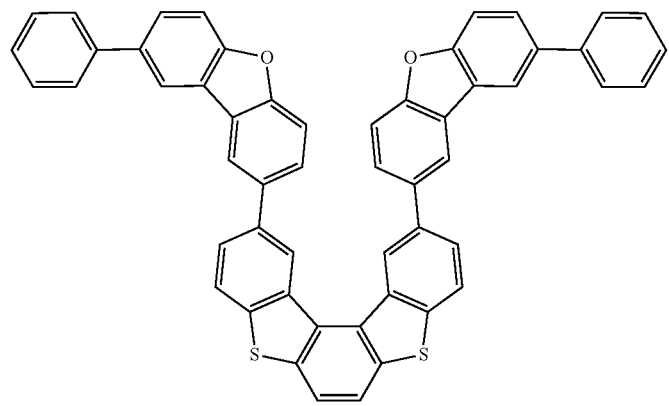

-continued
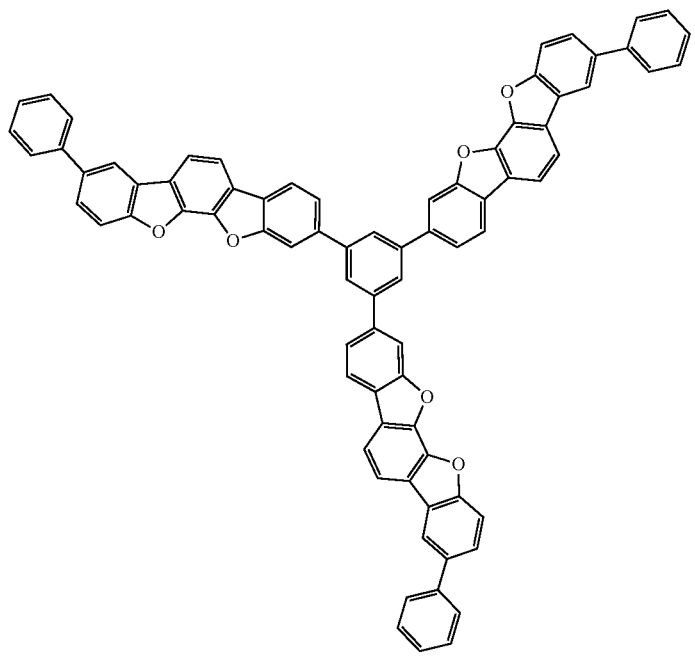
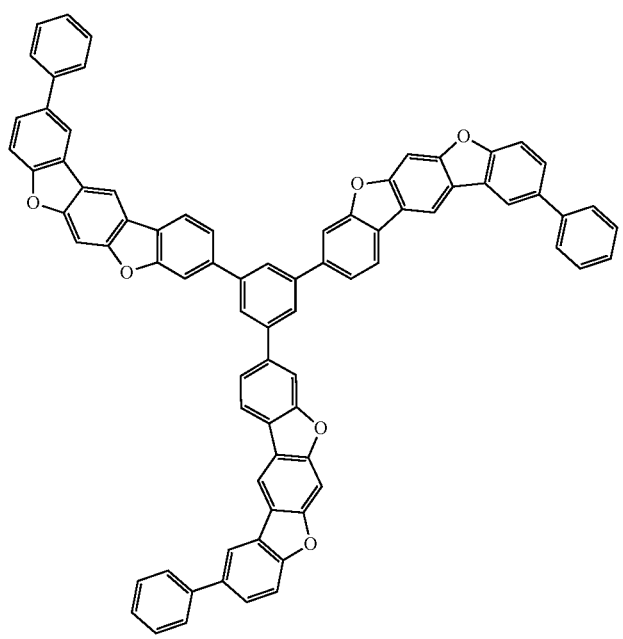

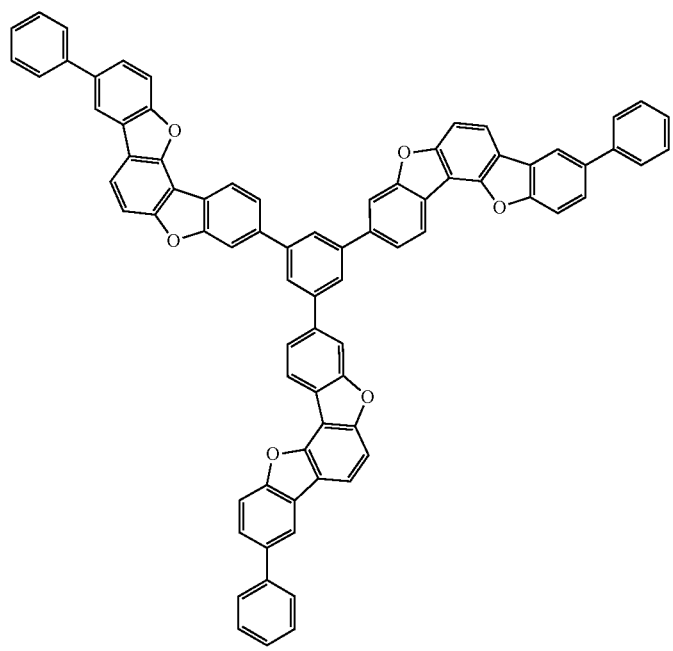
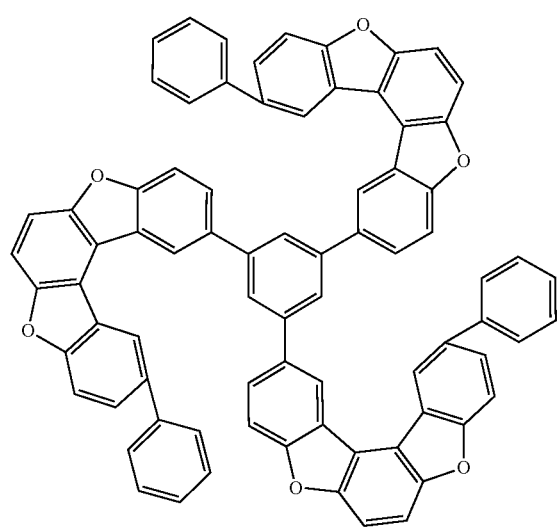
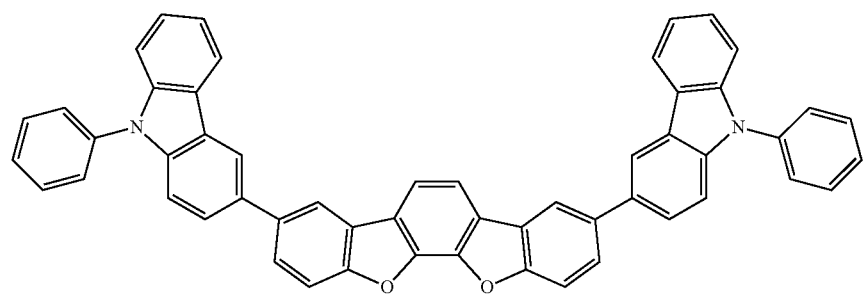

-continued
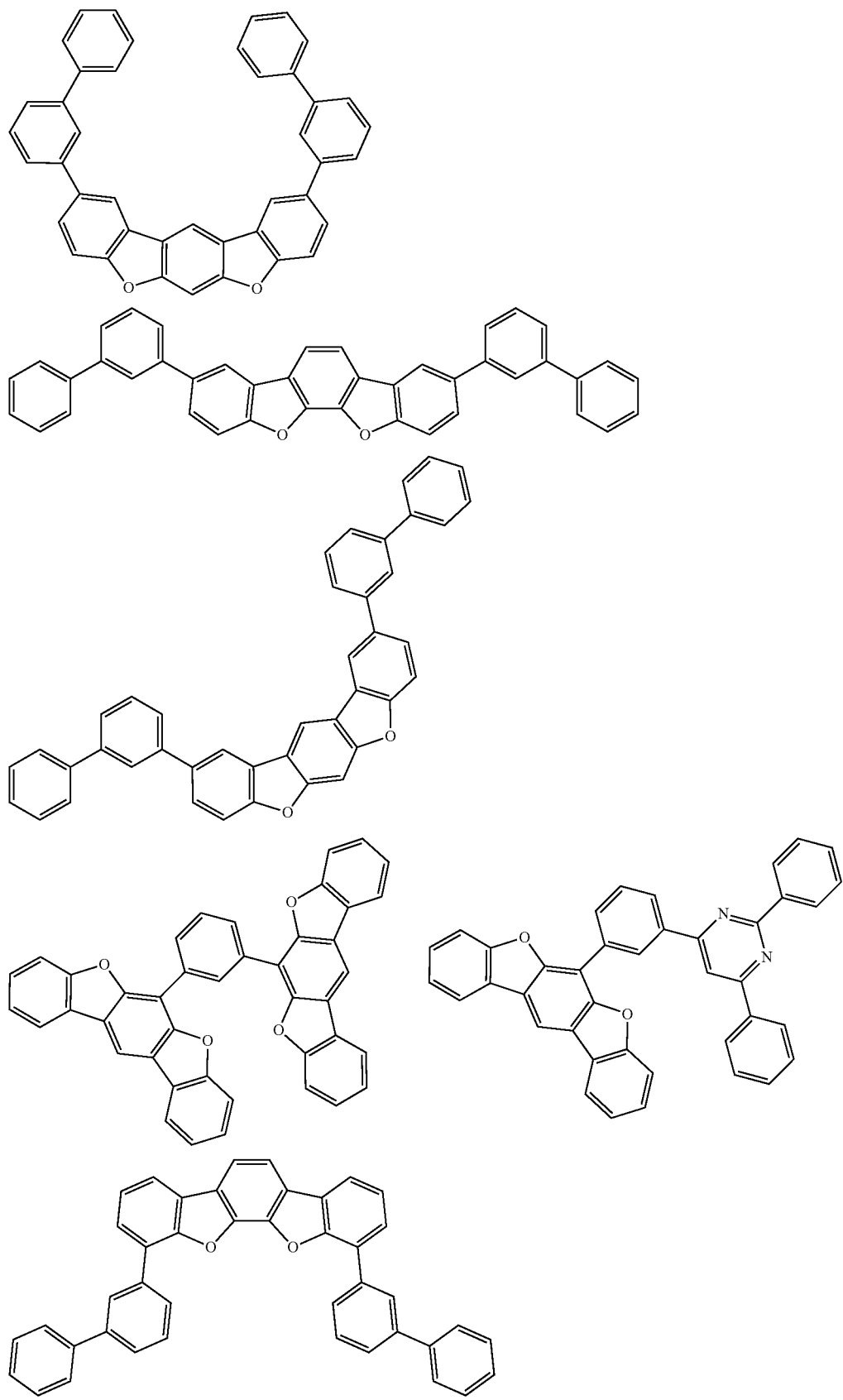

-continued
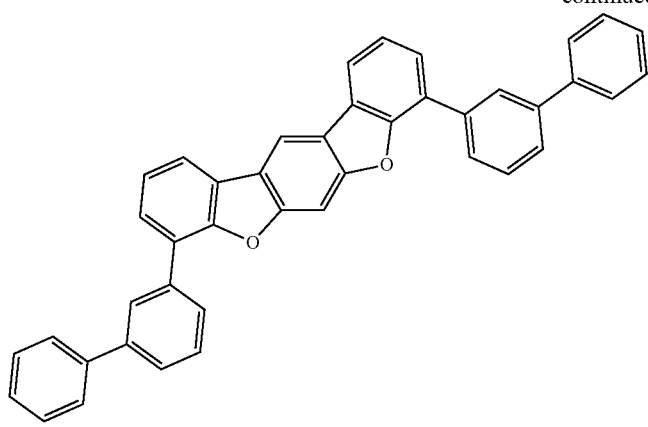
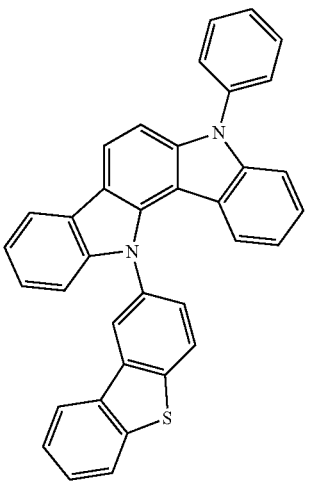
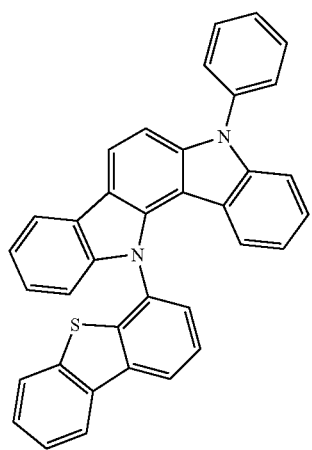
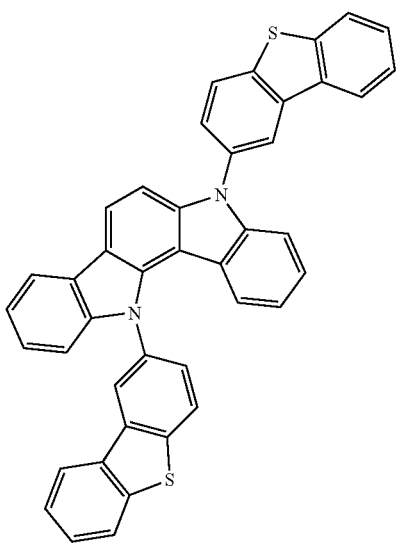
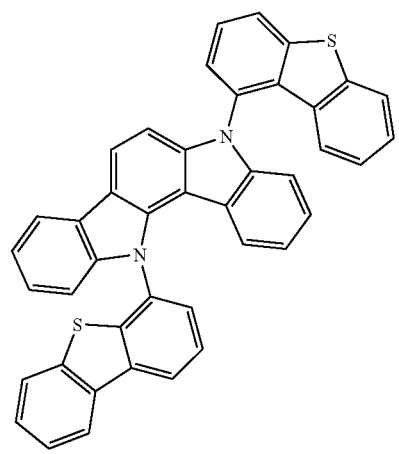
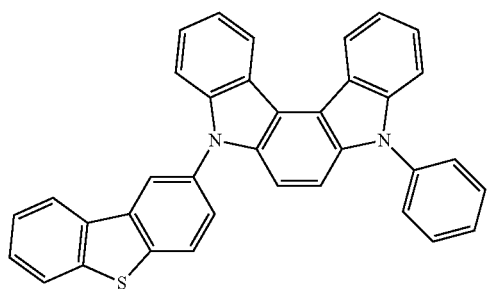
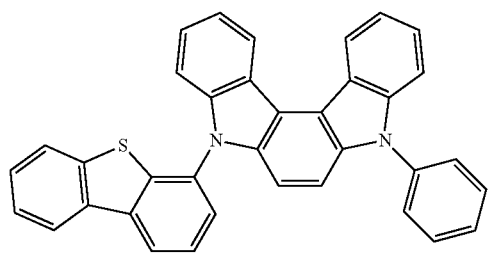
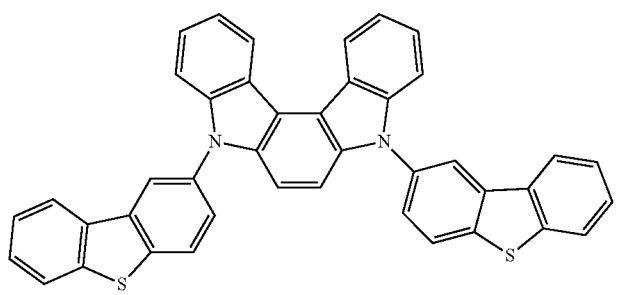

-continued
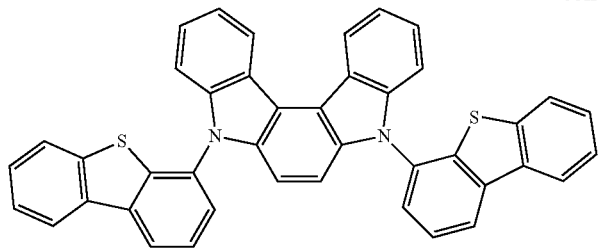
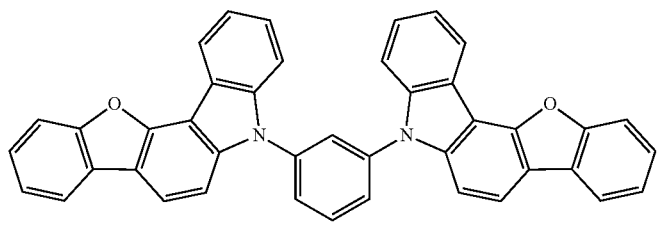
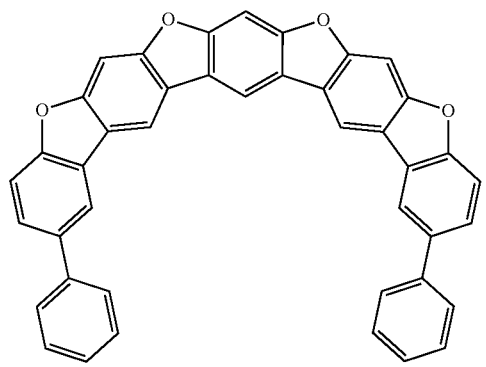
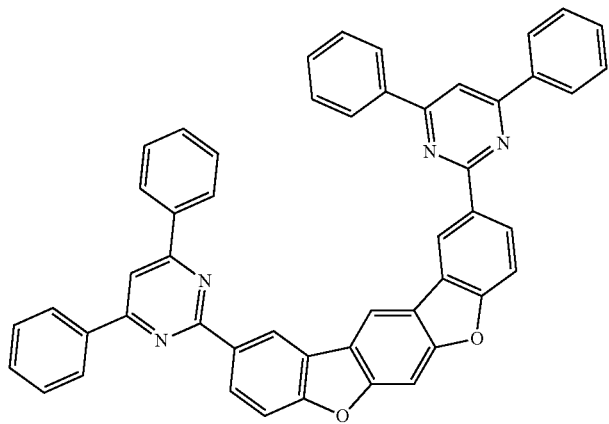
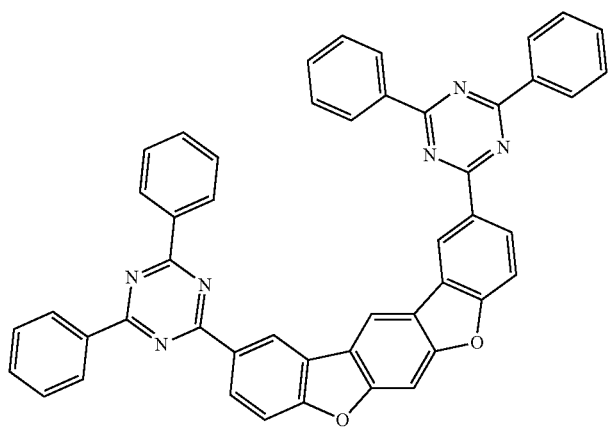

-continued
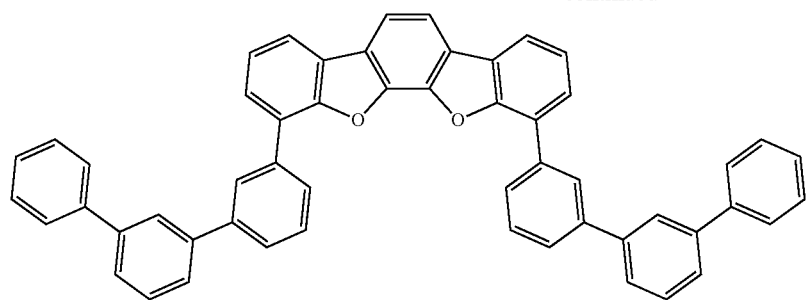
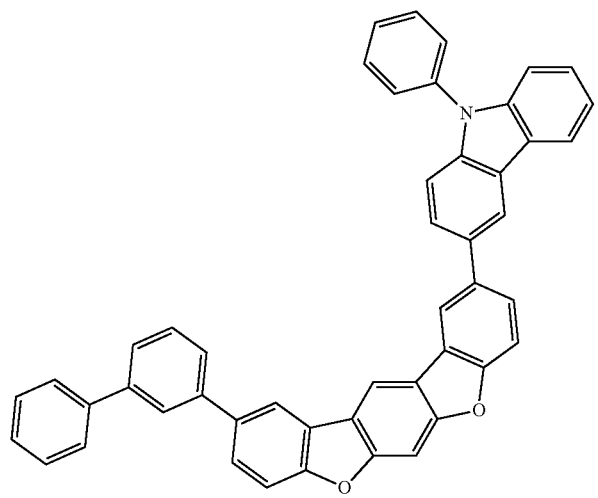
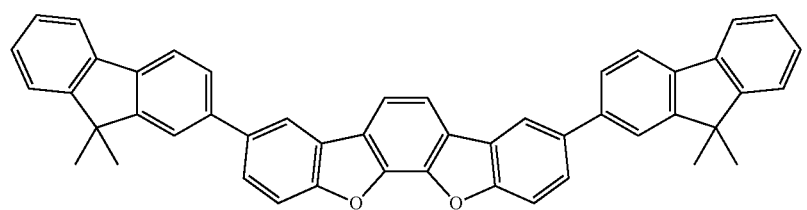
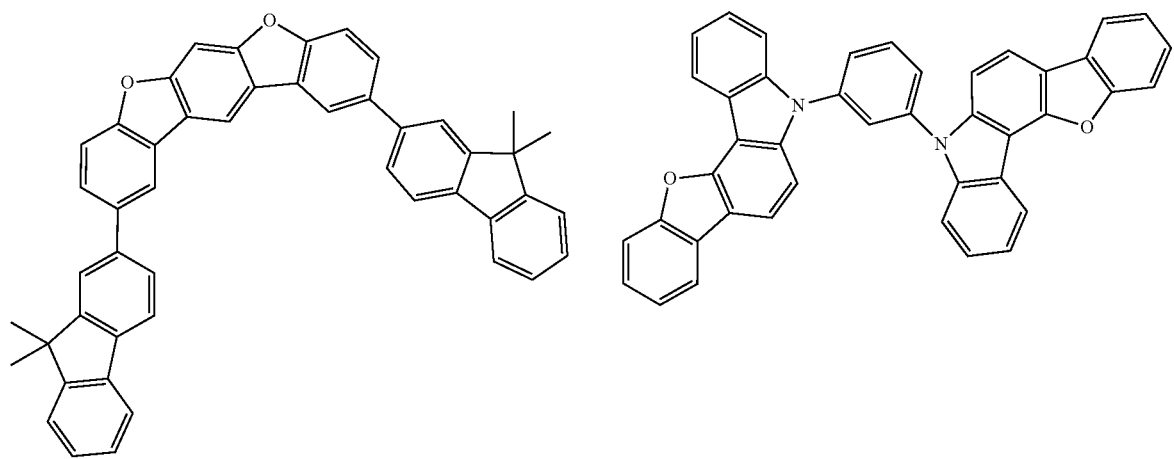

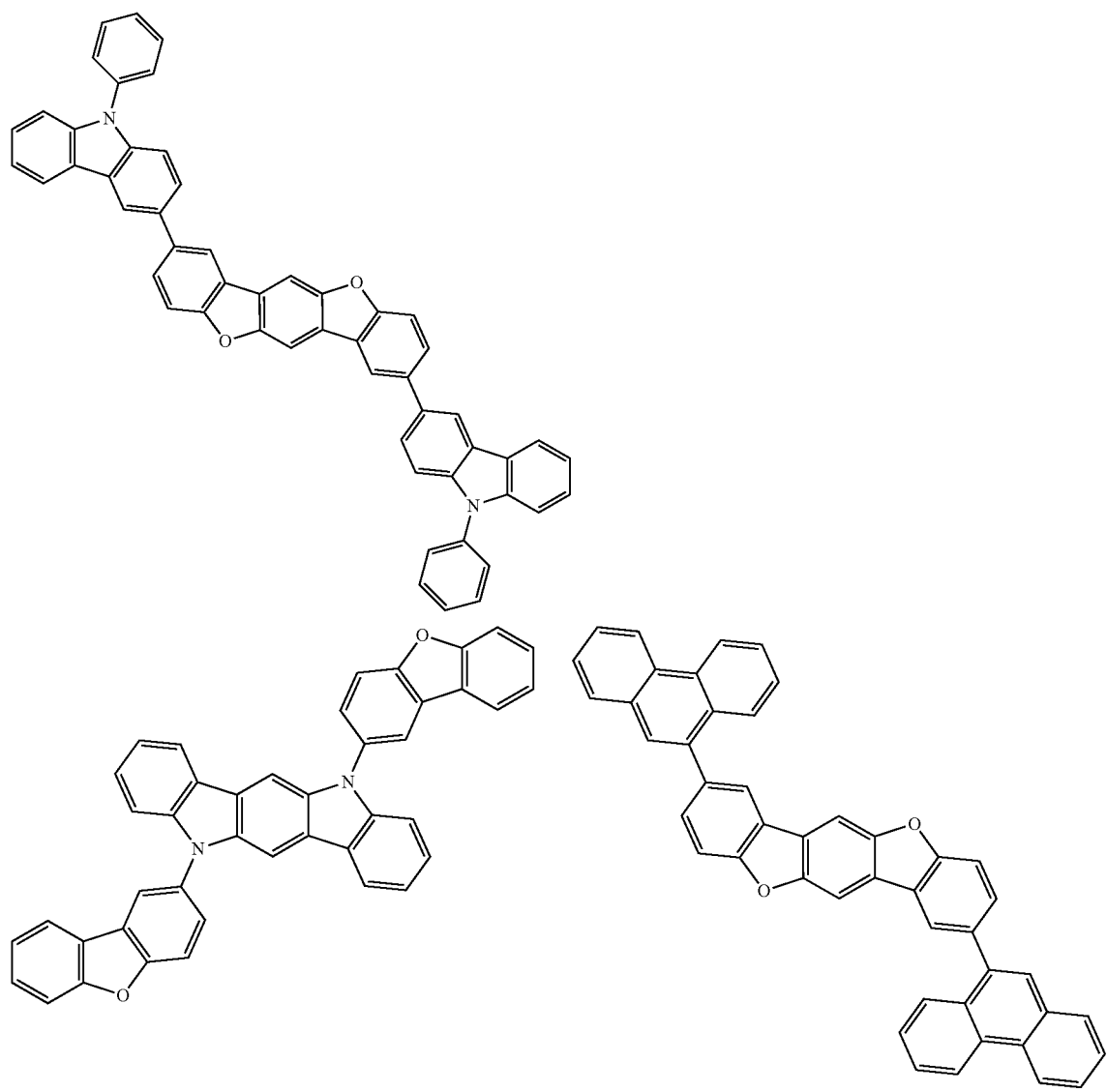
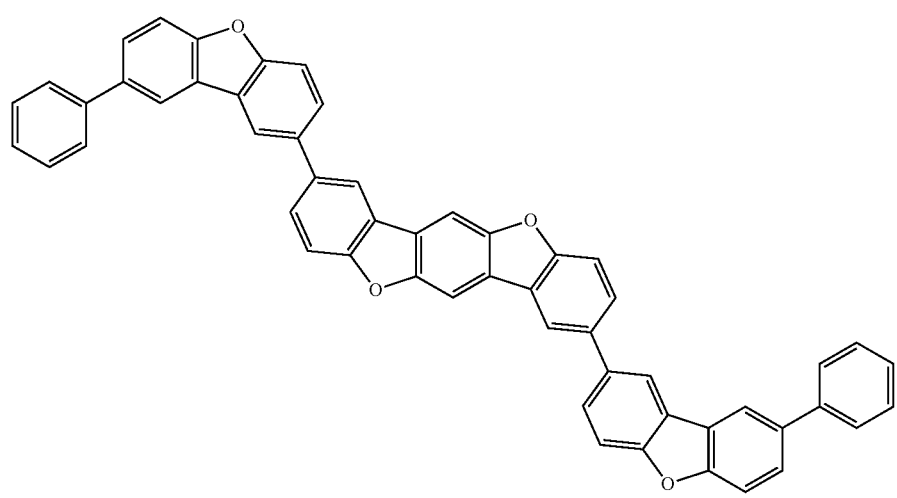

-continued
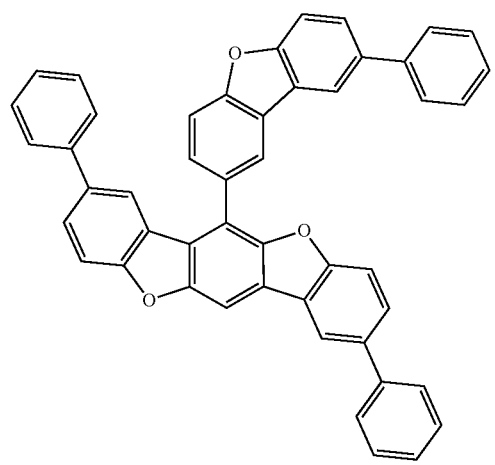
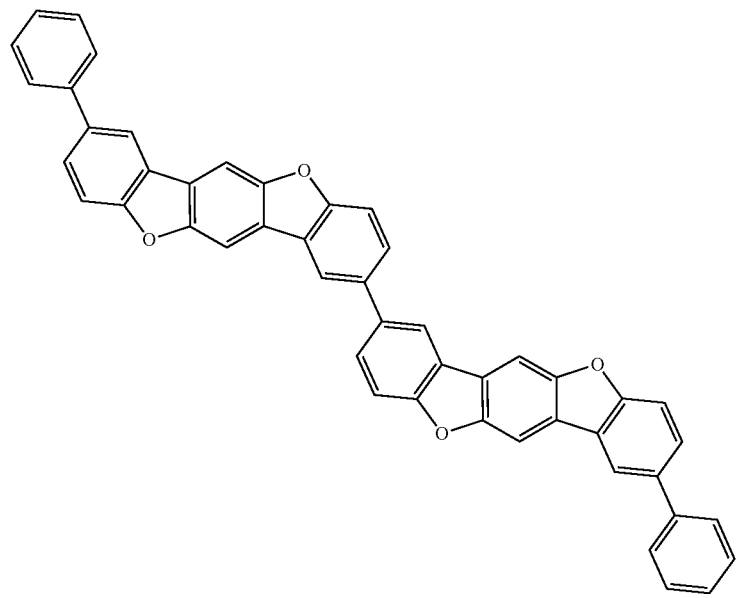
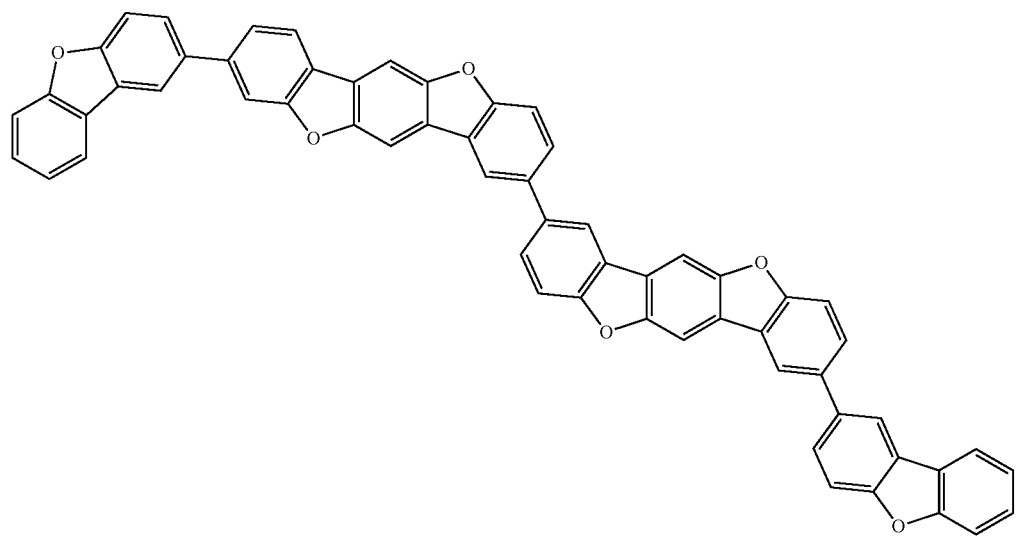

-continued
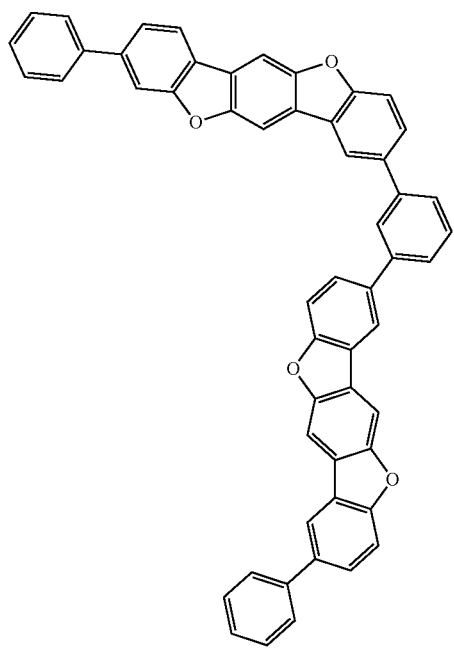
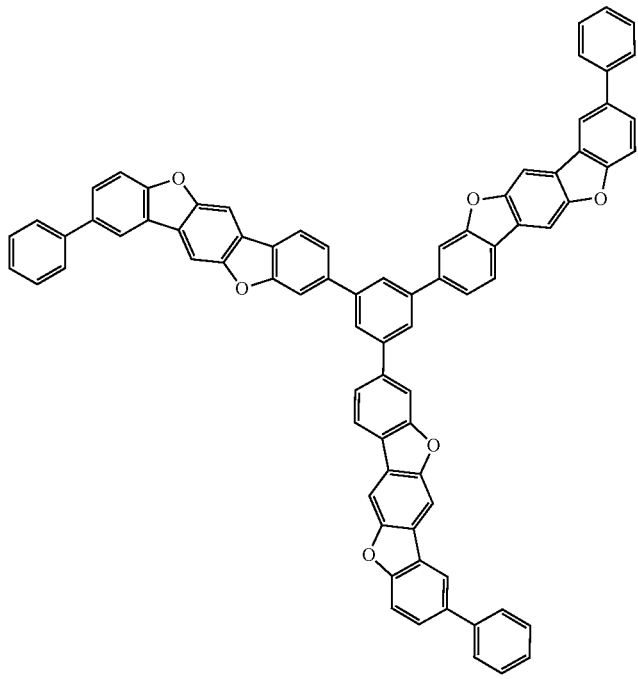

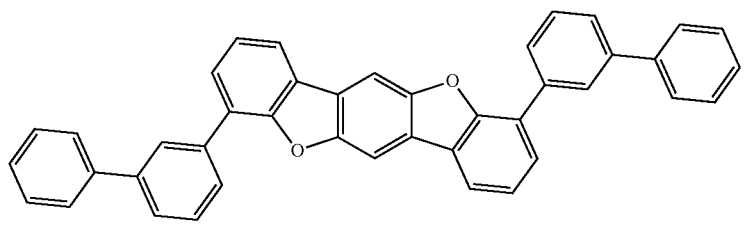
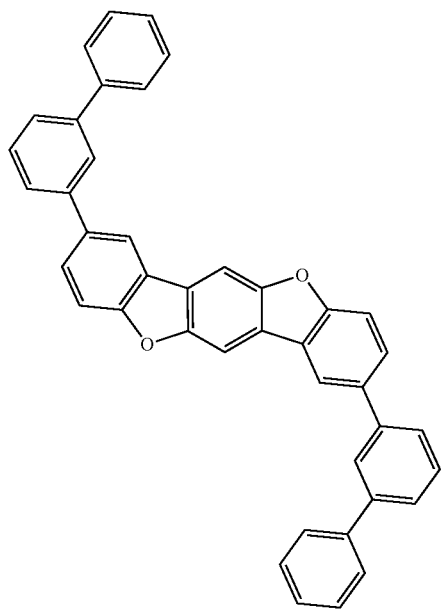
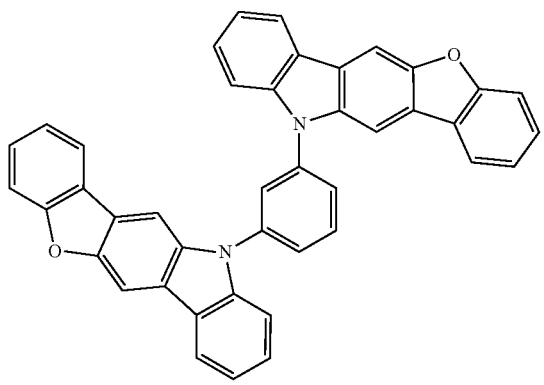
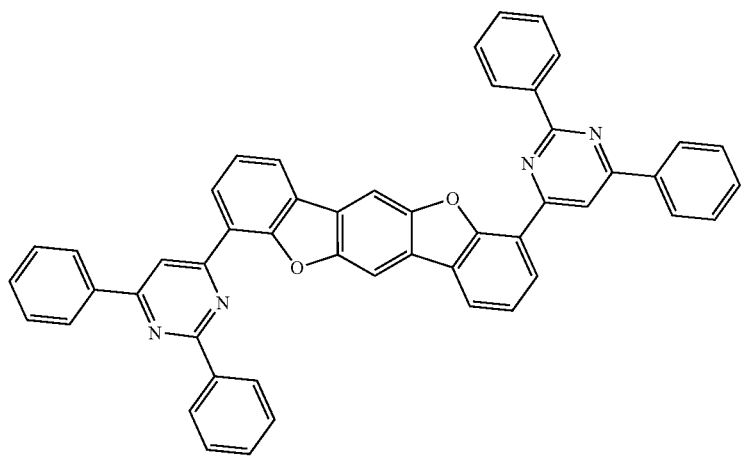

-continued
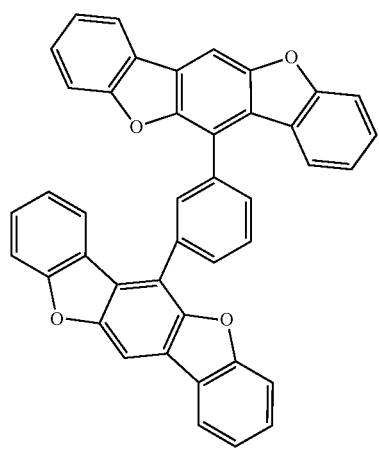
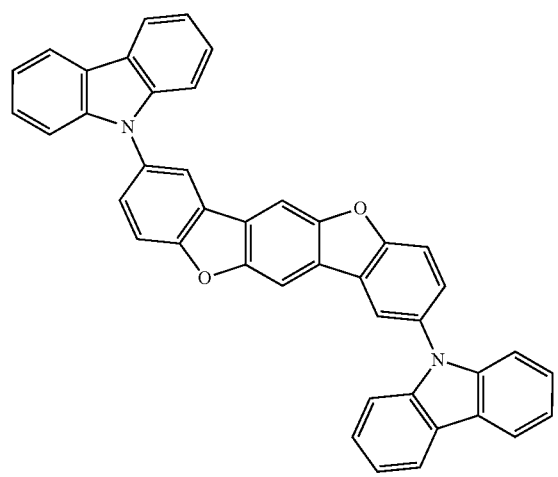
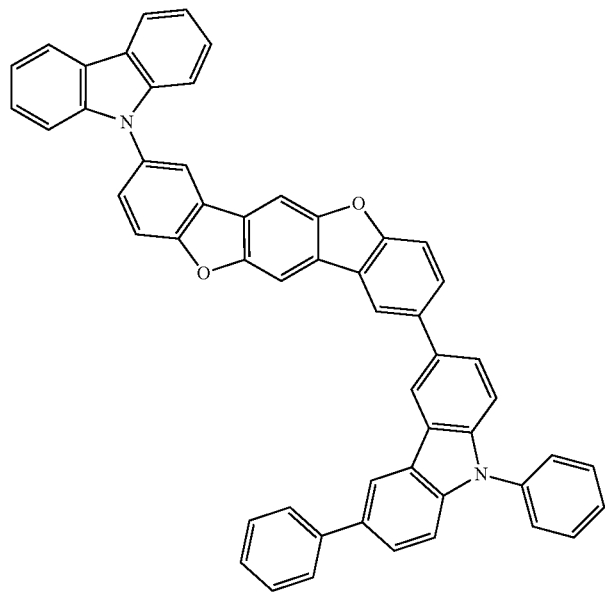
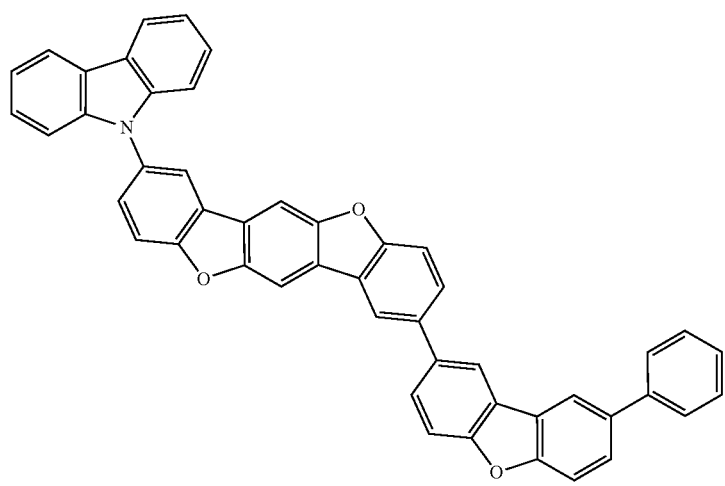

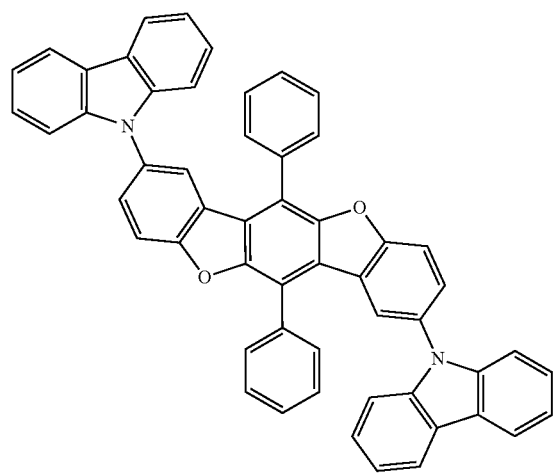
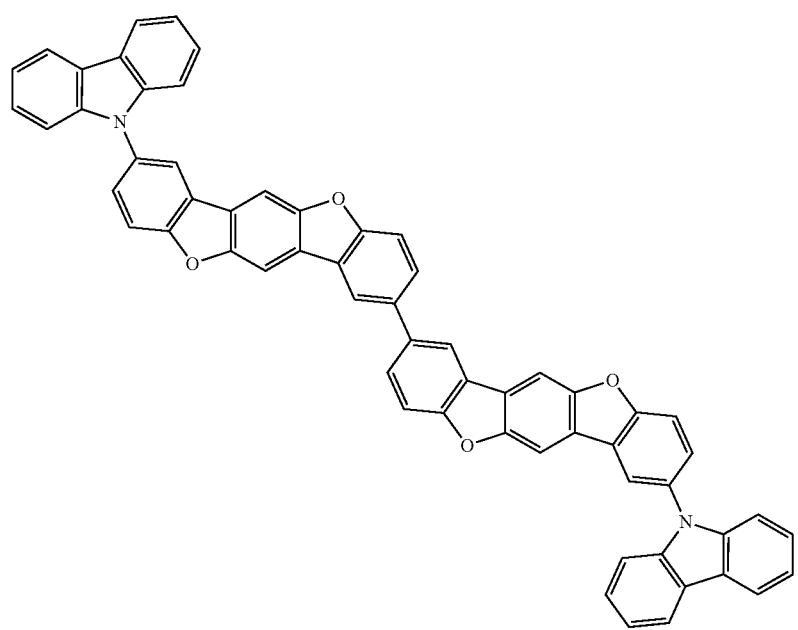

-continued
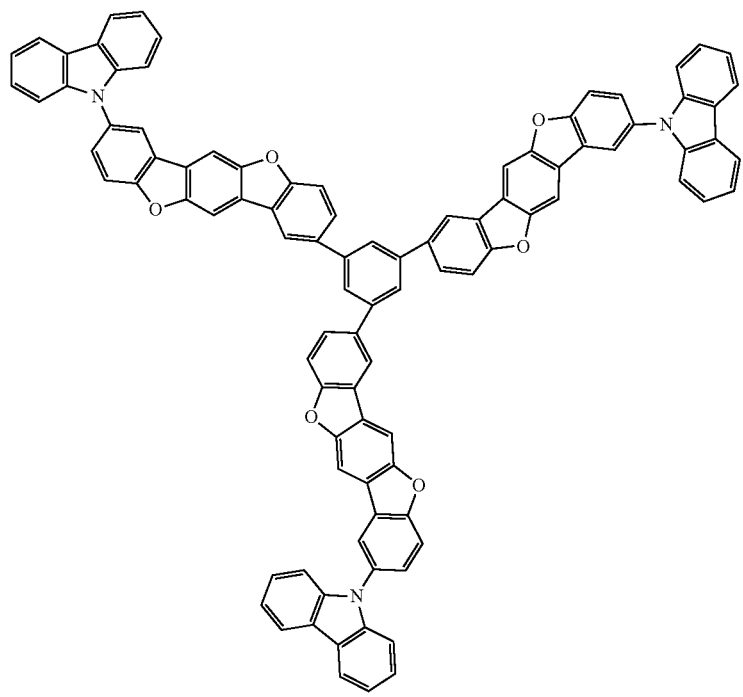
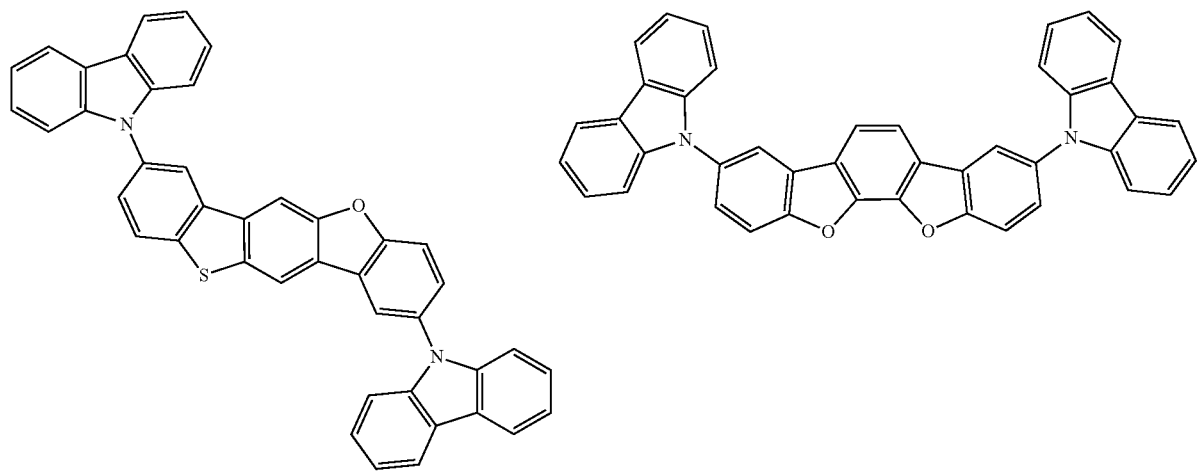
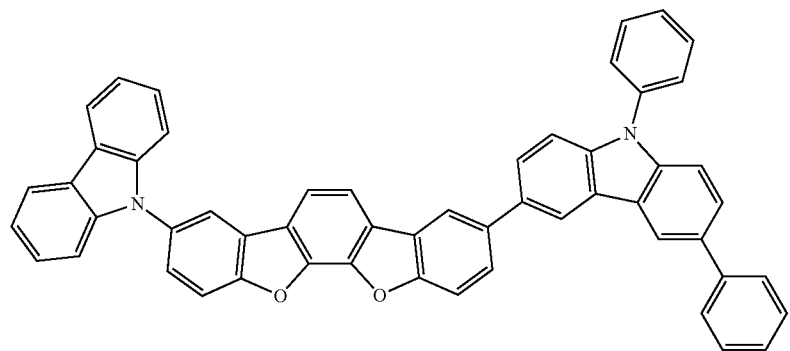

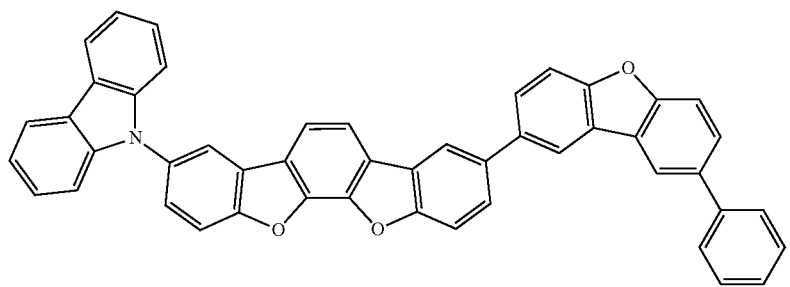
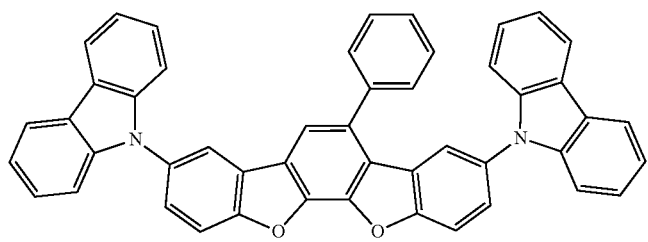
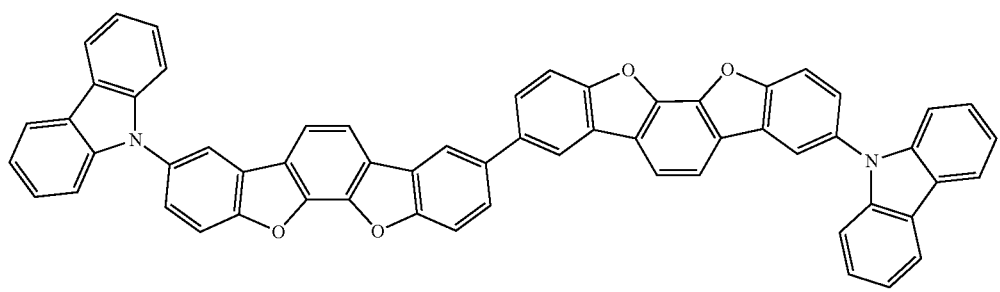
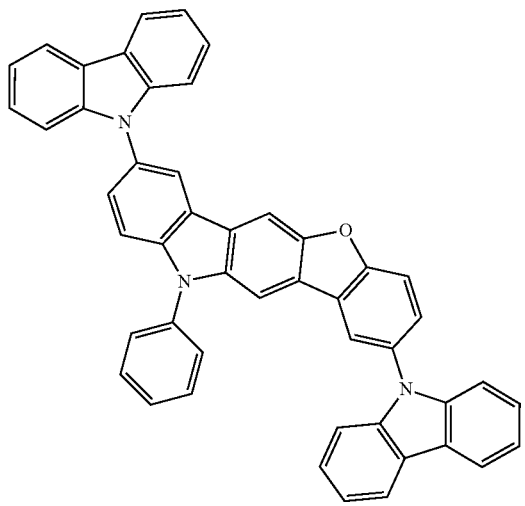

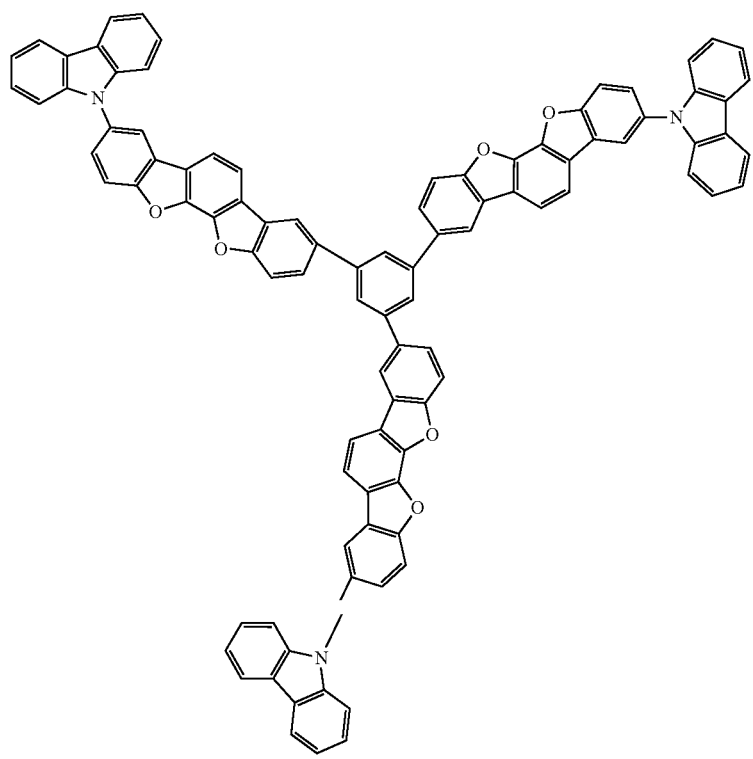
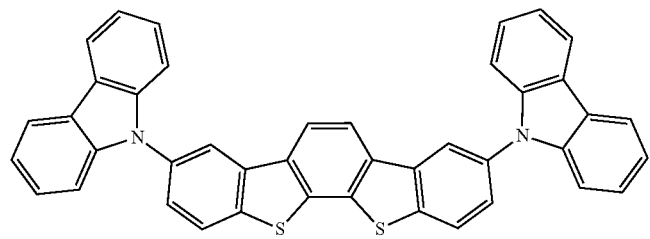
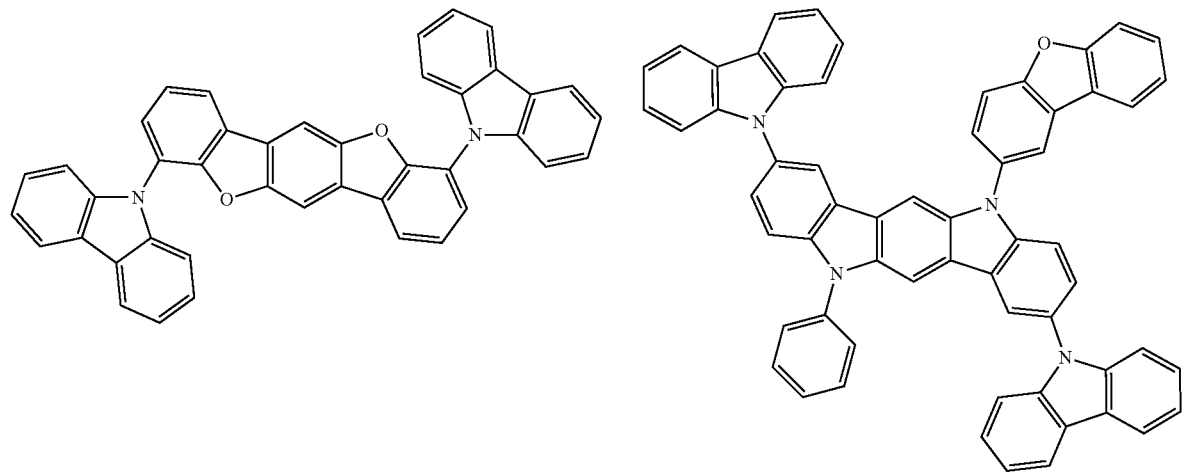

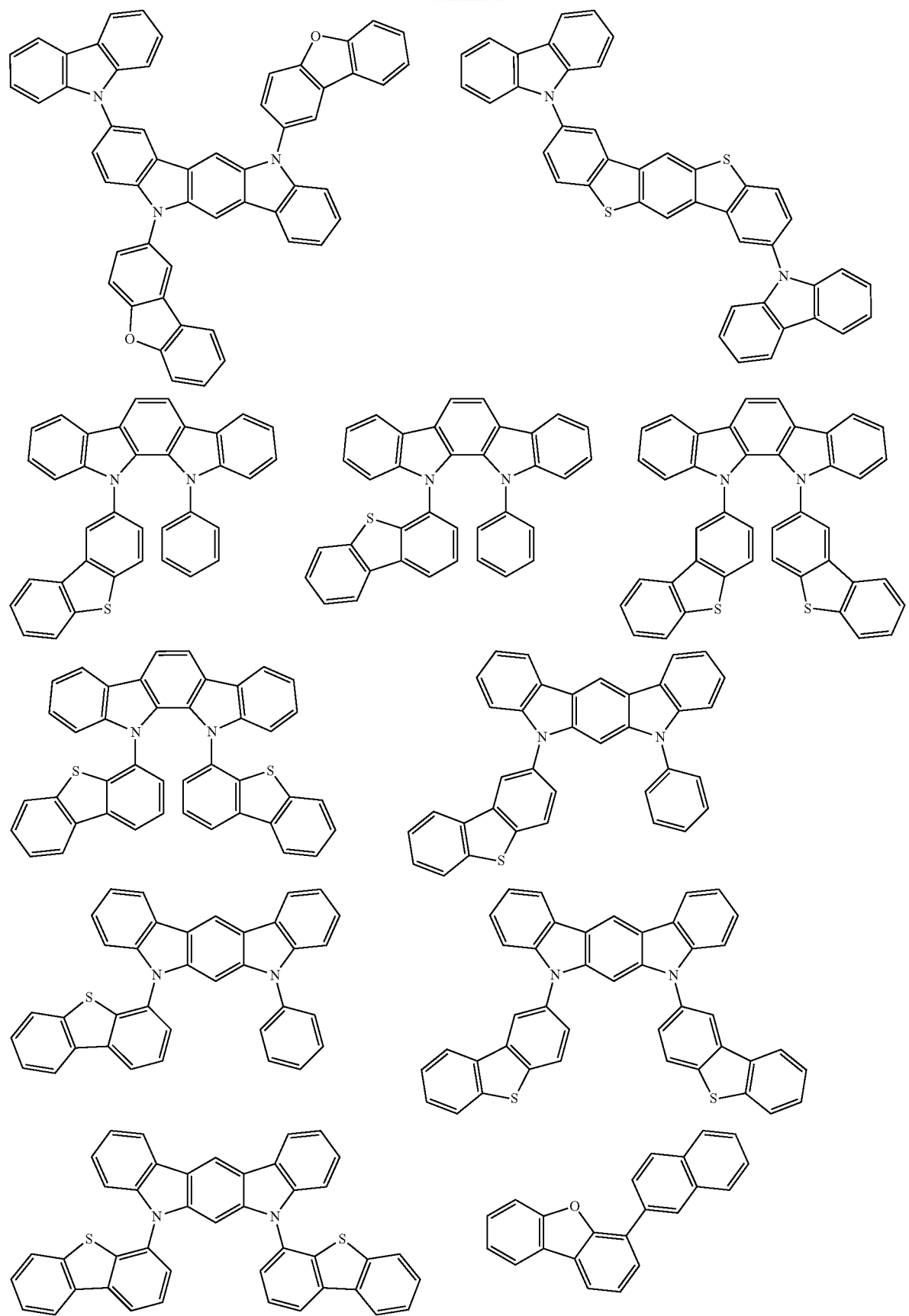

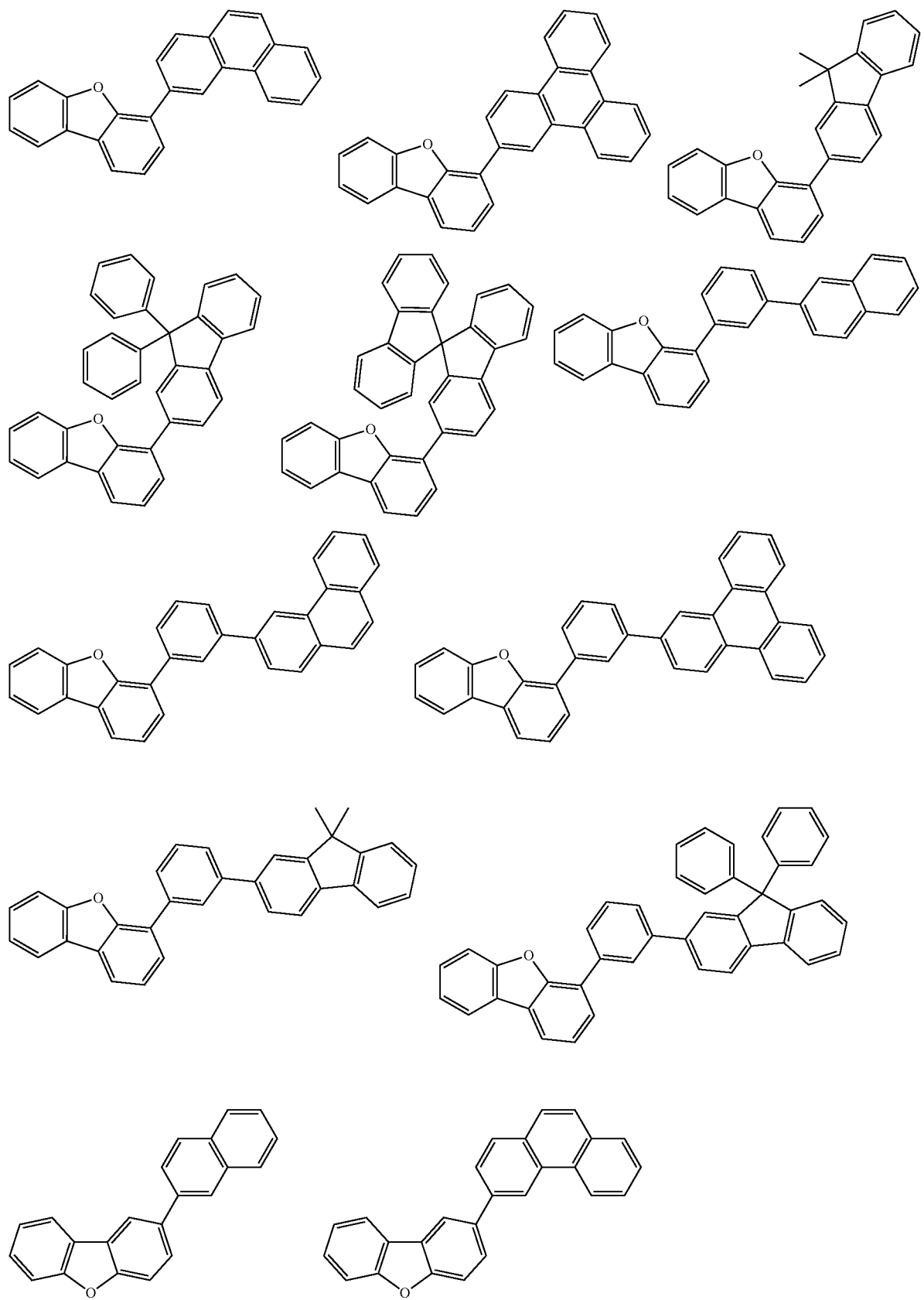

-continued
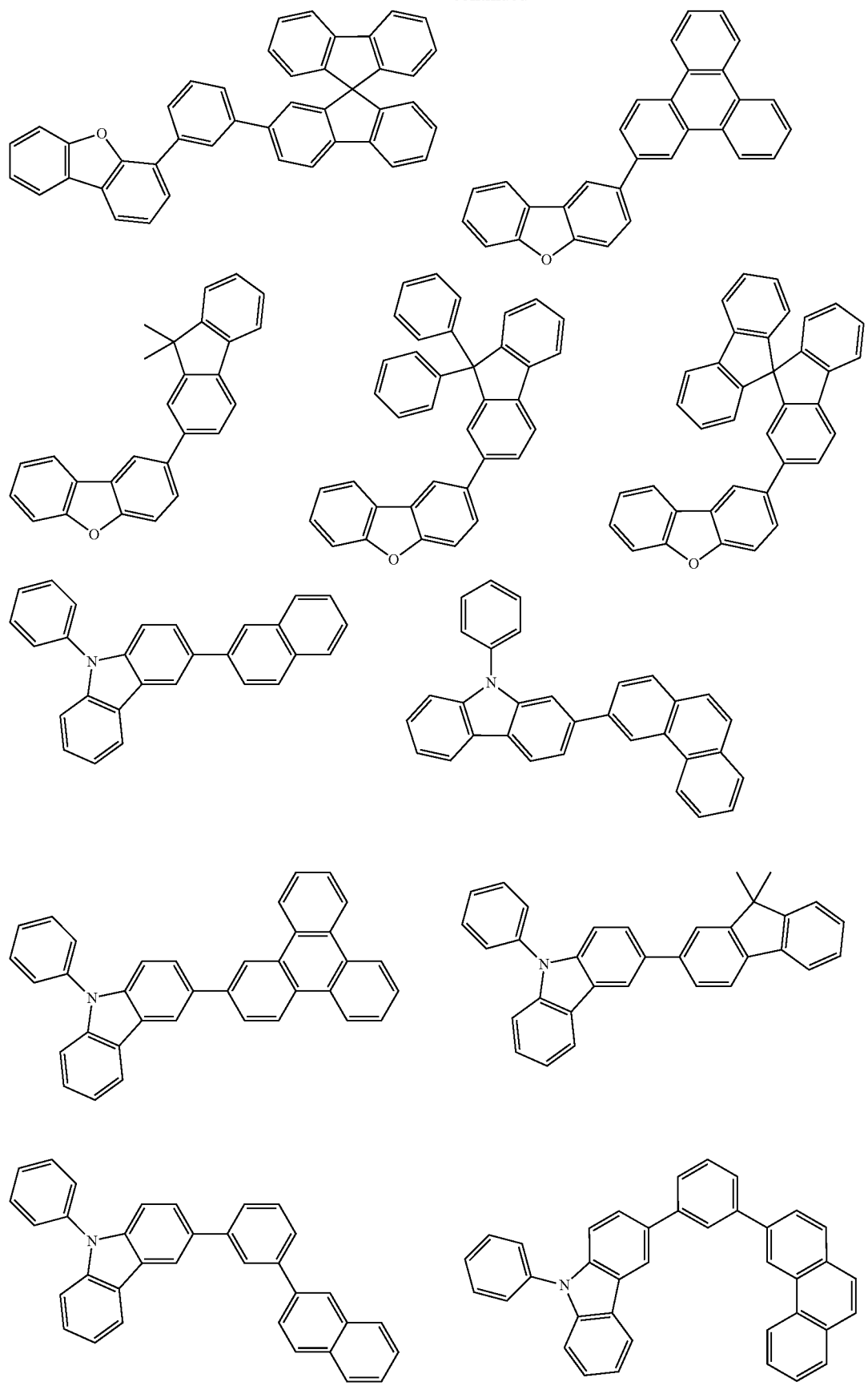

-continued
75
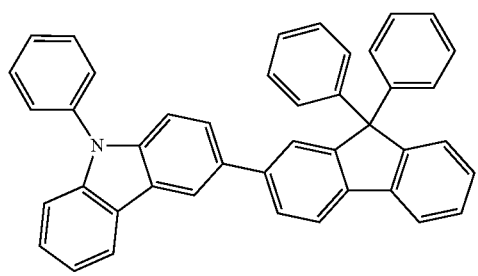
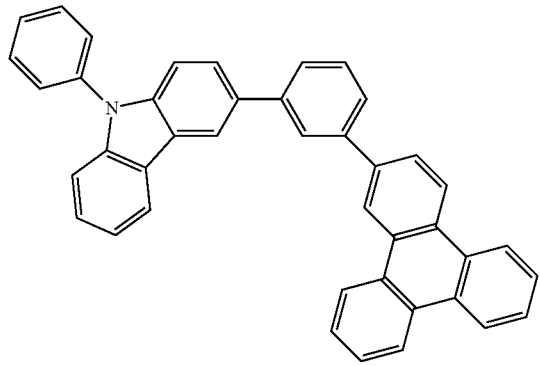
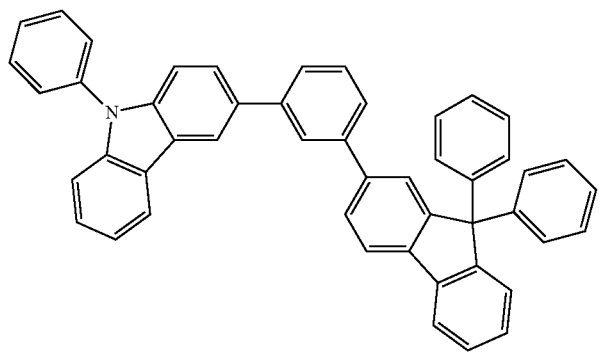
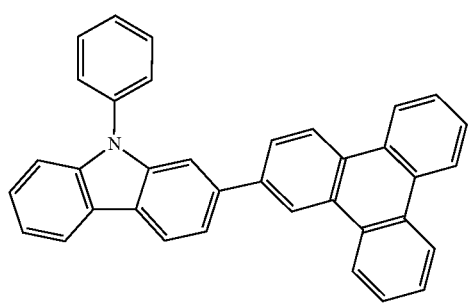
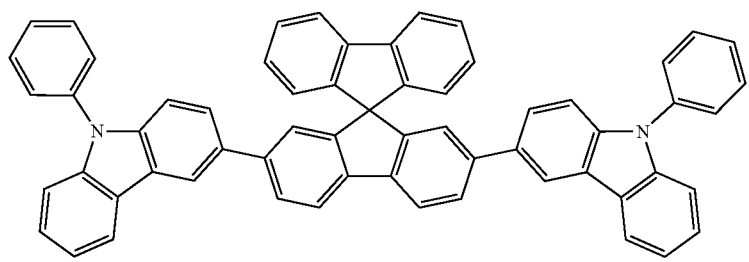
76
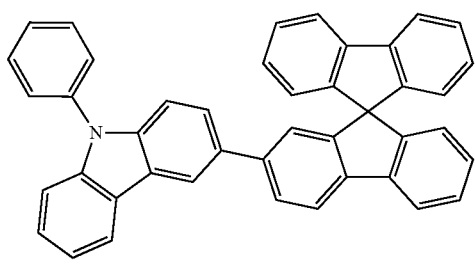
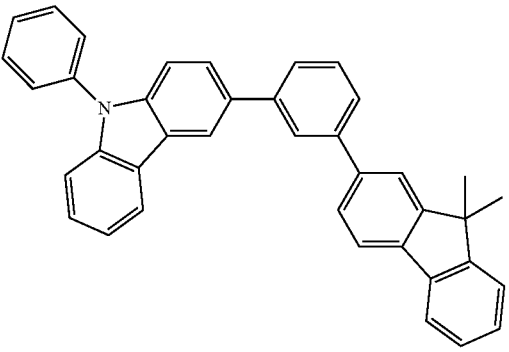
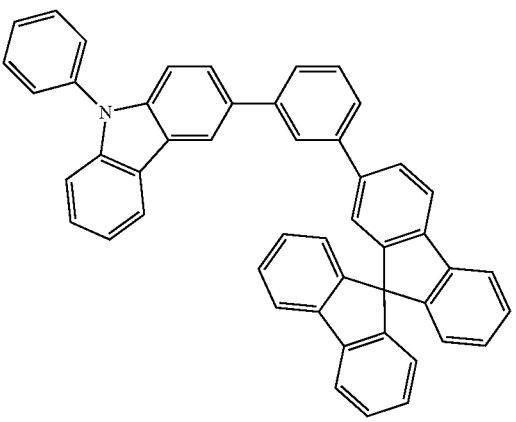

-continued
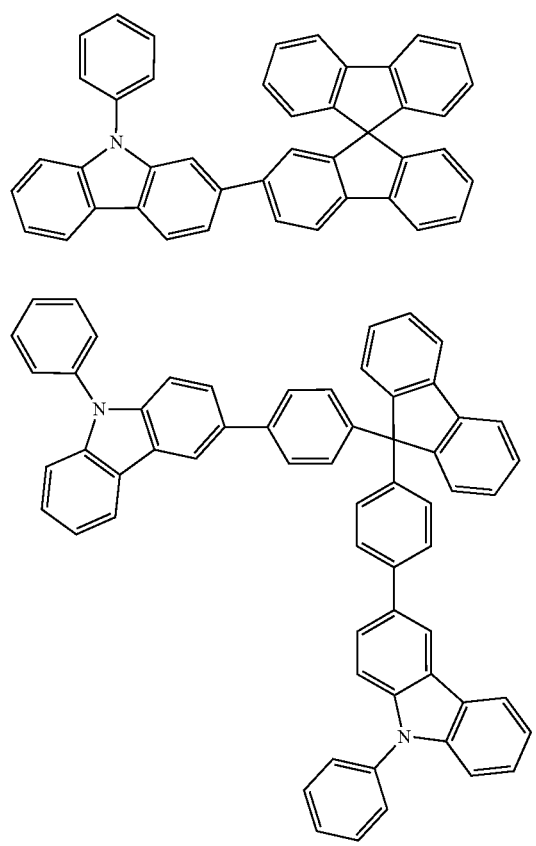
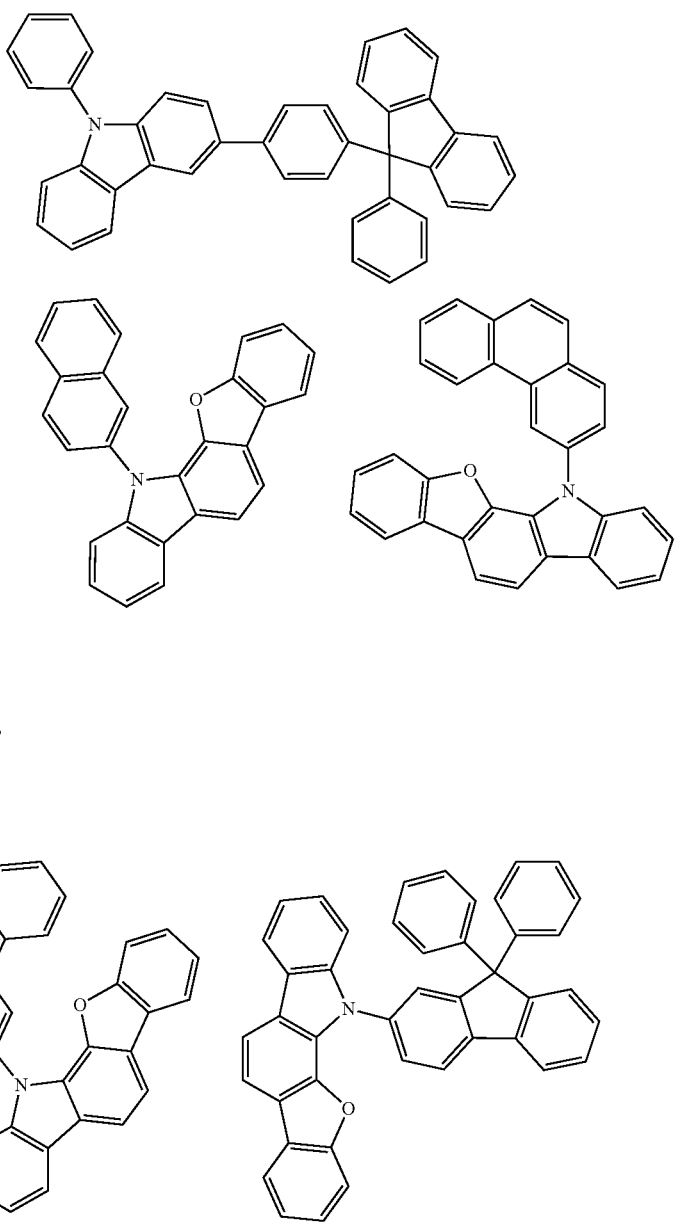
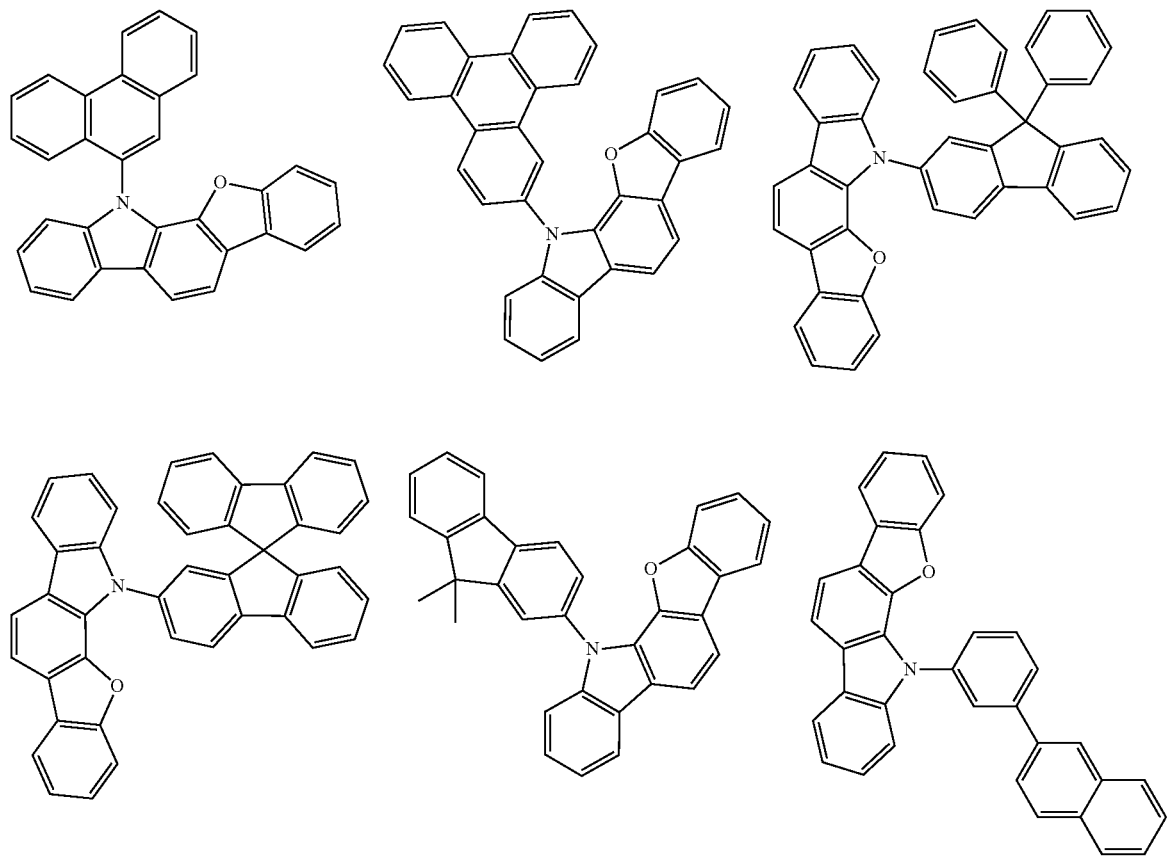

-continued
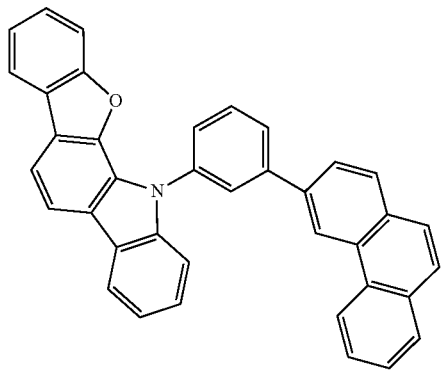
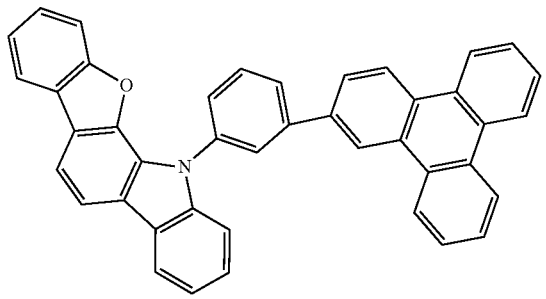
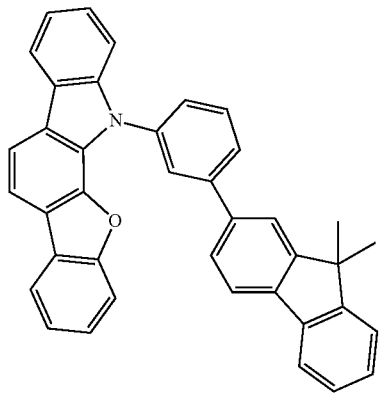
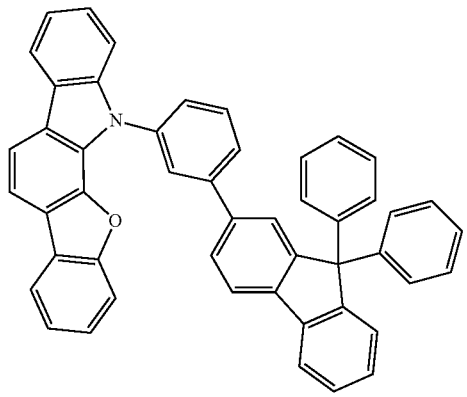
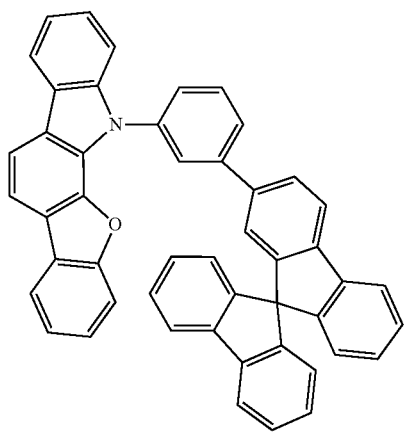
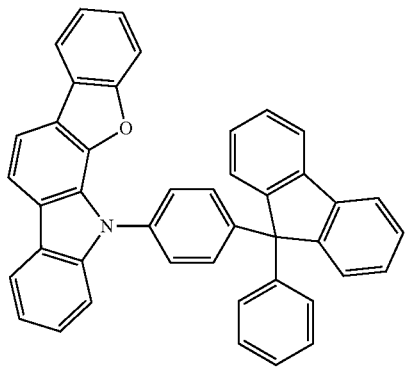
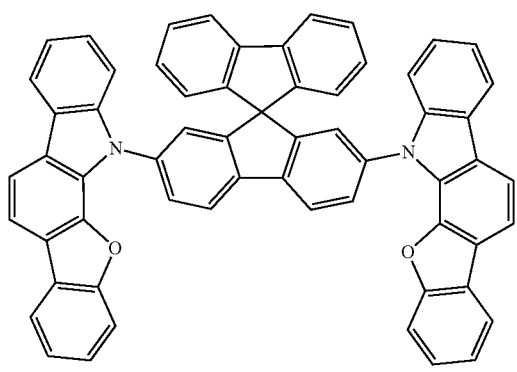
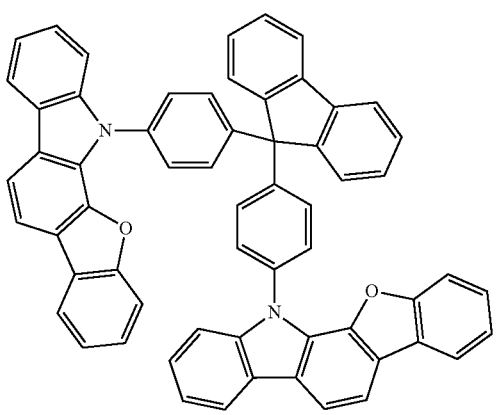

-continued
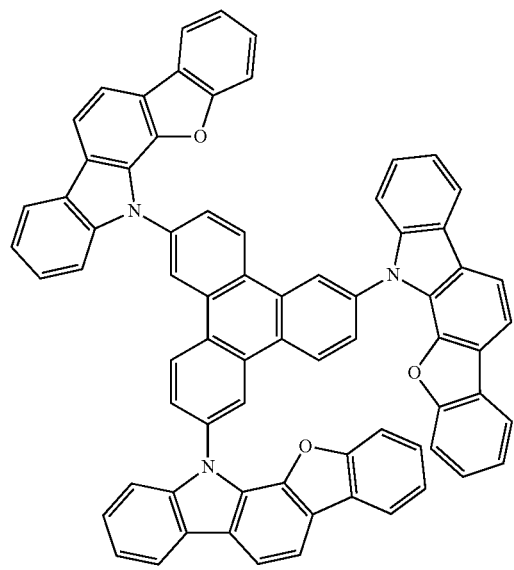
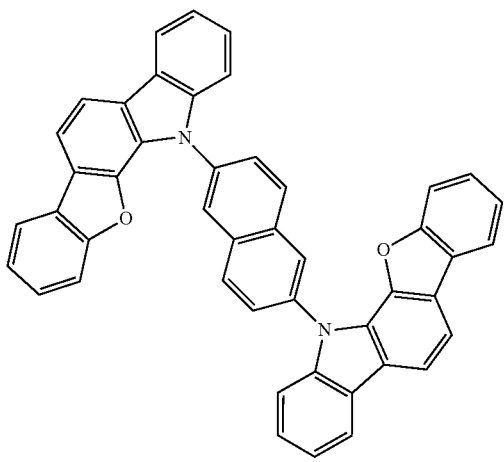
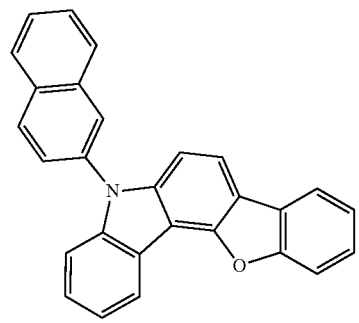
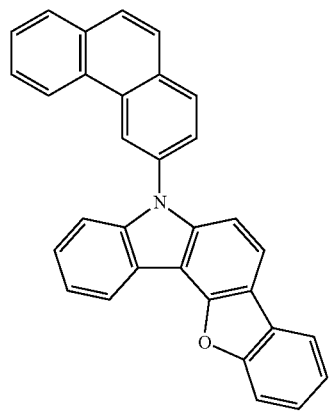
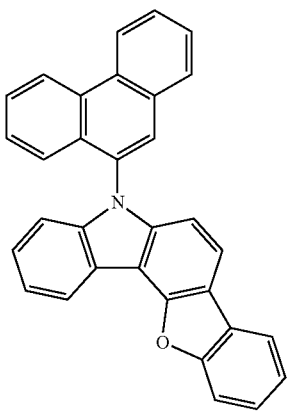
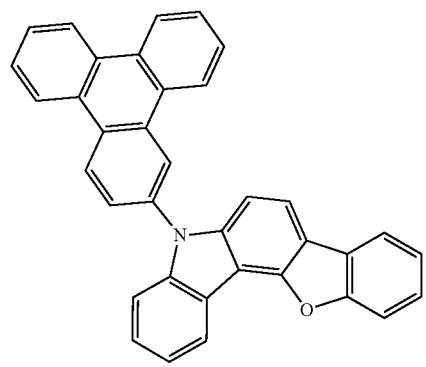
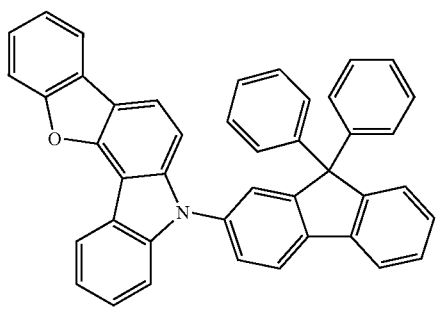
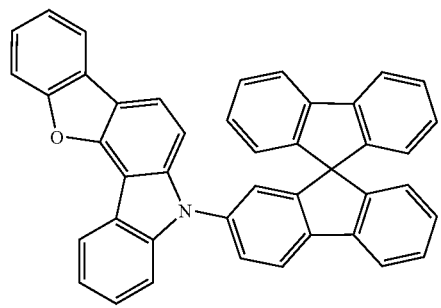
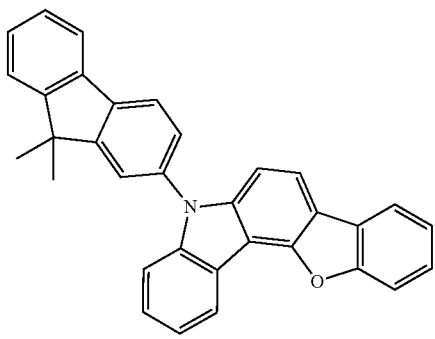

-continued
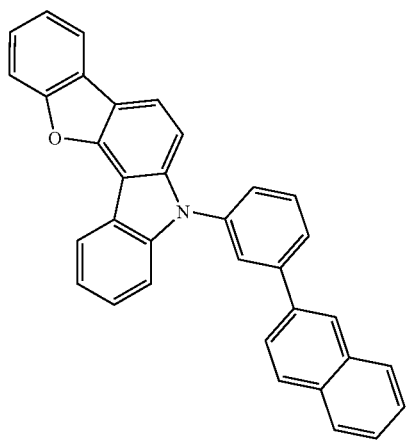
83
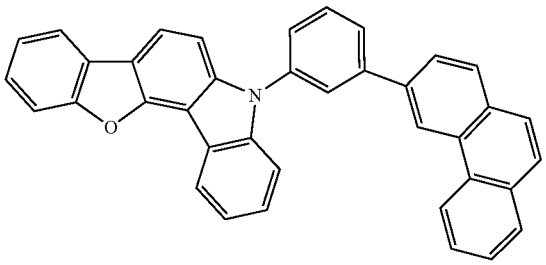
84
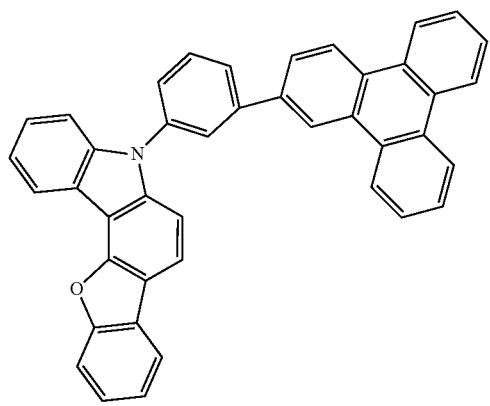
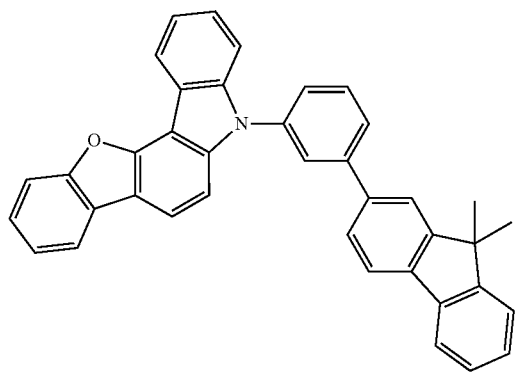
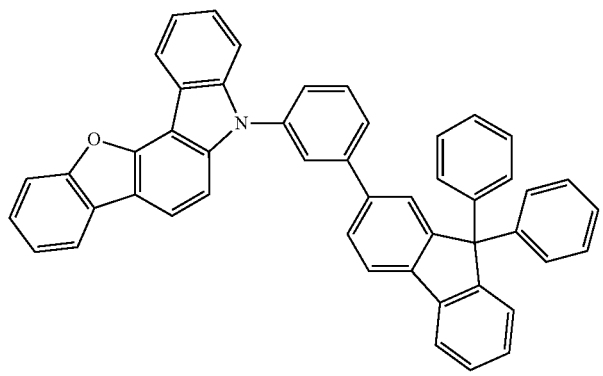
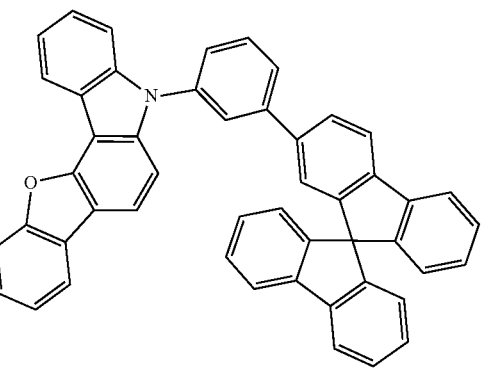
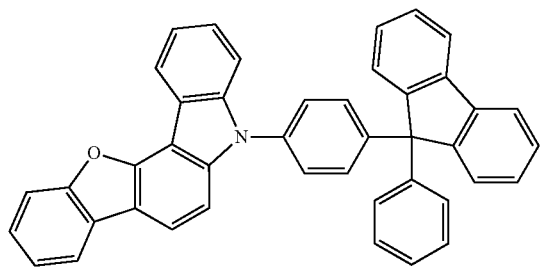

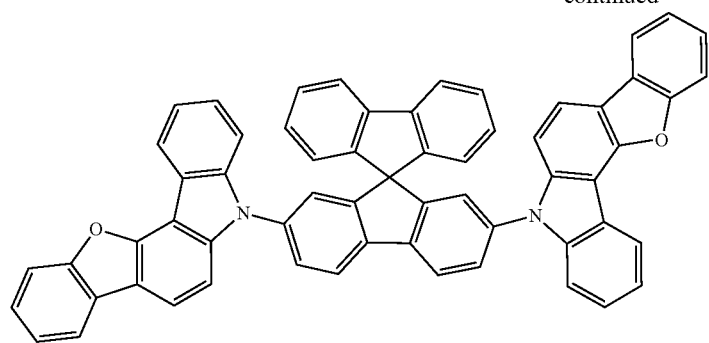
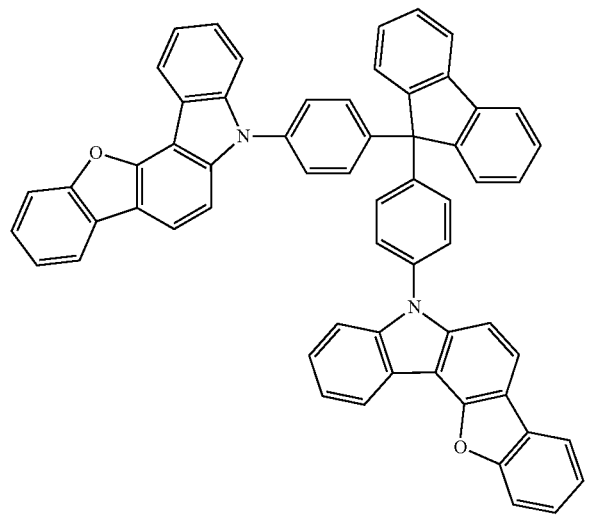
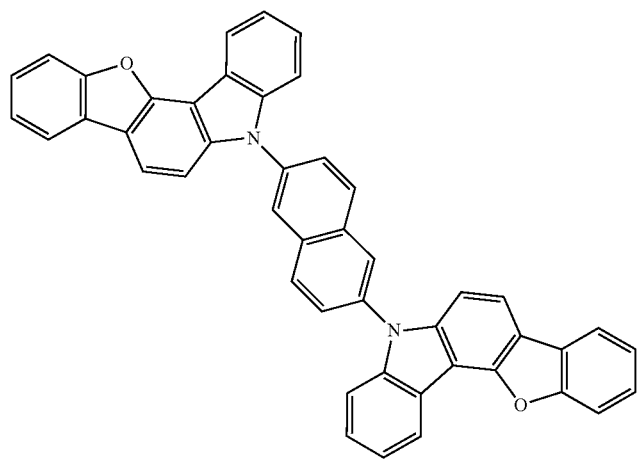
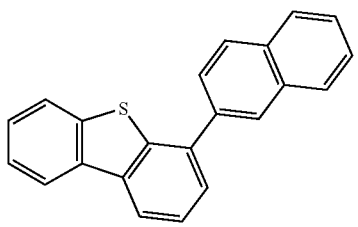
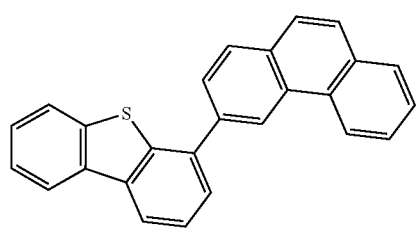
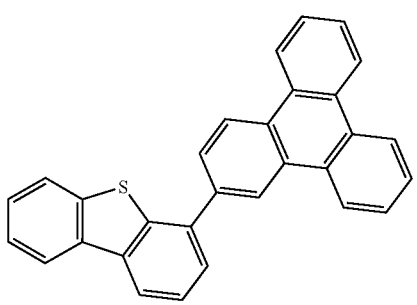
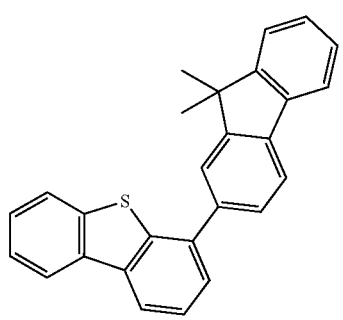

-continued
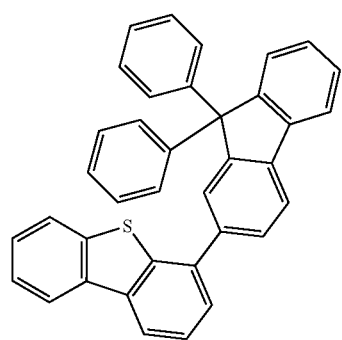
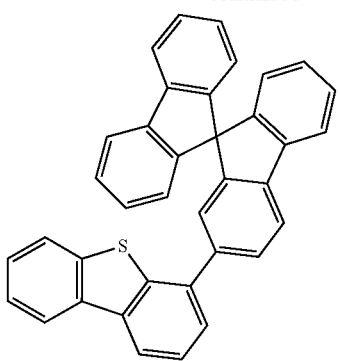
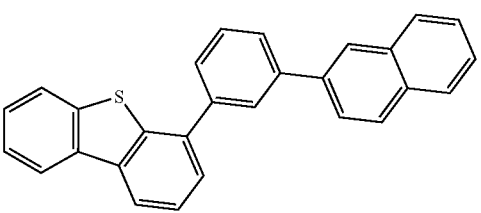
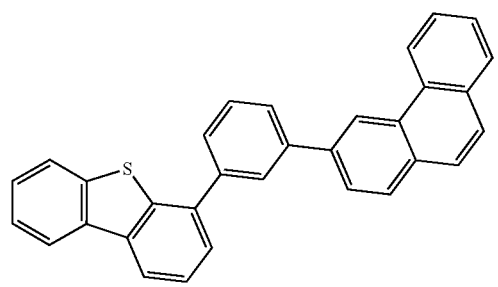
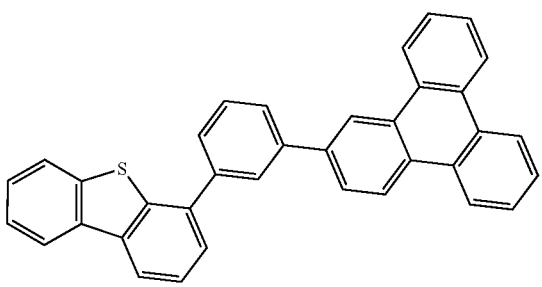
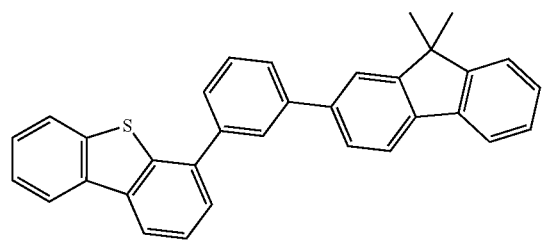
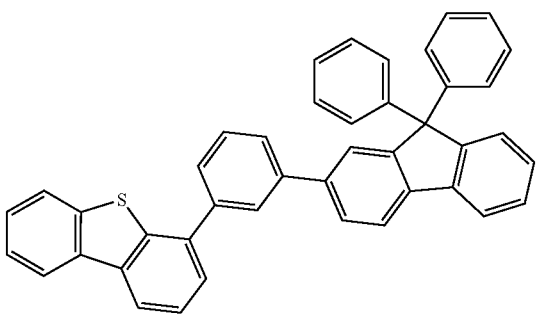
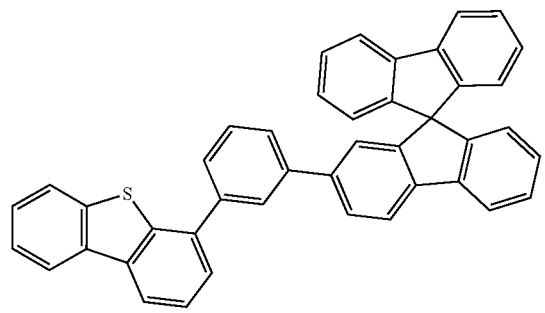
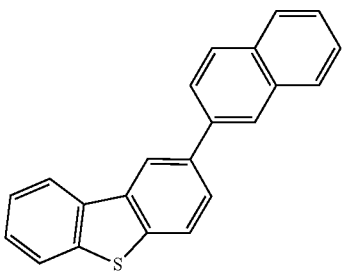
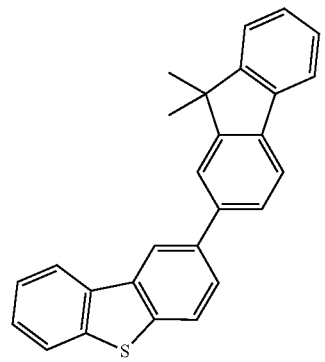
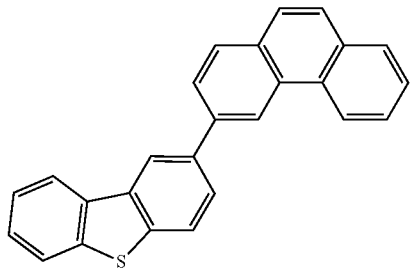
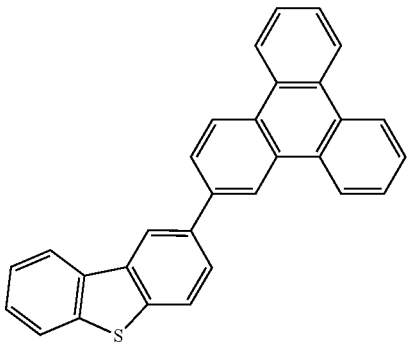

89
-continued
90
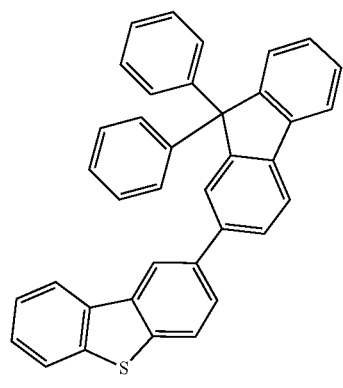 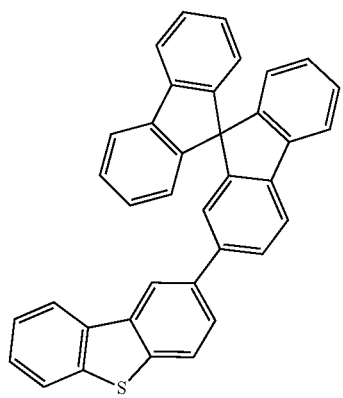 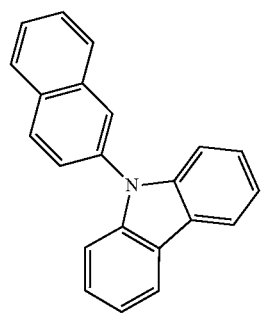
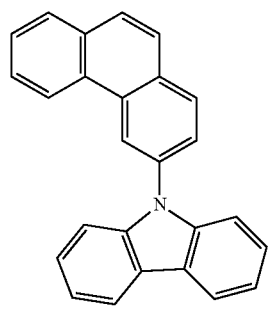 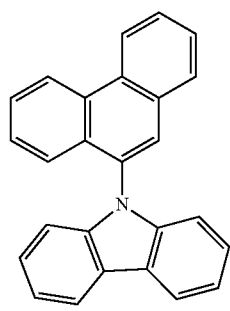 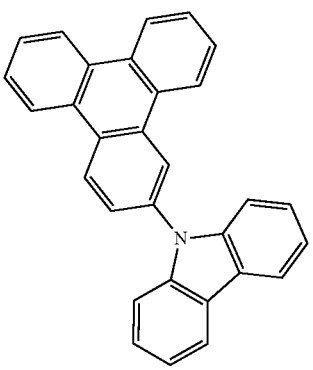 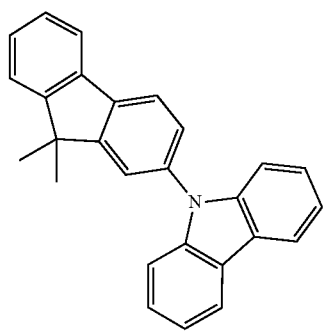
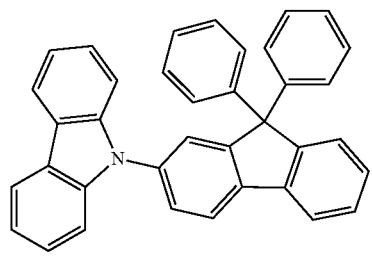 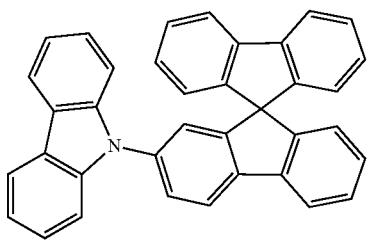
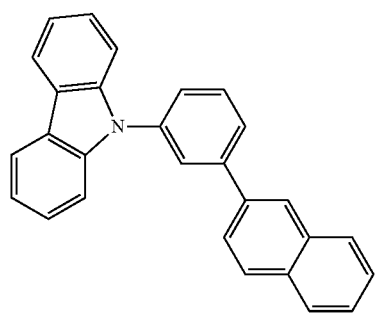 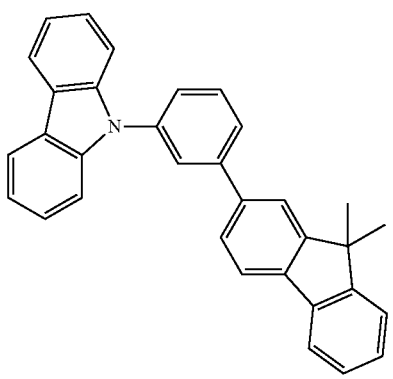 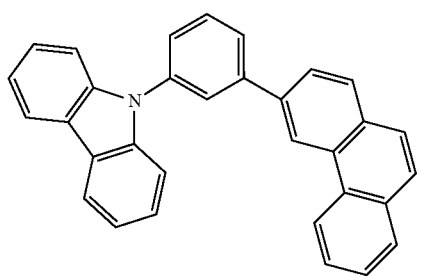

-continued
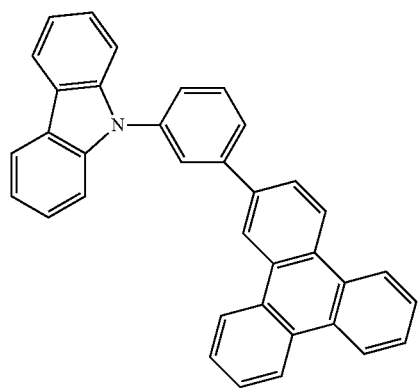
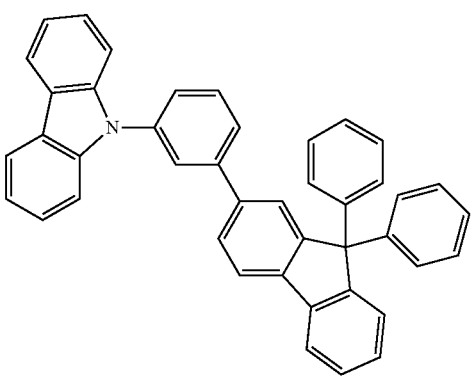
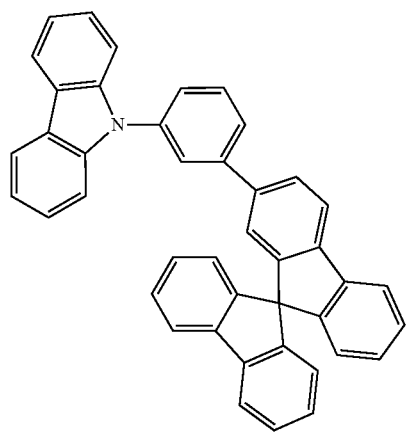
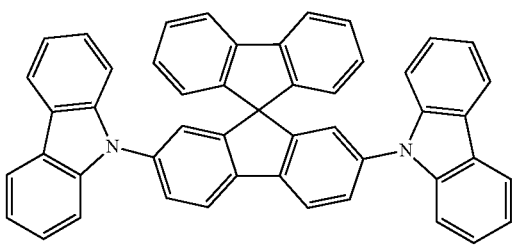
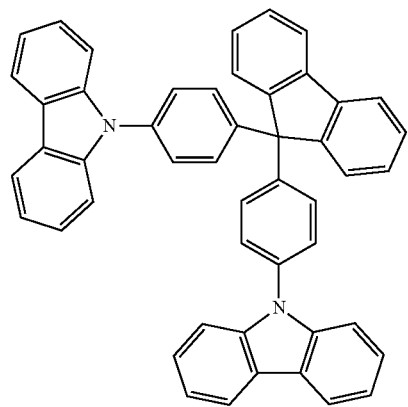
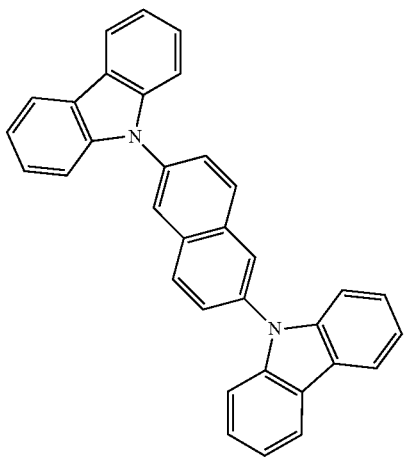

-continued
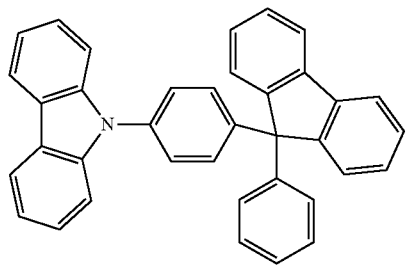
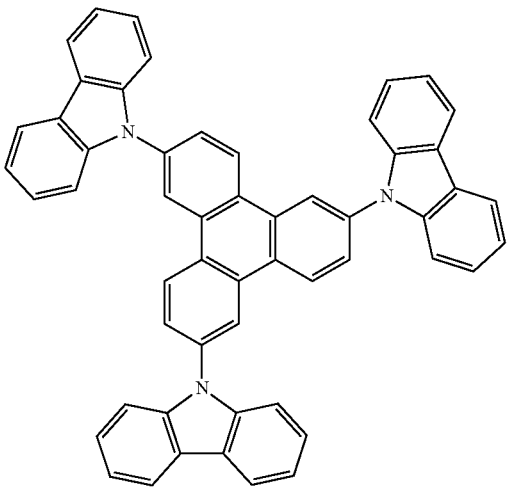
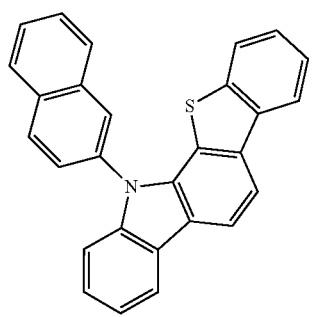
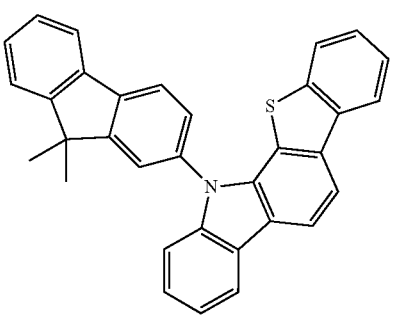
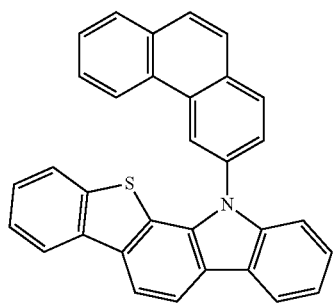
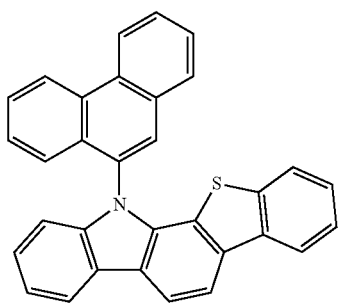
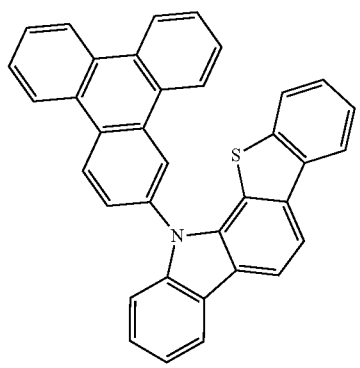
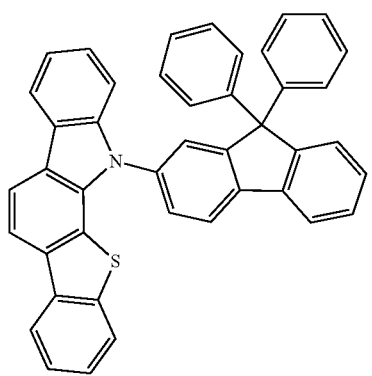
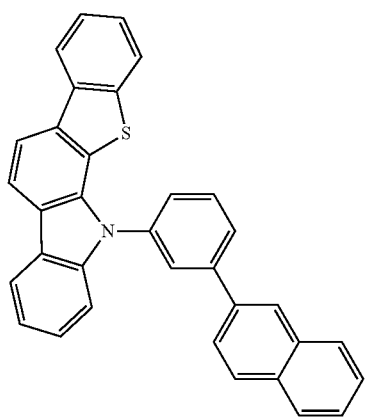
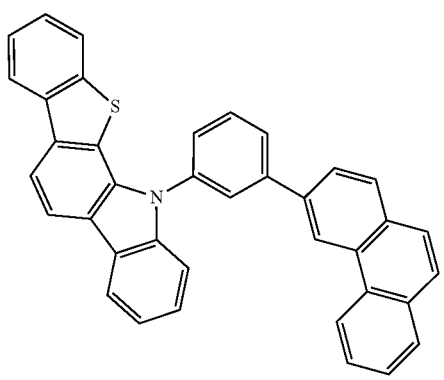

95
96
-continued
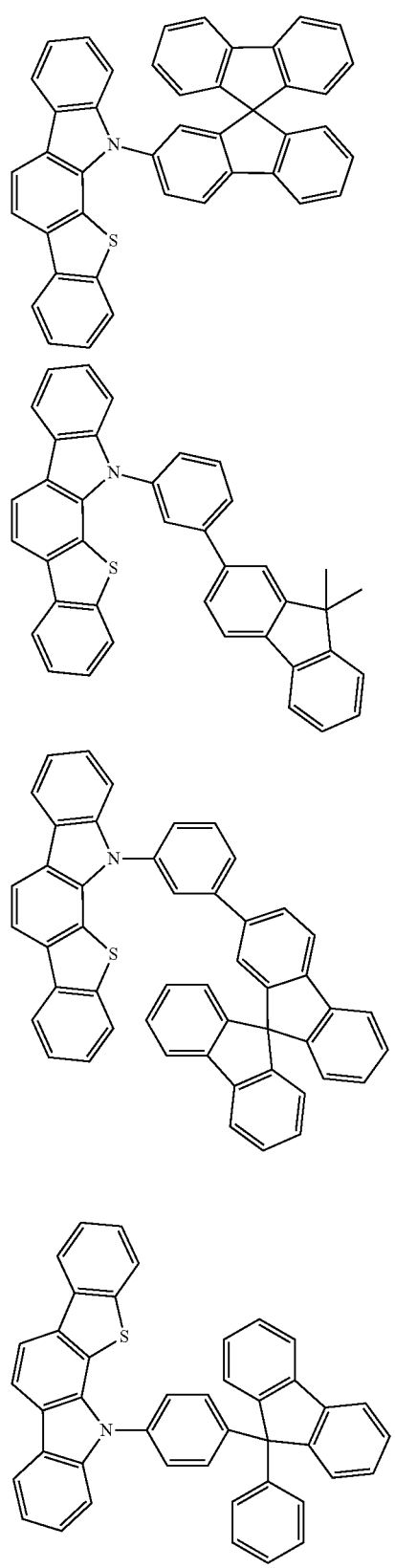
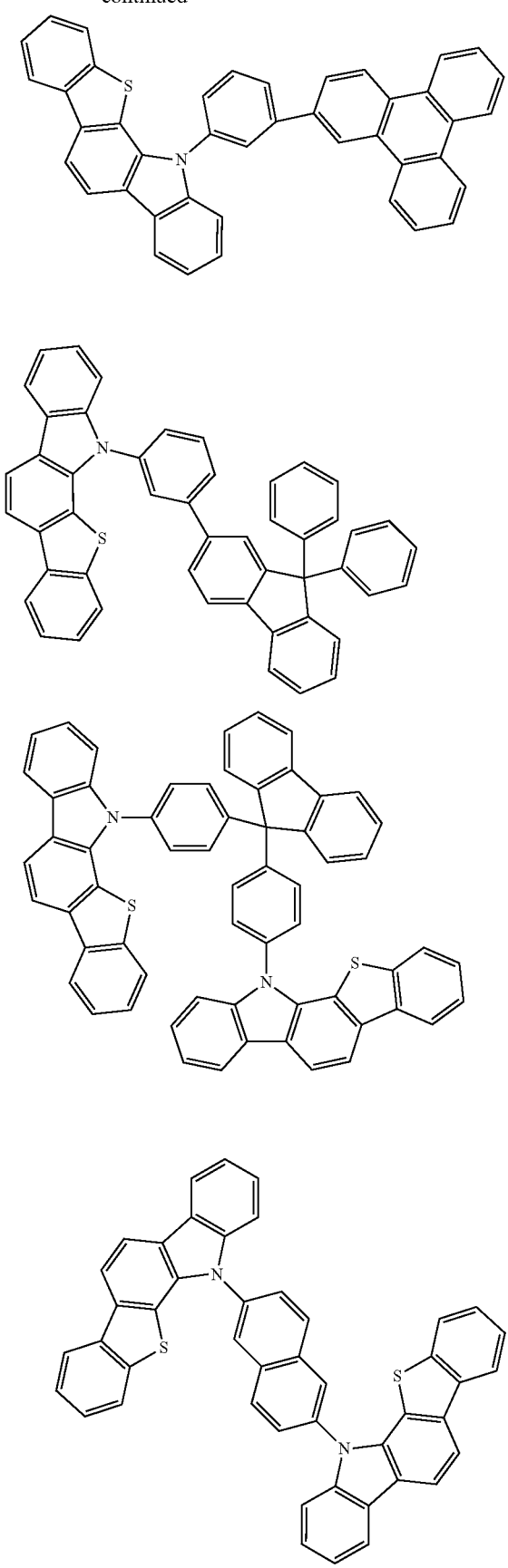

-continued
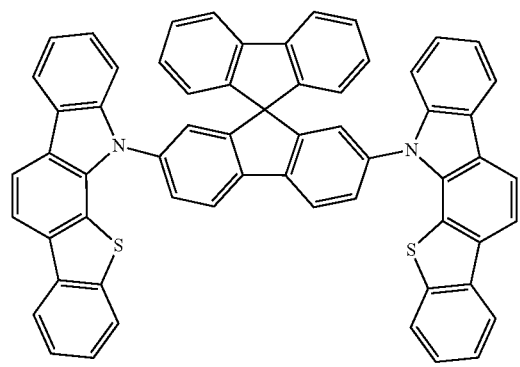
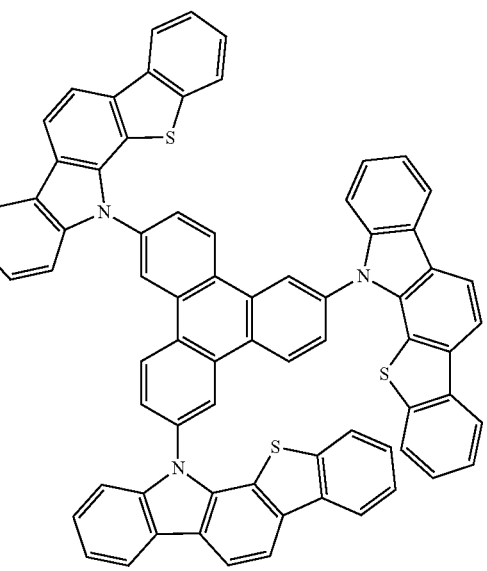
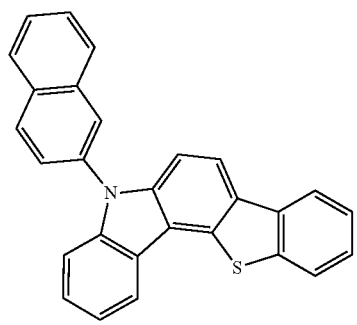
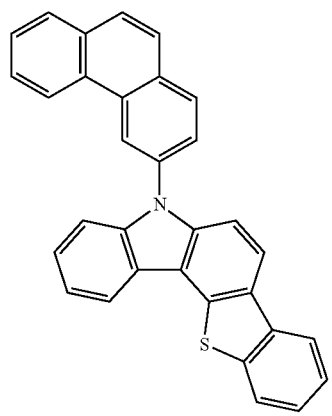
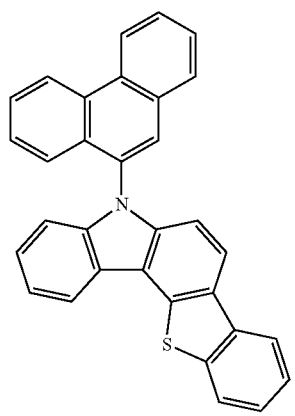
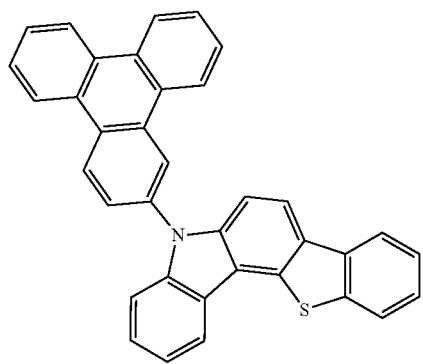
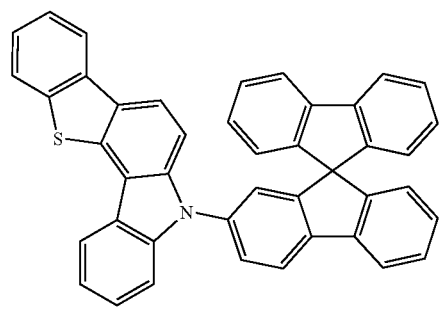
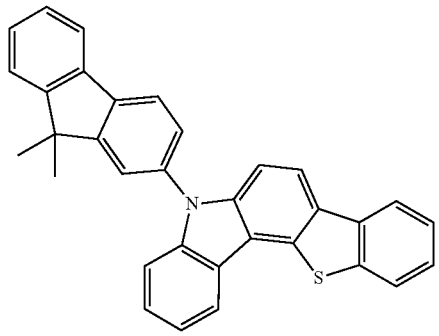
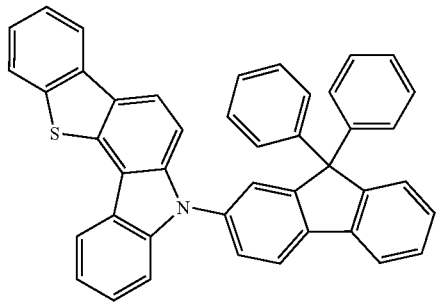

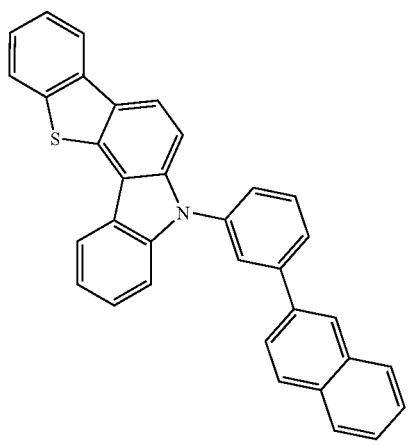
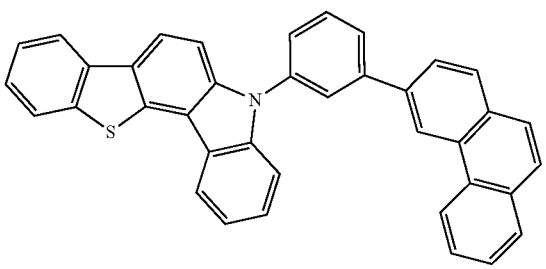
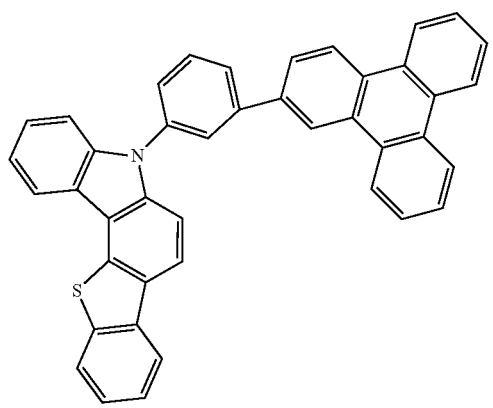
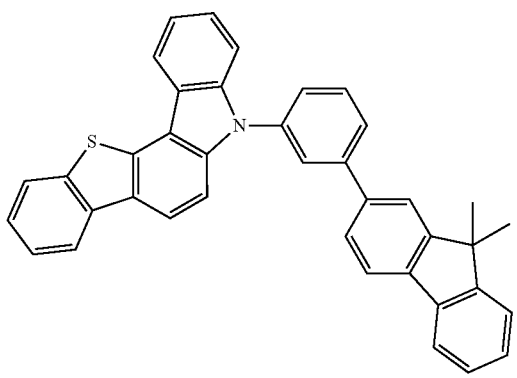
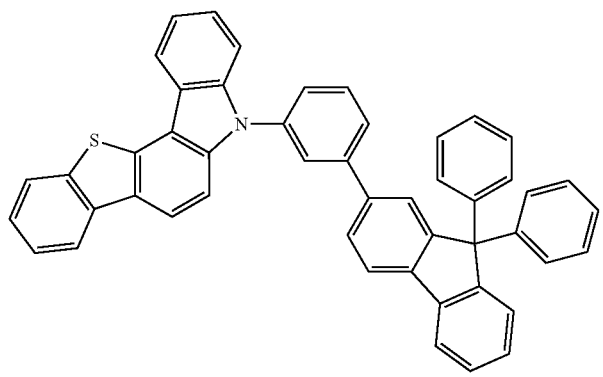
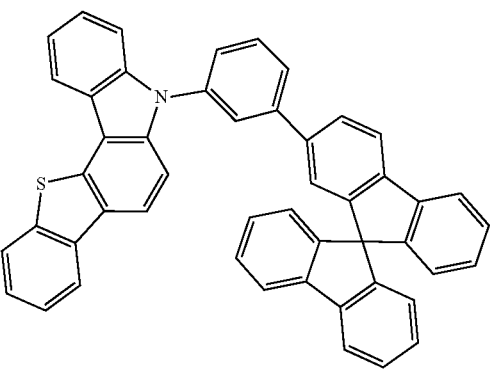
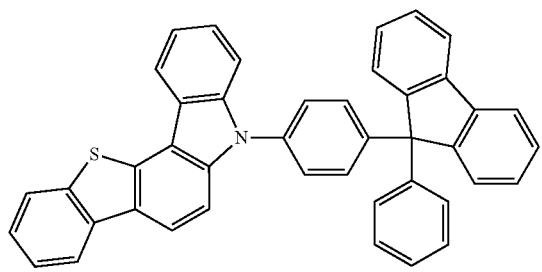

-continued
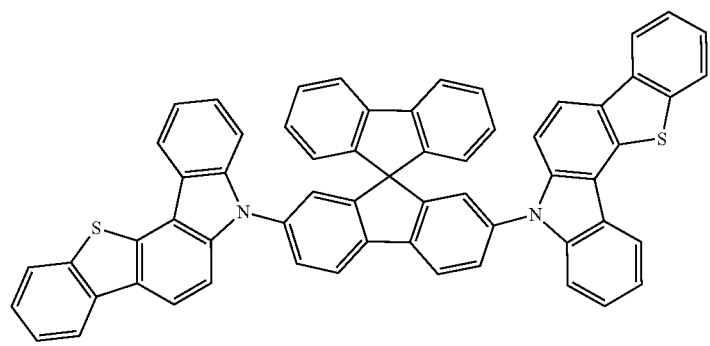
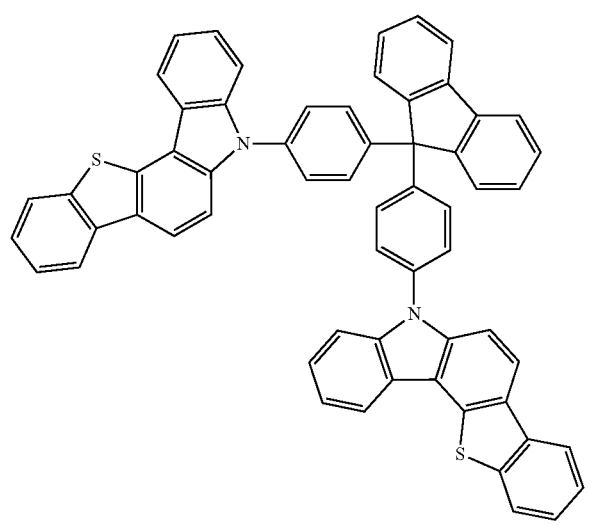
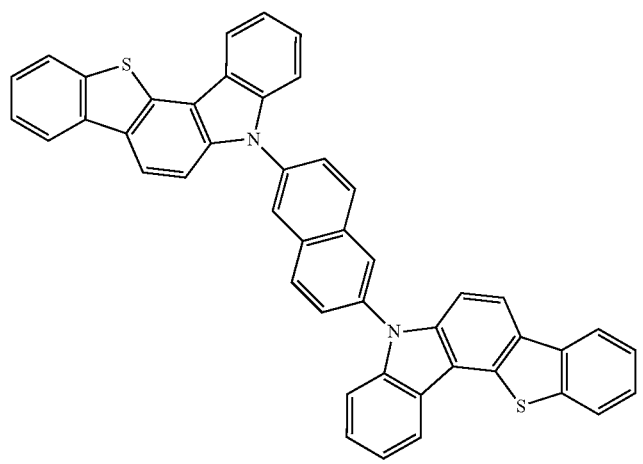

103
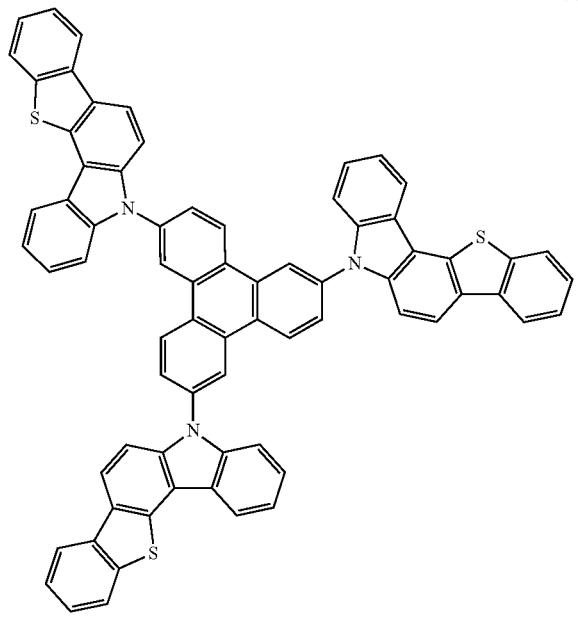
104
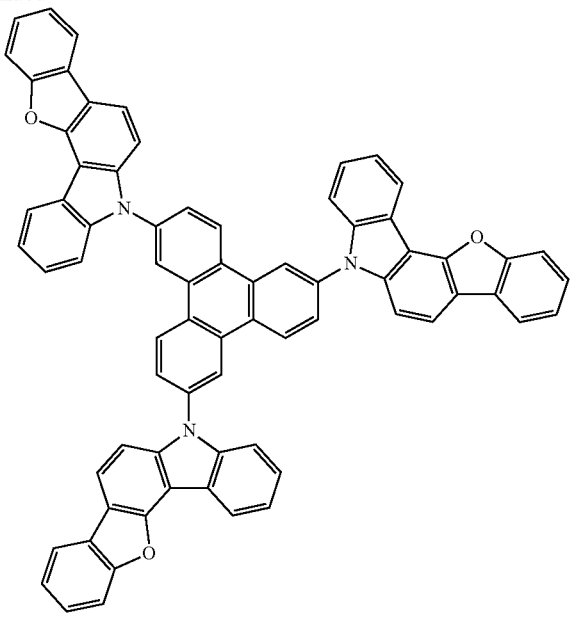
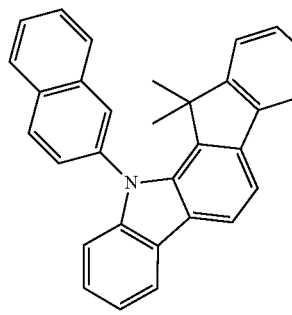
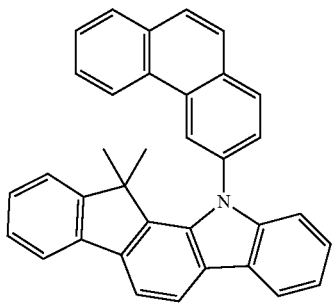
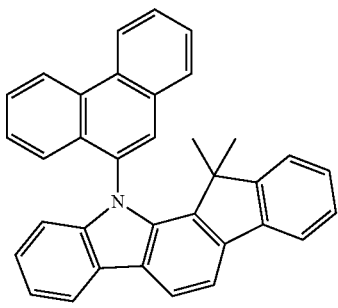
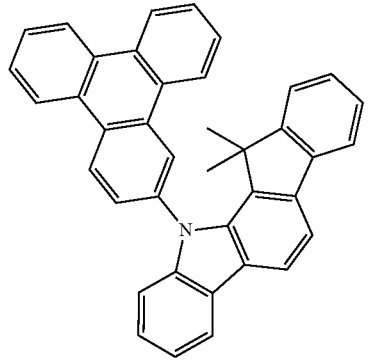
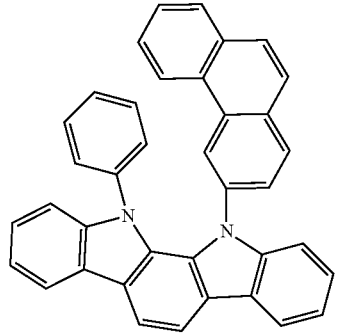
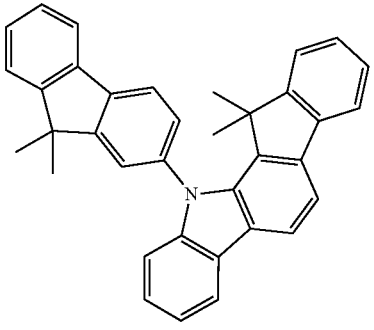
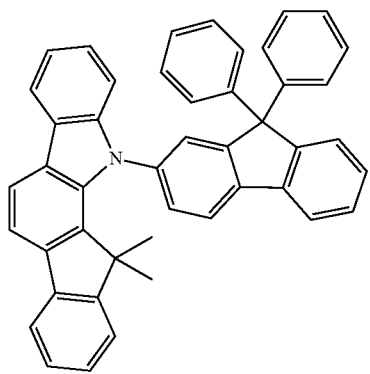
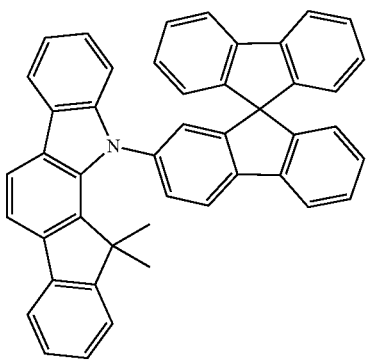
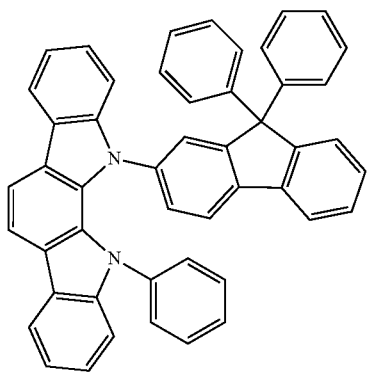

-continued
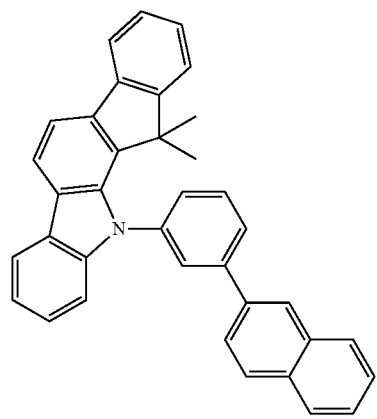
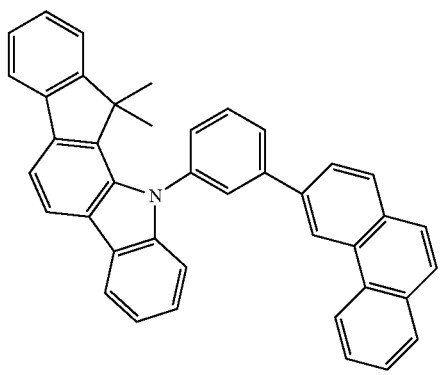
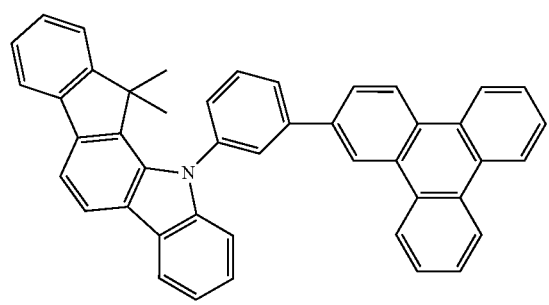
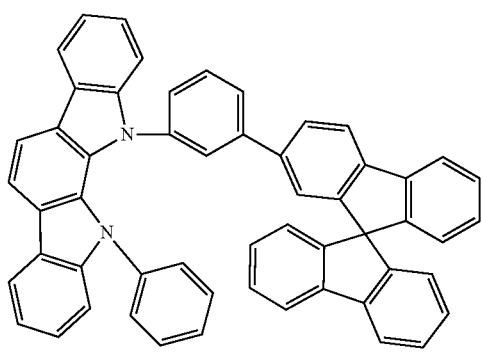
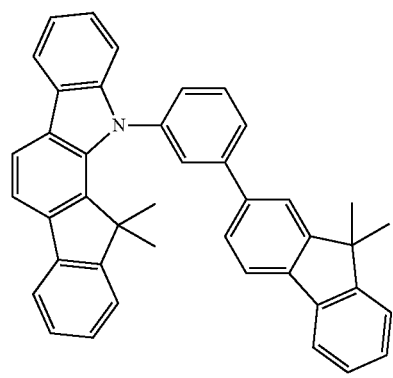
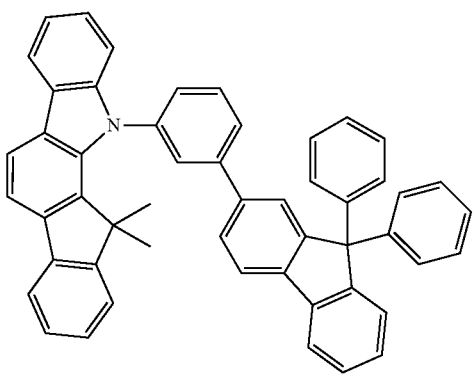
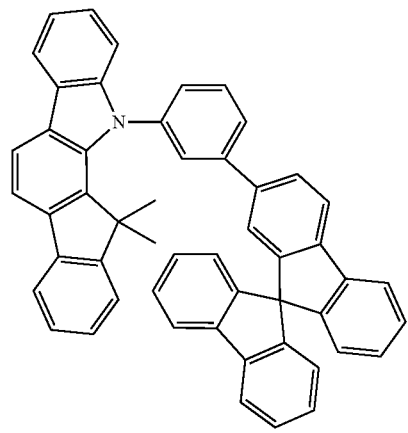
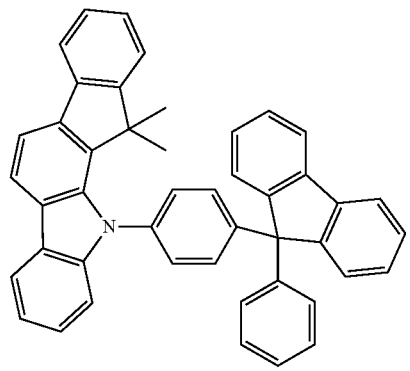

-continued
107
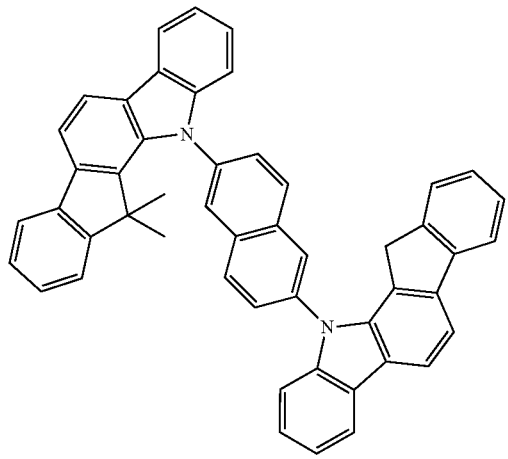
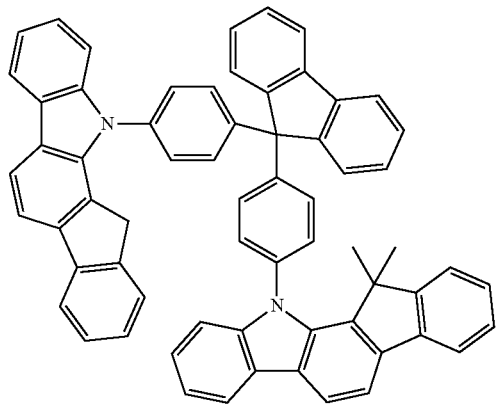
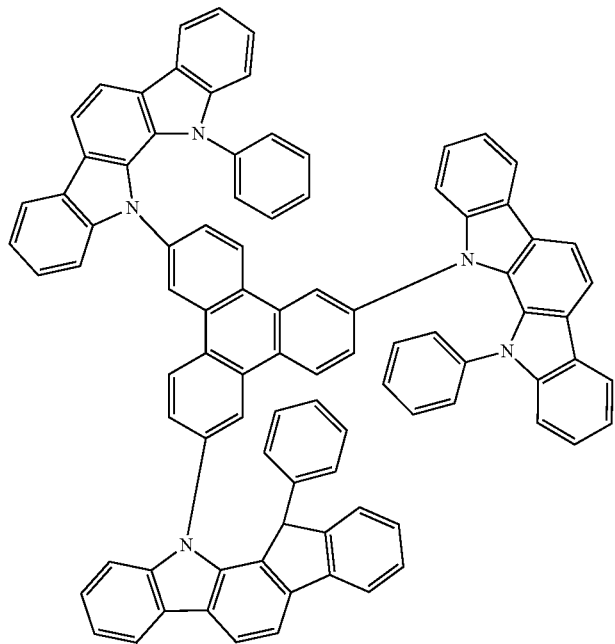
108
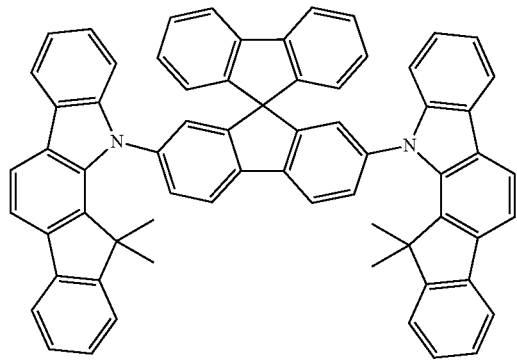
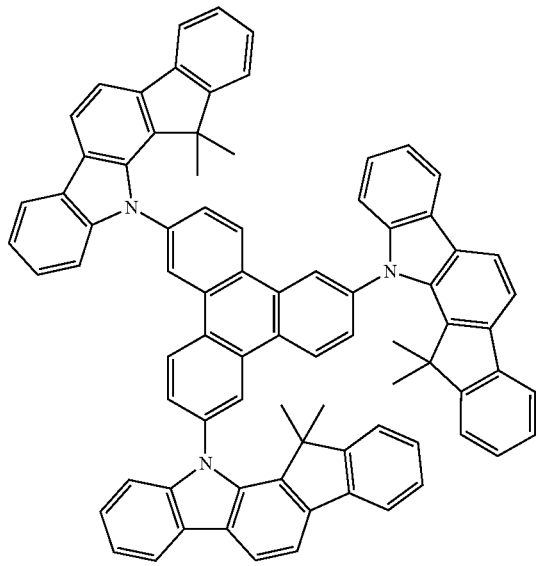
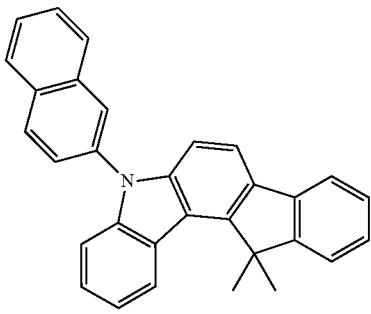

109 110
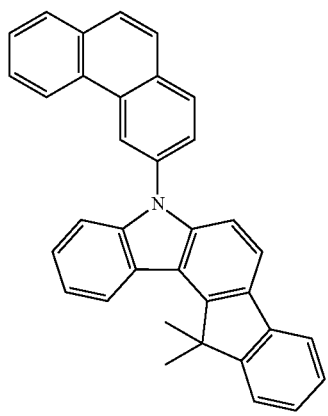 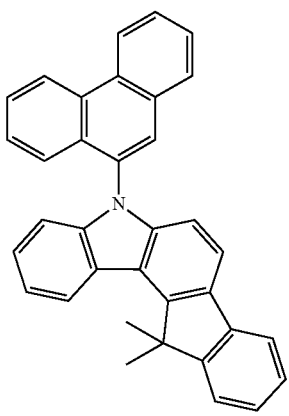 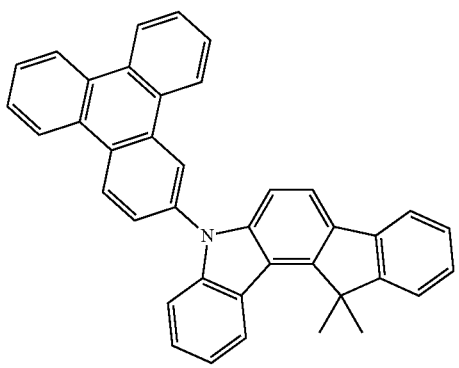
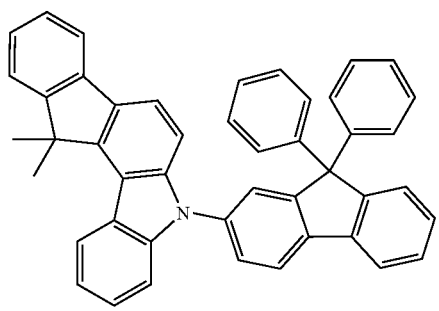 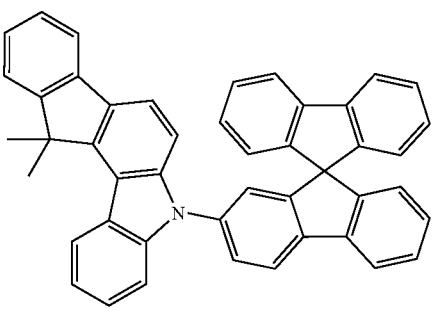
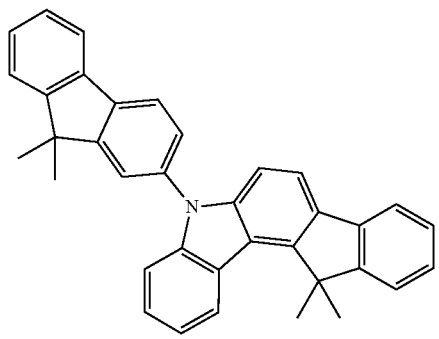 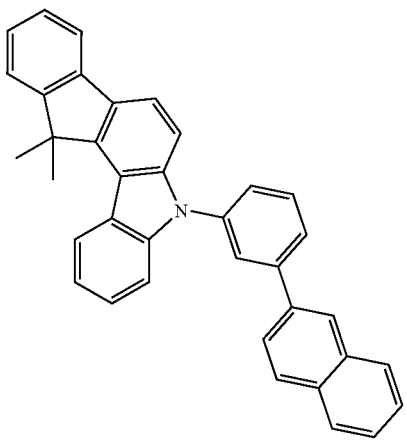
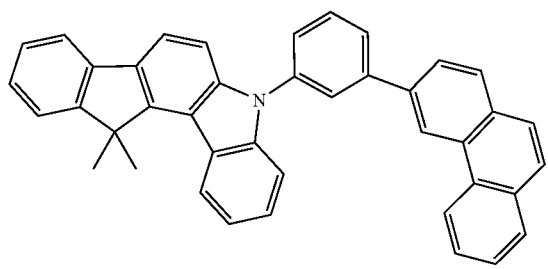

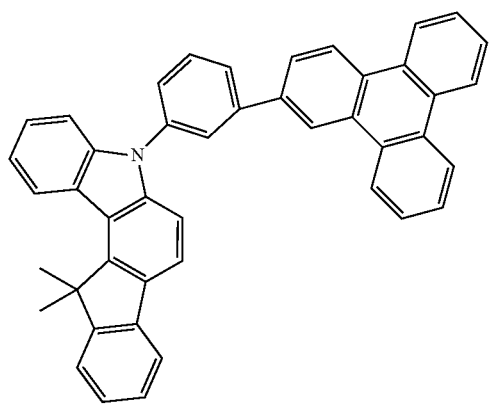
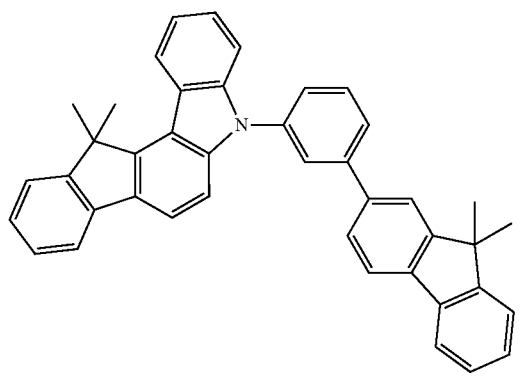
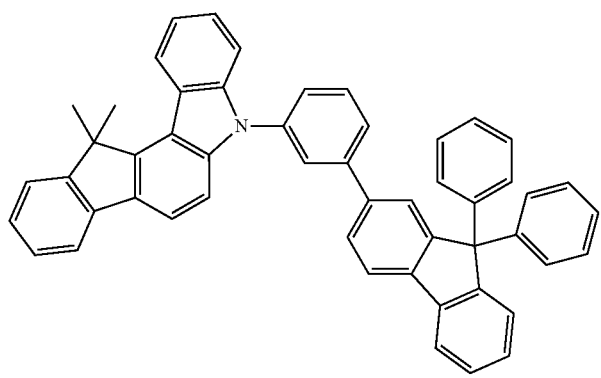
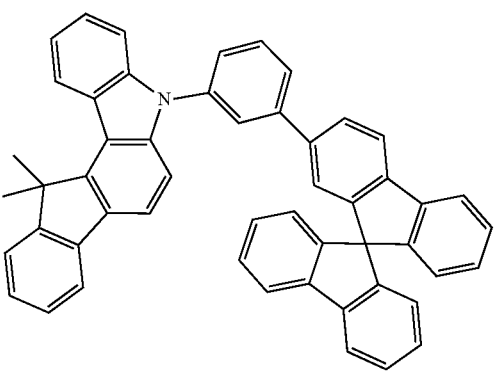
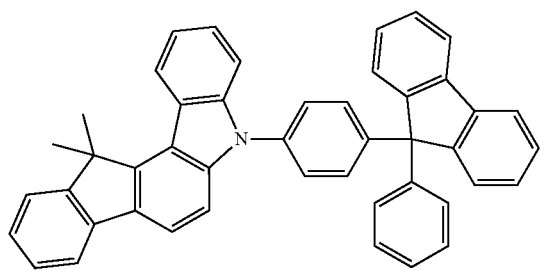
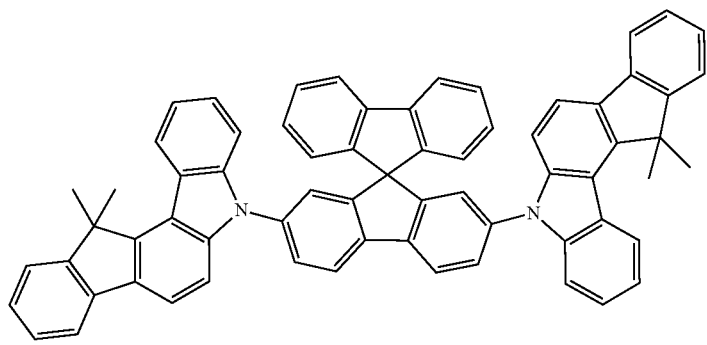

-continued
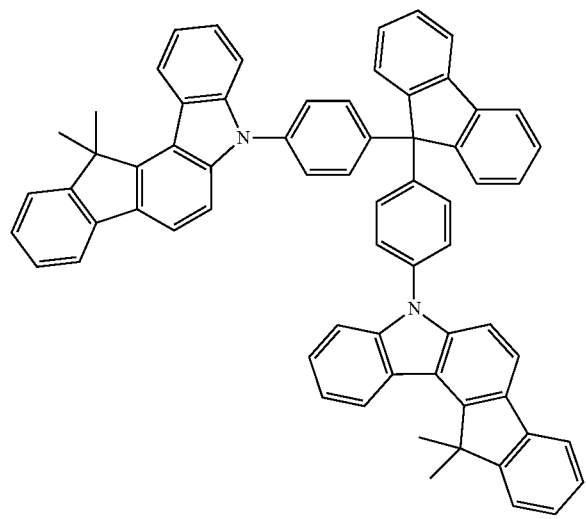
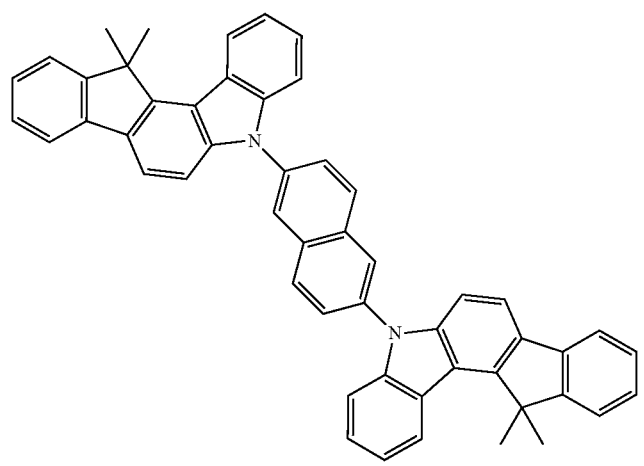
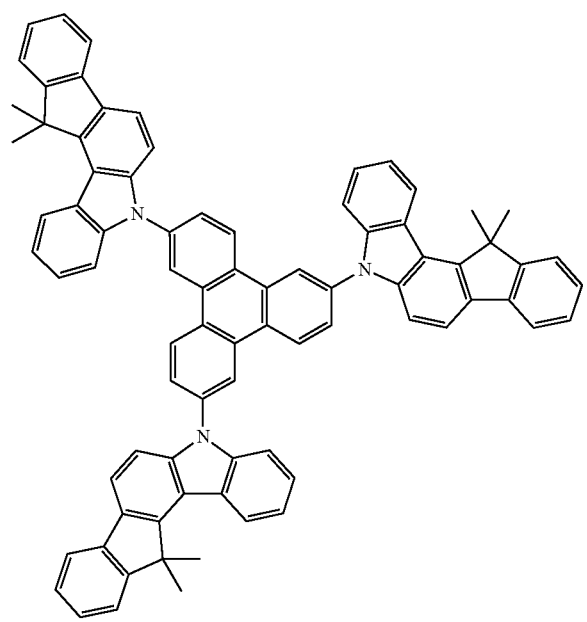

-continued
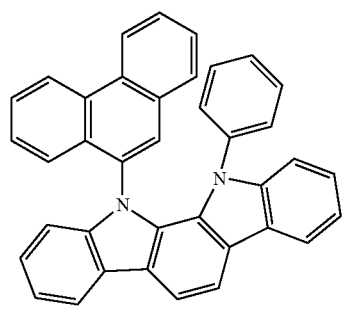
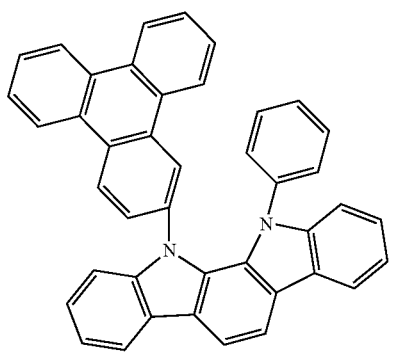
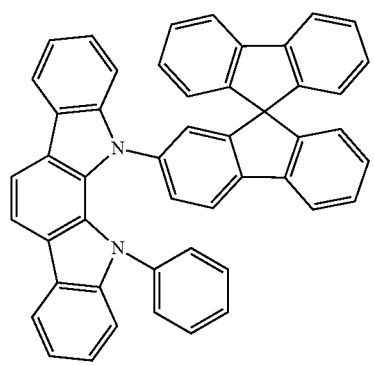
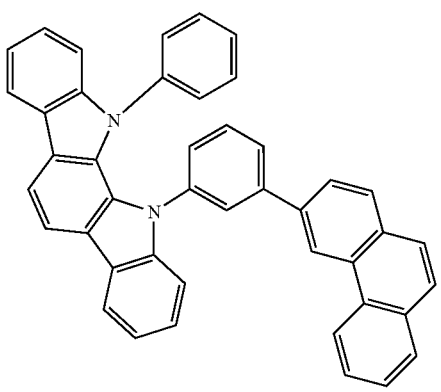
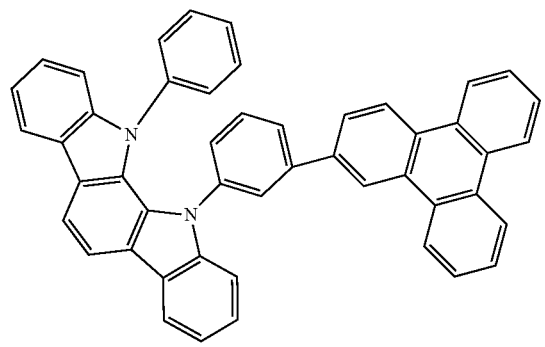
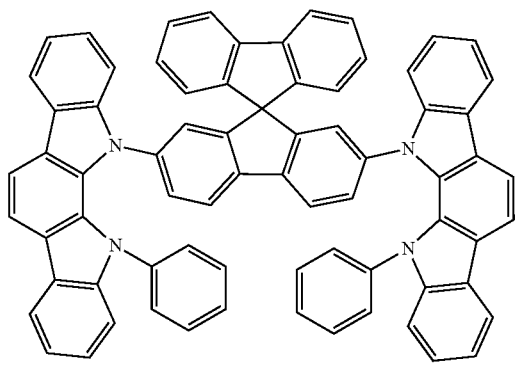
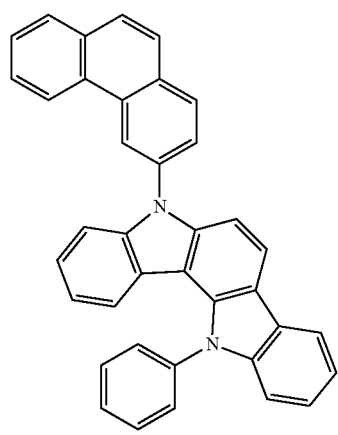
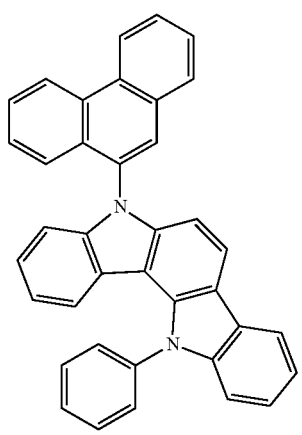

117
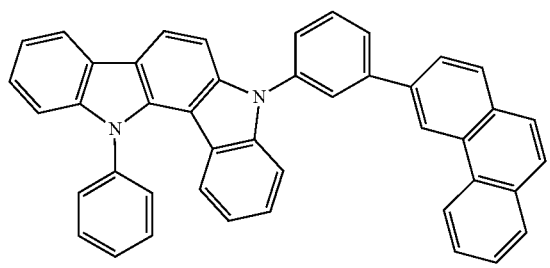
118
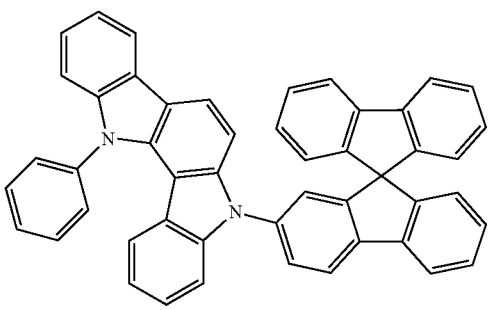
-continued
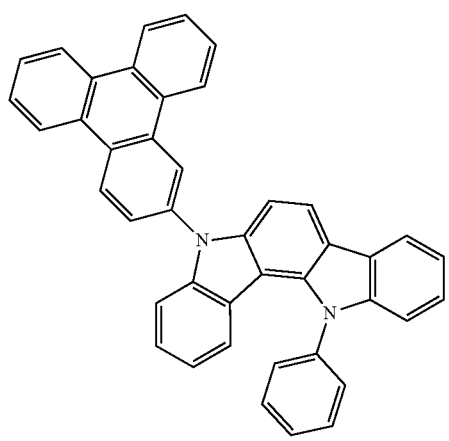
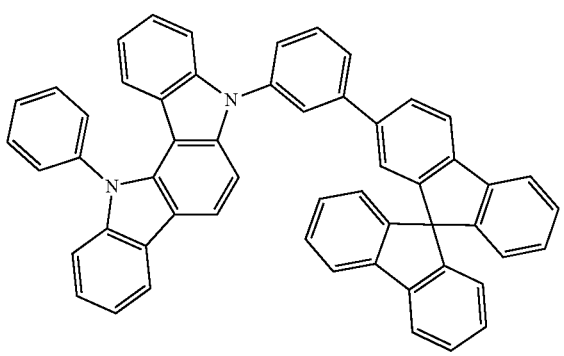
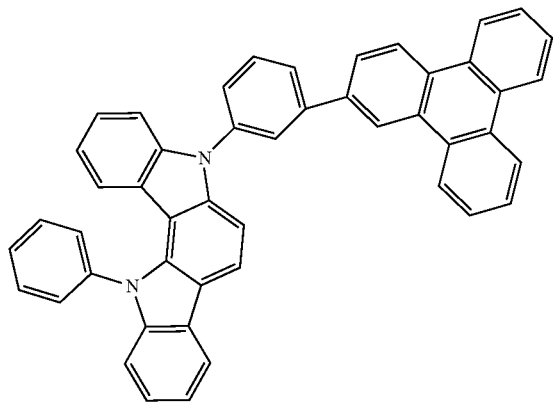
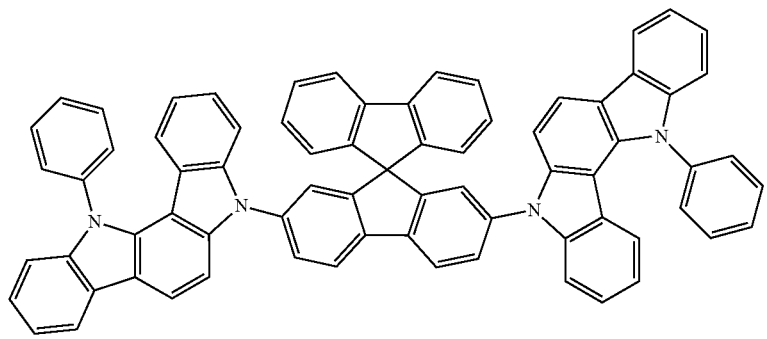

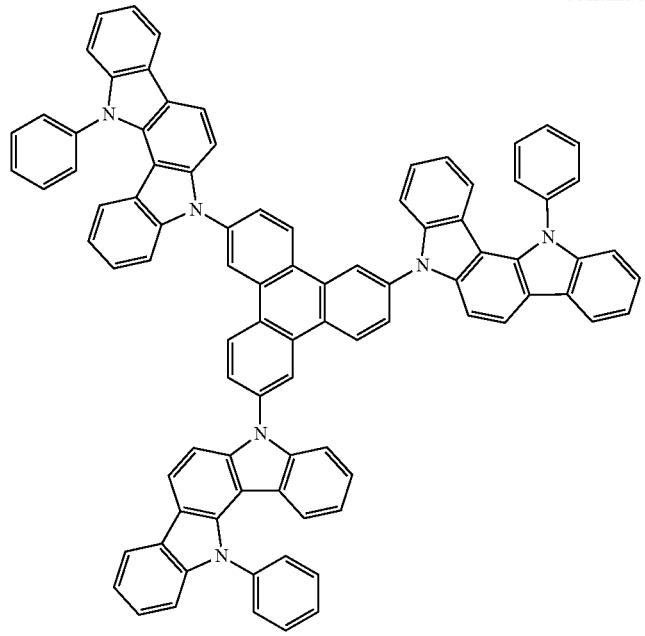 [SMILES: c1ccc(-n2c3ccccc3c3ccc4c(c5ccccc5n4-c4ccc5c(c4)c4ccc(-n6c7ccccc7c7c6ccc6c8ccccc8n(-c8ccccc8)c67)cc4c4ccc(-n6c7ccccc7c7c6ccc6c8ccccc8n(-c8ccccc8)c67)cc54)c32)cc1]

-continued

The first adjacent layer and the second adjacent layer (second organic layer) may preferably comprise one or more of the compound represented by the formulas (1) to (6). It is preferred that these layers consist essentially of the compound, and more preferred that these layers consist only of the compound. Here, the "essentially" means that the content of the compound represented by the formulas (1) to (6) is 90 wt % or more, 95 wt % or more, 98 wt % or more and 99 wt % or more.

The adjacent layer (second organic layer) may have a single layer structure or a multilayer structure. When the adjacent layer has a single layer structure, the layer may be formed only of the compound selected from compounds represented by the formulas (1) to (6) or may be formed of a mixture of the compound and other compounds.

When the adjacent layer has a multilayer structure, it may be of a stacked layer structure having a layer that comprises the compound represented by the formulas (1) to (6) and a layer that comprises a hole-transporting material.

The first adjacent layer and the second adjacent layer may further comprise a hole-transporting material. As the hole-transporting material, the materials for constituting a hole-injecting and transporting layer mentioned later can be given.

As the hole-transporting material, a compound comprising an amine skeleton or a carbazole skeleton is preferable.

Specifically, a compound represented by the formula (31) or (32) is preferable.

(31)

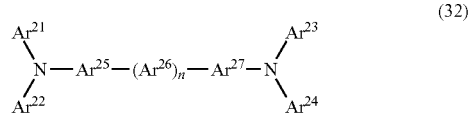
(32)

wherein in the formula, as for one of pairs of $Ar^{11}$ and $Ar^{12}$; $Ar^{11}$ and $Ar^{13}$; and $Ar^{12}$ and $Ar^{13}$, Ars may be bonded to each other to form a substituted or unsubstituted aromatic heterocyclic ring including 5 to 30 ring atoms (carbazole skeleton); and/or $Ar^{11}$ to $Ar^{13}$ are independently a substituted or unsubstituted aromatic hydrocarbon group including 6 to 30 ring carbon atoms or a substituted or unsubstituted aromatic heterocyclic group including 5 to 30 ring atoms;

As for at least one of pairs of $Ar^{21}$ and $Ar^{25}$; $Ar^{22}$ and $A^{25}$; $Ar^{23}$ and $Ar^{27}$; and $Ar^{24}$ and $Ar^{27}$, Ars may be bonded to each other to form a substituted or unsubstituted aromatic heterocyclic ring (carbazole skeleton) including 5 to 30 ring atoms; and/or $Ar^{21}$ to $Ar^{24}$ are independently a substituted or unsubstituted aromatic hydrocarbon group including 6 to 30 ring carbon atoms or a substituted or unsubstituted aromatic heterocyclic group including 5 to 30 ring atoms, and $Ar^{25}$ to $Ar^{27}$ are independently a substituted or unsubstituted divalent aromatic hydrocarbon group including 6 to 30 ring carbon atoms or a substituted or unsubstituted divalent aromatic heterocyclic group including 5 to 30 ring atoms.

n is an integer of 0 to 2, and when n is 0, $(Ar^{26})_0$ is a single bond.

Preferable hole-transporting materials are stated in WO20091/145016 or the like.

For example, the following compounds can be given.

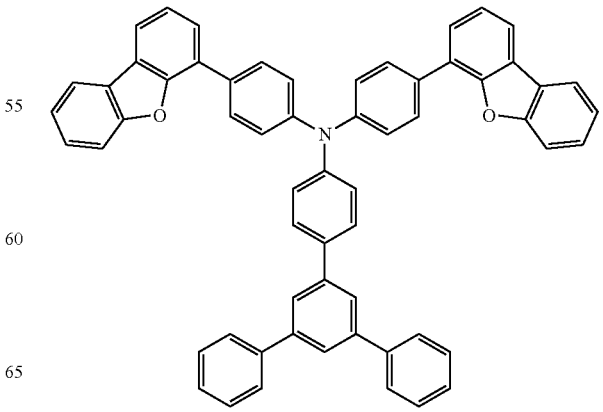

121
-continued
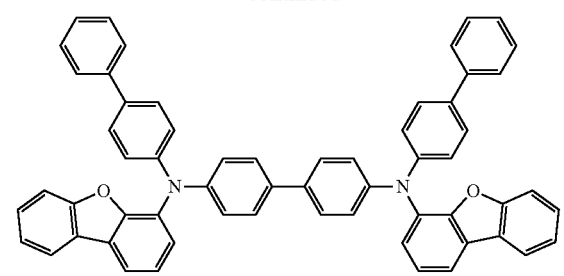
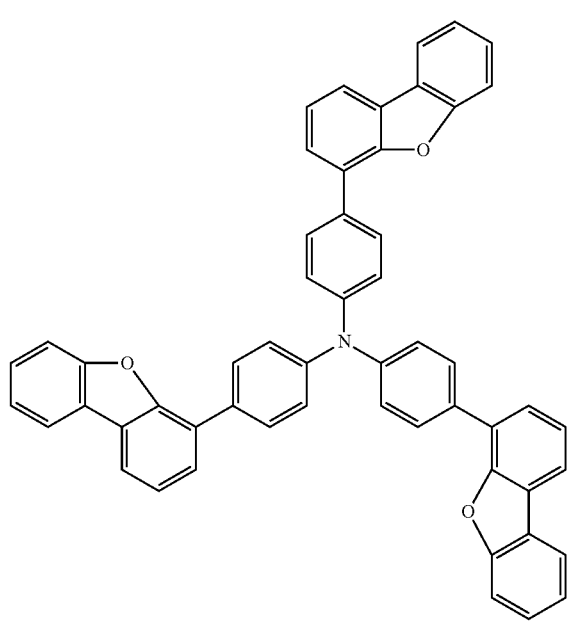
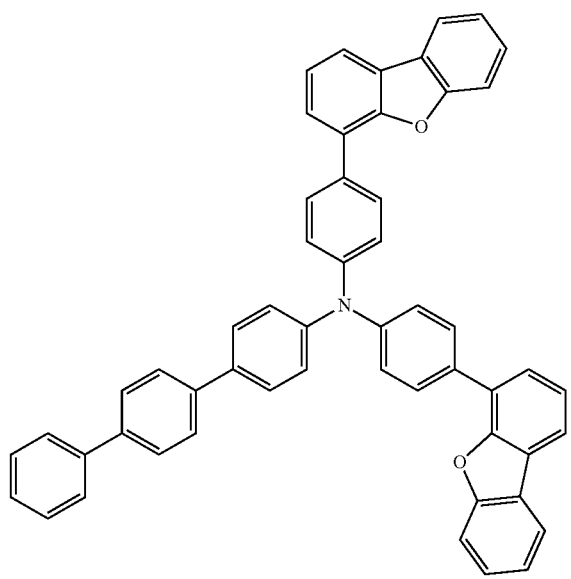
122
-continued
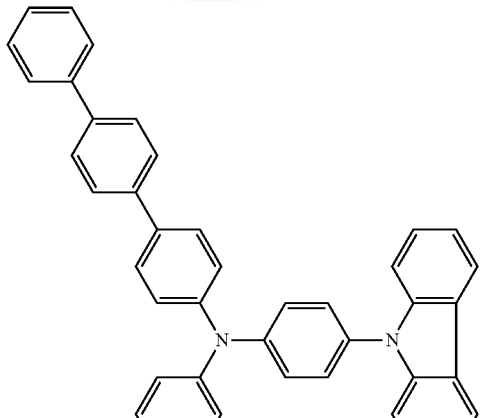
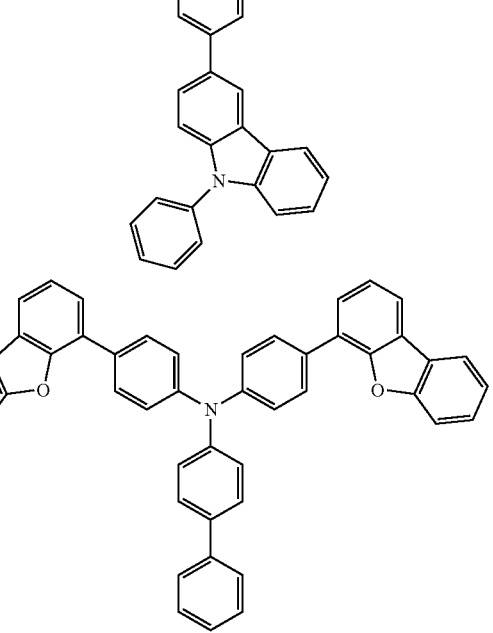

-continued

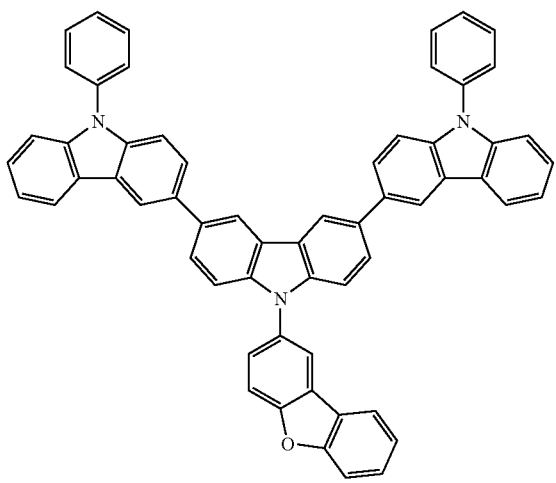

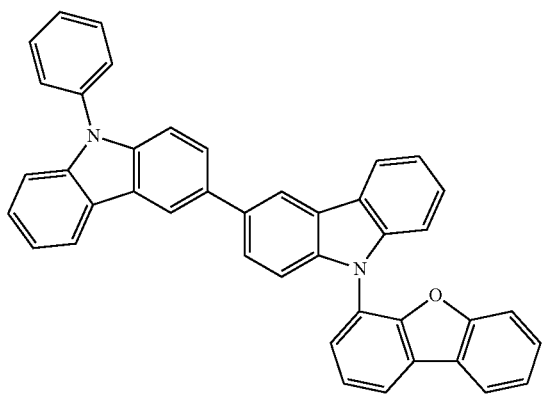

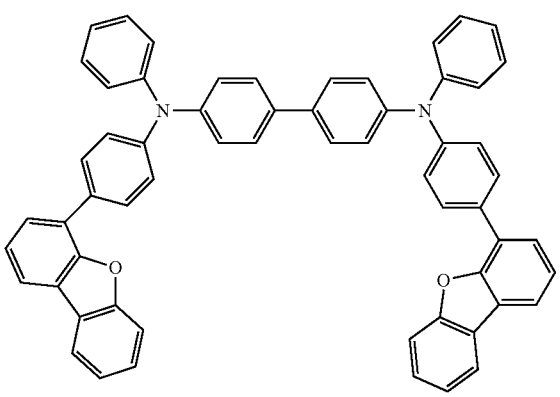

-continued

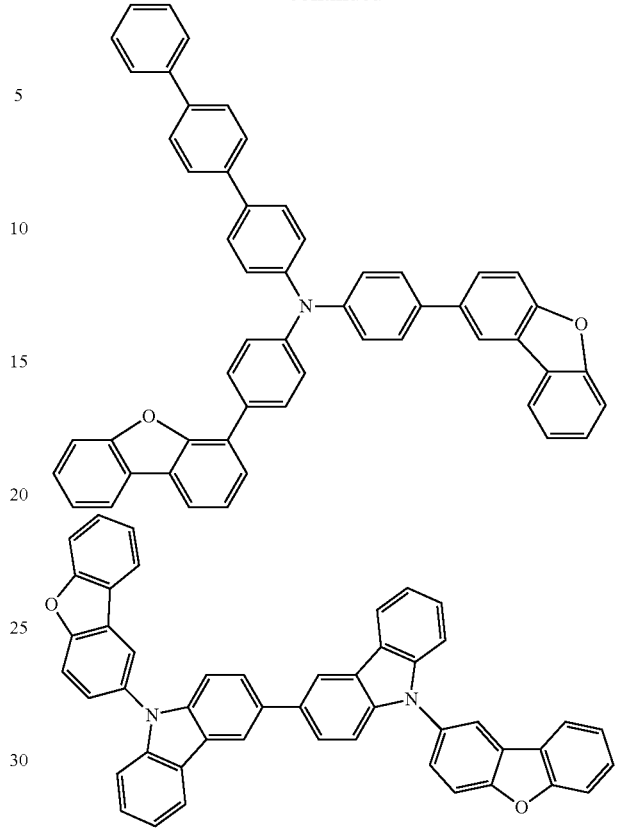

It is preferred that the first adjacent layer and the second adjacent layer have the same film thickness. By allowing the first adjacent layer to have the same film thickness as that of the second adjacent layer, the first adjacent layer and the second adjacent layer can be formed simultaneously, whereby the production of an organic EL multicolor light-emitting apparatus can be conducted by a simplified process and at a low cost.

When the first adjacent layer and the second adjacent layer have the same film thickness, the thickness thereof is 5 nm to 20 nm, for example, preferably 7 to 15 nm.

If the thickness of the adjacent layer is less than 5 nm, the adjacent layer does not fully function, and as a result, a sufficient luminous efficiency or a prolonged life of the first light-emitting device (for example, a green phosphorescent emitting device or a red phosphorescent emitting device) or the second light-emitting device (for example, a blue fluorescent emitting device) cannot be obtained. On the other hand, when the thickness of the adjacent layer exceeds 20 nm, the voltage of the light-emitting device may be increased, the carrier balance may be deteriorated, and as a result, a sufficient efficiency or a prolonged life may not be obtained.

[Light-Emitting Device]

As for a first light-emitting device and a second light-emitting device arranged in parallel on the substrate of the organic EL multicolor light-emitting apparatus of the invention, the first light-emitting device has a structure of anode/hole-injecting layer/hole-transporting layer/first emitting layer/first adjacent layer/second electron-injecting and transporting layer/first electron-injecting and transporting layer/cathode, for example, and the second light-emitting device has a structure of anode/hole-injecting layer/hole-transporting layer/second adjacent layer/second emitting layer/first electron-injecting and transporting layer/cathode, for example.

Here, the first adjacent layer and the second adjacent layer respectively contain any of the above-mentioned compounds (1) to (6).

Further, if the second emitting layer is a blue-emitting layer, the second emitting layer may be the same as the second electron-injecting and transporting layer of the first light-emitting device.

Emission from the first emitting layer and the second emitting layer can be outcoupled from the anode side, the cathode side or both sides.

[Emitting Layer]

An emitting layer has a function of providing a site in which electrons and holes are re-combined to cause emission.

Note that electrons and holes may be injected into the emitting layer with different degrees, or the transportation capabilities indicated by the mobility of holes and electrons may differ. It is preferable that the emitting layer move either one of carriers.

The first emitting layer (corresponding to the first organic layer) comprises the first light-emitting dopant, preferably a phosphorescent dopant, and can function as a phosphorescent emitting layer (for example, the red or yellow phosphorescent emitting layer or the green phosphorescent emitting layer). The phosphorescent emitting layer is preferably a phosphorescent emitting layer comprising a phosphorescent host and a phosphorescent dopant.

The phosphorescent dopant may be any of a high-molecular (molecular weight: about 10,000 or more), a mid-molecular (molecular weight: about 900 to about 10,000) and a low-molecular (molecular weight: about 900 or less) material. As for the specific structure, a compound comprising a carbazole skeleton and an aromatic ring or a nitrogen-containing aromatic ring in the same molecule; a compound comprising a plurality of carbazole skeletons in the same molecule; a compound formed by linkage of a plurality of aromatic rings, fused aromatic rings and nitrogen-containing aromatic heterocyclic rings can be given. The host may be used singly or in a mixture of two or more.

As the phosphorescent dopant, a metal complex compound can be given. The metal complex compound is preferably a compound comprising a metal atom selected from Ir, Pt, Os, Au, Cu, Re and Ru and a ligand. It is preferred that the ligand have an ortho-metalated bond.

In respect of high phosphorescent quantum yield and further improvement in external quantum efficiency of a light-emitting device, it is preferred that the phosphorescent dopant be a compound comprising a metal element selected from Ir, Os and Pt. The phosphorescent dopant is further preferably a metal complex such as an iridium complex, an osmium complex and a platinum complex. Among these, an iridium complex and a platinum complex are more preferable, and an ortho-metalated iridium complex is most preferable. The dopant may be used singly or in combination of two or more.

The first emitting layer may comprise an adjacent layer compound, a hole-transporting material and an electron-transporting material, if necessary.

The second emitting layer (corresponding to the third organic layer) comprises the second light-emitting dopant, preferably a fluorescent dopant, and can function as a fluorescent emitting layer (for example, a blue fluorescent layer). The fluorescent emitting layer is preferably a fluorescent emitting layer comprising the following fluorescent host and the following fluorescent dopant.

As the fluorescent host, various fused aromatic ring compounds can be given. For example, one or more selected from the following compounds (41) to (51) can be used.

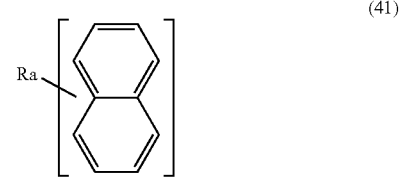

(41)

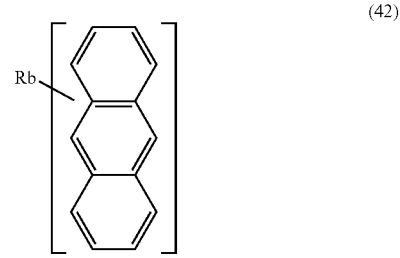

(42)

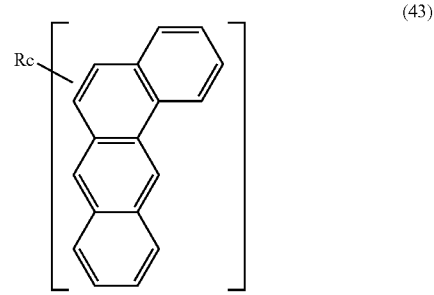

(43)

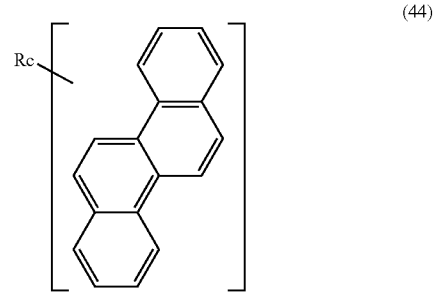

(44)

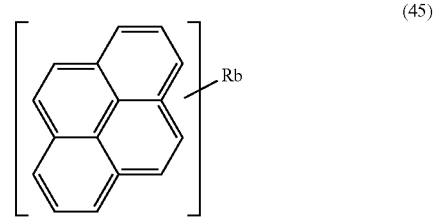

(45)

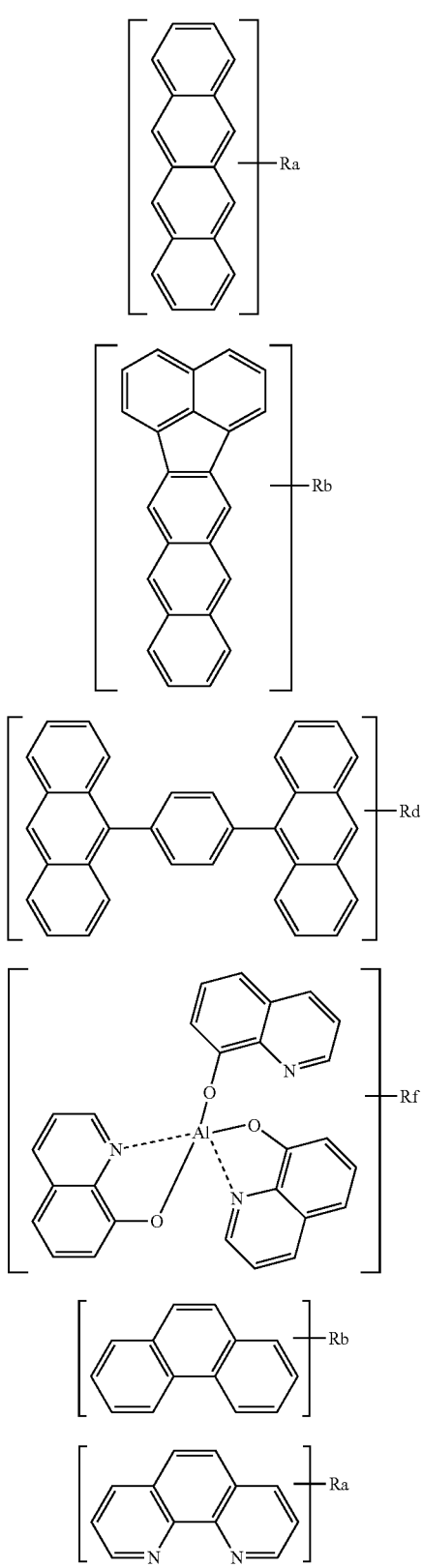

wherein in the formula, R is a substituted or unsubstituted aryl group including 6 to 40 ring carbon atoms (preferably, a substituted or unsubstituted aryl group including 6 to 18 ring carbon atoms), a substituted or unsubstituted heterocyclic group including 3 to 40 ring atoms (preferably, a substituted or unsubstituted heterocyclic group including 3 to 18 ring atoms) or a substituted or unsubstituted alkyl group including 1 to 50 carbon atoms (preferably, a substituted or unsubstituted alkyl group including 1 to 20 carbon atoms).

a is an integer of 0 to 7, b is an integer of 0 to 9, c is an integer of 0 to 11, d is an integer of 0 to 22 and f is an integer of 0 to 18, and when each of a to f is 2 or more, plural Rs may be the same or different.

The aryl group, the heterocyclic group and the alkyl group are the same as those of the substituted or unsubstituted aromatic hydrocarbon group, a substituted or unsubstituted aromatic heterocyclic group and the substituted or unsubstituted alkyl group represented by $Ar^1$ to $Ar^4$ of the adjacent layer compound.

In the formulas (41) to (51), R may be bonded to any of the aromatic ring or the heterocyclic ring, and two or more Rs may be bonded to the same aromatic ring or the heterocyclic ring.

As the fluorescent dopant, the aromatic amine represented by the following formula, the styrylamine represented by the following formula or the like are preferable. The fluorescent dopant may be used alone or in combination of two or more.

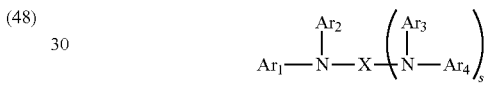

wherein in the formula, $Ar^1$ to $Ar^4$ are independently a substituted or unsubstituted aryl group including 6 to 40 ring carbon atoms, a substituted or unsubstituted heterocyclic group including 3 to 40 ring atoms or a substituted or unsubstituted alkyl group including 1 to 50 carbon atoms.

X is a substituted or unsubstituted 1+s valent fused aromatic ring group including 10 to 40 ring carbon atoms or a substituted or unsubstituted 1+s valent styryl group.

s is an integer of 0 to 3, and when s is 2 or 3, two or three —NAr³Ar⁴ may be the same or different, and when s is 0, —NAr³Ar⁴ is a hydrogen atom.

[Substrate]

As the substrate, a glass plate, a polymer plate or the like can be used.

Examples of the glass plate, in particular, include soda-lime glass, barium/strontium-containing glass, lead glass, aluminosilicate glass, borosilicate glass, barium borosilicate glass and quartz.

Examples of the polymer plate include polycarbonate, acrylic polymer, polyethylene terephthalate, polyethersulfone and polysulfone.

[Anode]

The anode is formed of a conductive material, for example, and one having a work function larger than 4 eV is suitable.

As the conductive material, carbon, aluminum, vanadium, iron, cobalt, nickel, tungsten, silver, gold, platinum and palladium, alloys thereof, metal oxides such as tin oxide and indium oxide which are used for an ITO substrate and a NESA substrate and an organic conductive resin such as a polythiophene and polypyrrole are used.

The anode may be formed of two or more layers, if necessary.

[Cathode]

The cathode is formed of a conductive material, for example, and one having a work function smaller than 4 eV is suitable.

As the conductive material, magnesium, calcium, tin, lead, titanium, yttrium, lithium, ruthenium, manganese, aluminum and lithium fluoride, and alloys thereof are used, but usable materials are not limited thereto.

Representative examples of the alloy include, though not limited thereto, a magnesium/silver alloy, a magnesium/indium alloy and a lithium/aluminum alloy. The amount ratio of an alloy is controlled by the temperature of the deposition source, atmosphere, vacuum degree or the like, and a suitable ratio is selected.

If necessary, the cathode may be formed of two or more layers. This cathode can be formed by making the conductive material into a thin film by vapor deposition, sputtering or some other methods.

In the case where light is outcoupled from the emitting layer through the cathode, the cathode preferably has a light transmittance of larger than 10%.

The sheet resistance of the cathode is preferably several hundreds Ω/□ less, and the film thickness thereof is usually from 10 nm to 1 μm, preferably from 50 to 200 nm.

[Hole-injecting Layer and Hole-transporting Layer]

The hole-injecting and transporting layer is a layer which helps injection of holes to the emitting layer, and transports the holes to the emission region. It has a large hole mobility, and normally has a small ionization energy of 5.6 eV or less.

As the material for such hole-injecting and transporting layer, a material which transports holes to the emitting layer at a lower electric field is preferable. Further, it is preferred that the mobility of holes be at least $10^{-4}$ cm$^2$/V·sec when applying an electric field of $10^4$ to $10^6$ V/cm.

Specific examples of materials for a hole-injecting and transporting layer include triazole derivatives (see U.S. Pat. No. 3,112,197 and others), oxadiazole derivatives (see U.S. Pat. No. 3,189,447 and others), imidazole derivatives (see JP-B-37-16096 and others), polyarylalkane derivatives (see U.S. Pat. Nos. 3,615,402, 3,820,989 and 3,542,544, JP-B-45-555 and 51-10983, JP-A-51-93224, 55-17105, 56-4148, 55-108667, 55-156953 and 56-36656, and others), pyrazoline derivatives and pyrazolone derivatives (see U.S. Pat. Nos. 3,180,729 and 4,278,746, JP-A-55-88064, 55-88065, 49-105537, 55-51086, 56-80051, 56-88141, 57-45545, 54-112637 and 55-74546, and others), phenylenediamine derivatives (see U.S. Pat. No. 3,615,404, JP-B-51-10105, 46-3712 and 47-25336, JP-A-54-53435, 54-110536 and 54-119925, and others), arylamine derivatives (see U.S. Pat. Nos. 3,567,450, 3,180,703, 3,240,597, 3,658,520, 4,232,103, 4,175,961 and 4,012,376, JP-B-49-35702 and 39-27577, JP-A-55-144250, 56-119132 and 56-22437, DE1,110,518, and others), amino-substituted chalcone derivatives (see U.S. Pat. No. 3,526,501, and others), oxazole derivatives (ones disclosed in U.S. Pat. No. 3,257,203, and others), styrylanthracene derivatives (see JP-A-56-46234, and others), fluorenone derivatives (JP-A-54-110837, and others), hydrazone derivatives (see U.S. Pat. No. 3,717,462, JP-A-54-59143, 55-52063, 55-52064, 55-46760, 55-85495, 57-11350, 57-148749 and 2-311591, and others), stilbene derivatives (see JP-A-61-210363, 61-228451, 61-14642, 61-72255, 62-47646, 62-36674, 62-10652, 62-30255, 60-93455, 60-94462, 60-174749 and 60-175052, and others), silazane derivatives (U.S. Pat. No. 4,950,950), polysilanes (JP-A-2-204996), aniline copolymers (JP-A-2-282263), and electroconductive high molecular oligomers (in particular thiophene oligomers) disclosed in JP-A-1-211399.

In addition, an inorganic compound such as p-type Si and p-type SiC can be used as the hole-injecting material.

As the material for the hole-injecting and transporting layer, a cross-linkable material can be used. As a cross-linkable hole-injecting and transporting layer, a layer obtained by allowing a cross-linking agent disclosed in Chem. Mater. 2008, 20, 413-422, Chem. Mater. 2011, 23(3), 658-681, WO2008108430, WO2009102027, WO2009123269, WO2010016555, WO2010018813 or the like to be insoluble by heat, light or the like can be given.

[Electron-injecting Layer and Electron-transporting Layer]

The electron-injecting and transporting layer is a layer which helps injection of electrons to the emitting layer and transports the electrons to the emission region, and has a large electron mobility.

Further, it is known that, in an organic EL device, since emitted light is reflected by an electrode (the cathode, for example), light which is directly outcoupled from the anode interferes with light outcoupled after being reflected by the electrode. In order to utilize this interference effect efficiently, the film thickness of the electron-injecting and transporting layer is appropriately selected in a range of several nm to several μm. If the thickness is large, in particular, in order to avoid an increase in voltage, it is preferred that the electron mobility be at least $10^{-5}$ cm$^2$/Vs or more when an electric field of $10^4$ to $10^6$ V/cm is applied.

As the electron-transporting material used in the electron-injecting and transporting layer, an aromatic heterocyclic compound having one or more hetero atoms within the molecule is preferably used.

In particular, a nitrogen-containing ring derivative is preferable. As the nitrogen-containing ring derivative, an aromatic ring having a nitrogen-containing six-membered ring or a five-membered ring skeleton or a fused aromatic ring compound having a nitrogen-containing six-membered ring or five-membered ring skeleton are preferable.

[Interlayer Insulating Film]

The interlayer insulating film in the organic EL multicolor light-emitting apparatus of the invention is mainly used for separating each emitting device (emitting layer). In addition, it is used for flattening the edge of a highly-precise electrode and for electric insulation (prevention of short circuit) between a lower electrode and an upper electrode of an organic EL device.

As the constitution material used for the interlayer insulating film, normally, an organic material such as an acrylic resin, a polycarbonate resin and a polyimide resin and an inorganic oxide such as silicon oxide ($SiO_2$ or $SiO_x$), aluminum oxide ($A_2O_3$ or $AlO_x$), titanium oxide ($TiO_2$), silicon nitrate ($Si_3N_4$), silicon nitride oxide ($SiO_xN_y$) or the like can be given.

It is preferred that the interlayer insulating film be formed by a method in which a photosensitive group is introduced to the above-mentioned constitution material and the material is then processed to have a desired pattern by photolithography or by printing.

[Method for Producing Organic EL Multicolor Light-emitting Apparatus]

Each layer of the organic EL multicolor light-emitting apparatus of the invention can be formed by a known dry film-forming method such as vacuum vapor deposition, sputtering, plasma coating and ion plating and a known wet film-forming method such as spin coating, casting, microgravure coating, photogravure coating, bar coating, roll coating, slit coating, wire bar coating, dip coating, spray coating, screen printing, flexo printing, offset printing, inkjet method and nozzle printing. If a pattern is formed, a method such as screen printing, flexo printing, offset printing and ink jet printing or the like can be applied.

Although there are no particular restrictions are imposed on the film thickness of each layer, it is required to set it to a suitable film thickness. If the film thickness is too large, a large voltage is required to be applied in order to obtain a certain optical output, resulting in poor efficiency. If the film thickness is too small, pinholes or the like are generated, and hence, a sufficient luminance cannot be obtained even if an electric field is applied. The film thickness is normally in the range of 5 nm to 10 μm, with the range of 10 nm to 0.2 μm being further preferable.

As the method for forming the hole-injecting and transporting layer, for example, forming a solution containing an aromatic amine derivative into a film can be mentioned. As the film-forming method, the spin coating method, the casting method, the microgravure coating method, the gravure coating method, the bar coating method, the roll coating method, the slit coating method, the wire bar coating method, the dip coating method, the spray coating method, the screen printing method, the flexo printing method, the offset printing method, the inkjet method, the nozzle printing method or the like can be mentioned. When a pattern is formed, the screen printing method, the flexo printing method, the offset printing method and the ink-jet printing method are preferable. Film formation by these methods can be conducted under conditions which are well known by a person in the art.

After the film formation, the film may be heated under vacuum and dried to remove the solvent. No polymerization reaction by light or heating at high temperatures (200° C. or higher) is necessary. Therefore, deterioration of performance by light or heating at high temperatures can be suppressed.

The solution for forming the hole-injecting and transporting layer may preferably contain at least one kind of an aromatic amine derivative. In addition to the aromatic amine derivative, it may contain a hole-transporting material, an electron-transporting material, an emitting material, an acceptor material, a solvent and an additive such as a stabilizer.

The content of the aromatic amine derivative in the solution for film formation is preferably 20 to 100 wt %, more preferably 51 to 100 wt % relative to the total weight of the composition excluding the solvent. It is preferred that the aromatic amine derivative be a main component of the composition exlcuding the solvent. The amount ratio of the solvent is preferably 1 to 99.9 wt % relative to the solution for film formation, with 80 to 99 wt % being more preferable.

In the meantime, the "main component" means that the content of the aromatic amine derivative is 50 mass % or more.

The solution for film formation may contain an additive for controlling the viscosity and/or the surface tension, for example, a thickener (a high molecular compound, a poor solvent for the aromatic amine derivative, or the like), a viscosity reducing agent (a low-molecular compound or the like), a surfactant or the like. In order to improve storage stability, an antioxidant which does not affect the performance of the organic EL device, such as a phenol-based antioxidant and a phosphorus-based antioxidant may be contained.

Examples of the solvent for the solution for film formation include chlorine-based solvents such as chloroform, methylene chloride, 1,2-dichloroethane, 1,1,2-trichloroethane, chlorobenzene and o-dichlorobenzene; ether-based solvents such as tetrahydrofuran, dioxane, dioxolane, and anisole; aromatic hydrocarbon solvents such as toluene and xylene; aliphatic hydrocarbon-based solvents such as cyclohexane, methylcyclohexane, n-pentane, n-hexane, n-heptane, n-octane, n-nonane and n-decane; ketone-based solvents such as acetone, methyl ethyl ketone, cyclohexanone, benzophenone and acetophenone: ester-based solvents such as ethyl acetate, butyl acetate, ethyl cellosolve acetate, methyl benzoate and phenyl acetate; polyvalent alcohols such as ethylene glycol, ethylene glycol monobutyl ether, ethylene glycol monoethyl ether, ethylene glycol monomethyl ether, dimethoxyethane, propylene glycol, diethoxymethane, triethylene glycol monoethyl ether, glycerin and 1,2-hexanediol and derivatives thereof; alcohol-based solvents such as methanol, ethanol, propanol, isopropanol and cyclohexanol; sulfoxide-based solvents such as dimethylsulfoxide; and amide-based solvents such as N-methyl-2-pyrrolidone and N,N-dimethylformamide. These organic solvents may be used alone or in combination of two or more.

Among these, in respect of solubility, homogeneity of a coating film, viscosity properties or the like, aromatic hydrocarbon-based solvents, ether-based solvents, aliphatic hydrocarbon-based solvents, ester-based solvents and ketone-based solvents are preferable. Toluene, xylene, ethylbenzene, diethylbenzene, trimethylbenzene, n-propylbenzene, isopropylbenzene, n-butylbenzene, isobutylbenzene, 5-butylbenzene, n-hexylbenzene, cyclohexylbenzene, 1-methylnaphthalene, tetralin, 1,3-dioxane, 1,4-dioxane, 1,3-dioxolane, anisole, ethoxybenzene, cyclohexane, bicyclohexyl, cyclohexenyl cyclohexanone, n-heptylcyclohexane, n-hexylcyclohexane, decaline, methyl benzoate, cyclohexanone, 2-propylcyclohexanone, 2-heptanone, 3-heptanone, 4-heptanone, 2-octanone, 2-nonanone, 2-decanone, dicyclohexylketone, acetophenone and benzophenone are preferable.

As the step for color coding when the emitting layer, the hole-injecting and transporting layer or the like are formed by patterning, it is desirable to conduct color coding by using the above-mentioned coating method. The color coding method is not limited to this, and color coding can be conducted by a known method. In addition to the coating method, a pattern may be formed by using a metal mask. Further, a pattern may be formed by the laser transfer method disclosed in JP-A-2003-229258 or JP-A-2004-200170.

By using various materials and the layer forming method mentioned above, a first light-emitting device having a configuration of anode/hole-injecting layer/hole-transporting layer/first emitting layer/first adjacent layer/second electron-transporting layer/first electron-transporting layer/cathode, for example, and a second light-emitting device having a configuration of anode/hole-injecting layer/hole-transporting layer/second adjacent layer/second emitting layer/first electron-transporting layer/cathode, whereby the organic EL multicolor light-emitting apparatus of the invention can be fabricated. Further, the organic EL device can be fabricated in the order of film formation reverse to that mentioned above from the cathode to the anode. The hole-injecting layer and the hole-transporting layer do not necessarily have a configuration in which different two layers are stacked. They may be replaced by a single layer using the material which functions as the hole-injecting and transporting layer.

In particular, in the organic EL multicolor light-emitting apparatus of the invention, since the adjacent layer compound is an organic EL material which is suited to a hybrid connecting layer (HCL) which is present in the boundary of a coating layer and a deposition layer, a hybrid organic EL multicolor light-emitting device in which a coating layer which is capable of forming a large-sized screen at a low cost and a high-performance deposition layer are combined can be fabricated.
EXAMPLES
In Examples and Comparative Examples, organic EL devices were fabricated by using the following compounds.
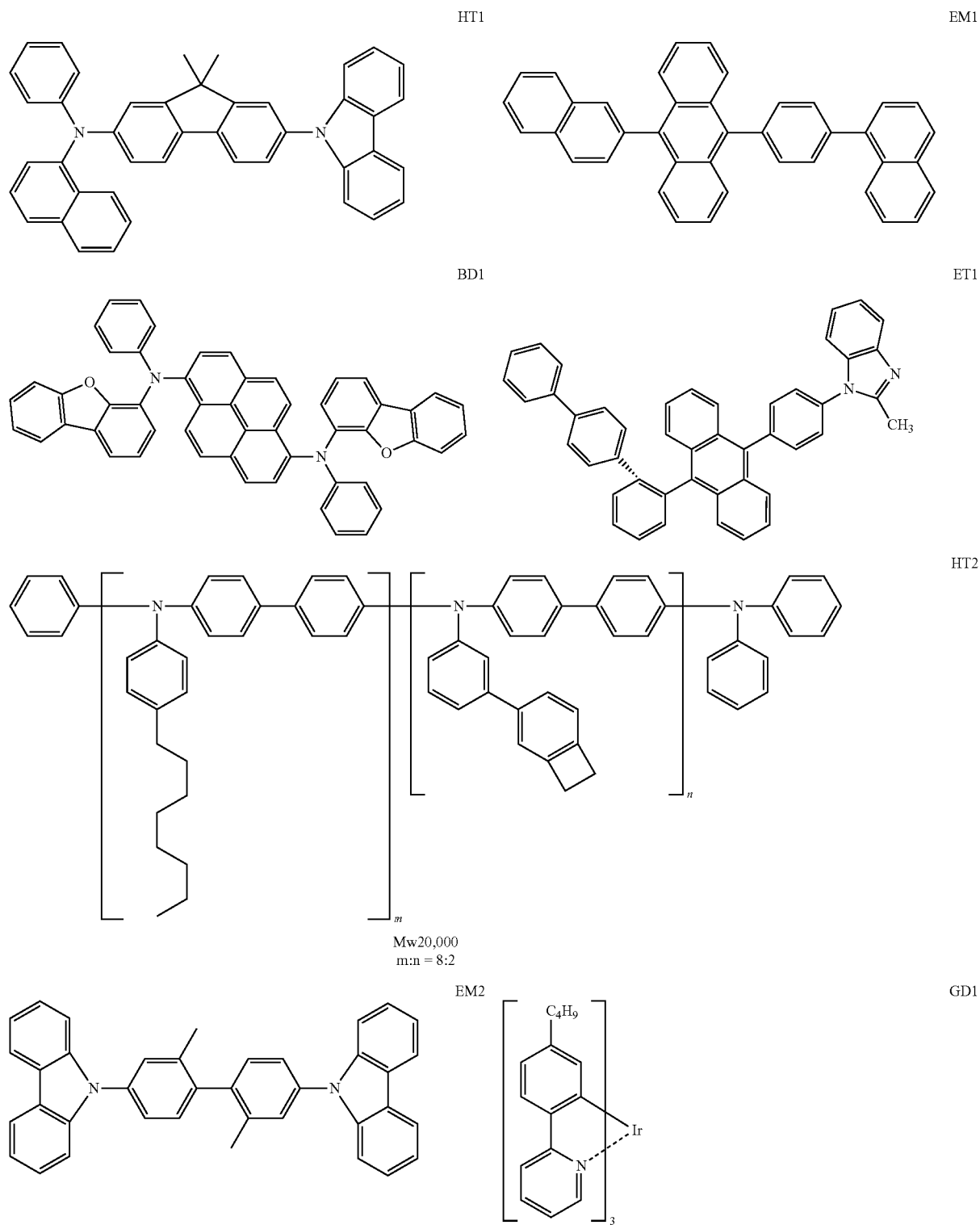

-continued
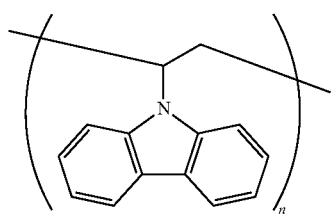
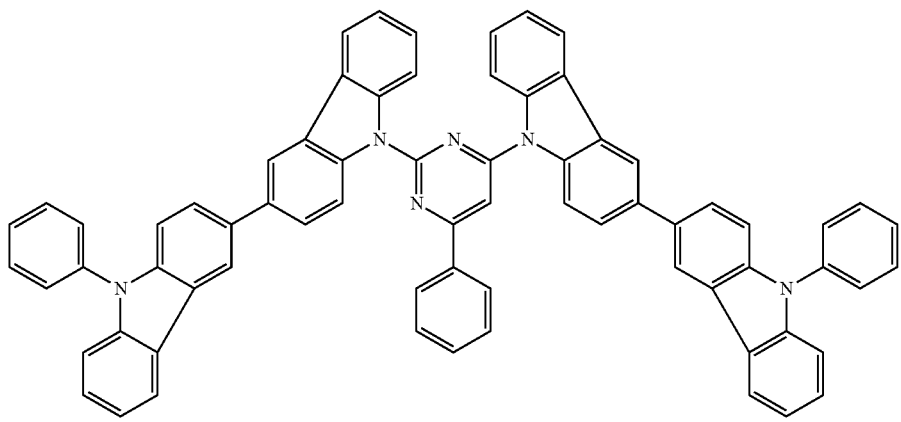
EM3
EM4
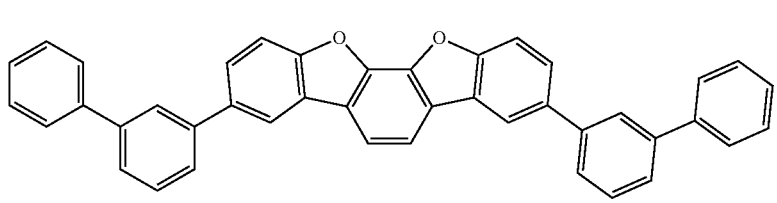
Compound 1
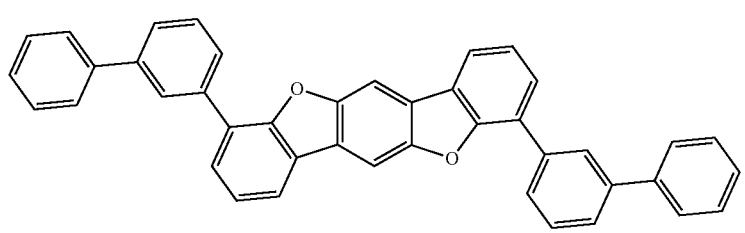
Compound 2
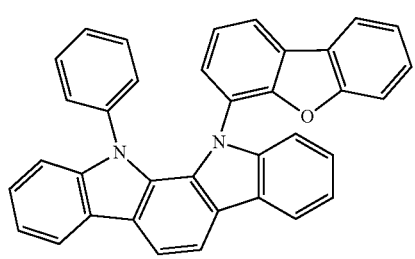
Compound 3
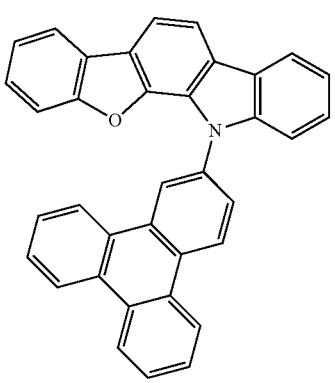
Compound 4

-continued
Compound 5
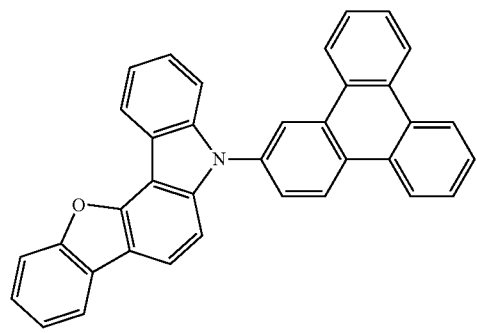
Compound 100
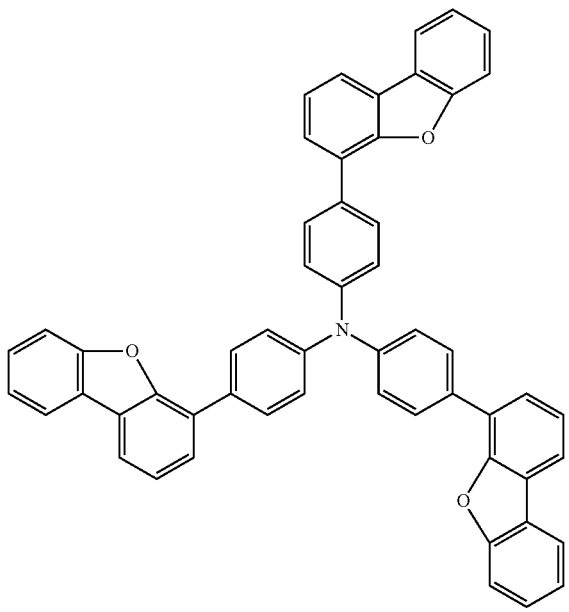
Compound 101
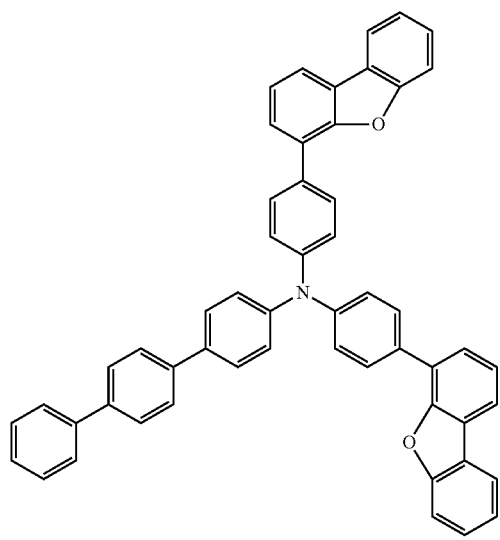
Compound 102
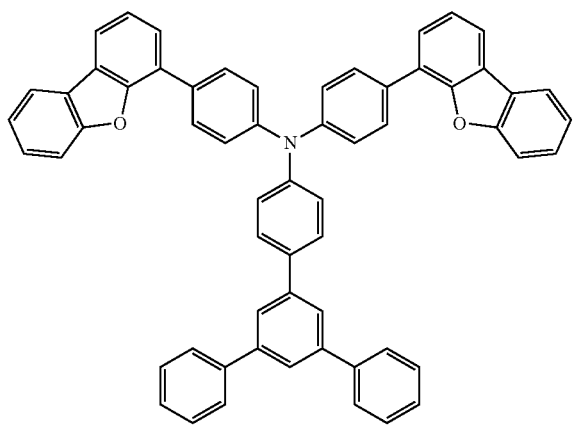
Compound 103
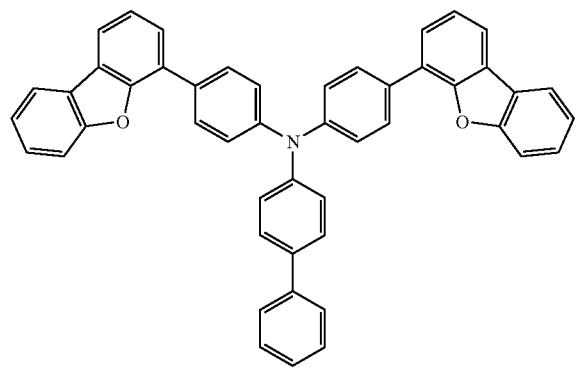
Compound A
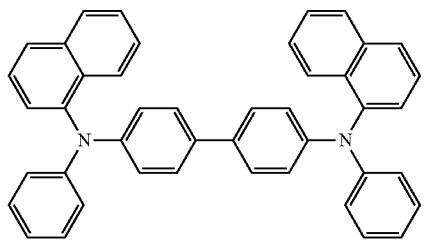

Compound B

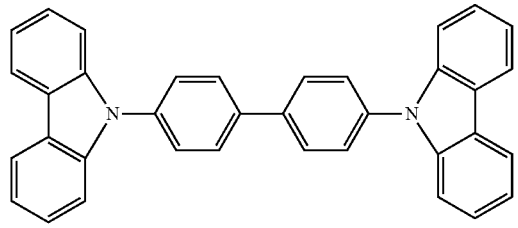

Compound C

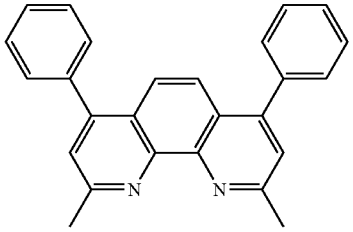

Example 1

In order to confirm the advantageous effects of the organic EL multicolor light-emitting apparatus of the invention, the first light-emitting device and the second light-emitting device were evaluated.

[Fabrication of Second Light-emitting Device (Blue Fluorescent Light-emitting Device)]

A glass substrate measuring 25 mm×75 mm×1.1 mm thick, with an ITO transparent electrode, was subjected to ultrasonic cleaning in isopropyl alcohol for 5 minutes and then to UV ozone cleaning for 30 minutes. On the thus cleaned glass substrate with the transparent electrode, ND1501 (aniline oligomer manufactured by Nissan Chemical Industries, Ltd.) was formed into a 25 nm-thick film by the spin coating method. The film was heated at 230° C. to form a hole-injecting layer. Subsequently, a xylene solution (1.0 wt %) of HT1 was formed into a film of 30 nm by the spin coating method, dried at 120° C., whereby a hole-transporting layer was formed. Subsequently, as the material for the second adjacent layer (second organic layer), compound 1 was deposited in a thickness of 5 nm by deposition, and then compound 100 was deposited in a thickness of 5 nm, whereby a 10 nm-thick film was formed. Then, as the second emitting layer (blue-emitting layer) (third organic layer), EM1 (host material) and BD1 (dopant material) were deposited at a mass ratio of 97:3, whereby a 35 nm-thick emitting layer was formed. Further, ET1 was formed into a 25 nm-thick film by deposition. This layer functions as the electron-transporting layer. Thereafter, Li as the reductive dopant (Li source: manufactured by SAES Getters) and tris(8-hydroxyquinolinato)aluminum (Alq) were co-deposited to form an Alq:Li film (film thickness: 10 nm) as the electron-injecting layer. On this Alq:Li film, metal Al was deposited to form a metal cathode, and glass-sealed in nitrogen, whereby a blue-emitting organic EL device as the second light-emitting device was fabricated.

Current (10 mA/cm$^2$) was flown to the thus fabricated second light-emitting device to evaluate the performance. The light-emitting device emitted blue light, and the luminous efficiency was 5.1 cd/A, and the period of time from the start of operation until the luminance was reduced by 20% (LT80) was 140 hours at 50° C. and 25 mA/cm$^2$. The results are shown in Table 1.

[Fabrication of First Light-emitting Device (Green Phosphorescent Light-emitting Device: Low-molecular light-emitting Layer)]

A glass substrate measuring 25 mm×75 mm×1.1 mm thick, with an ITO transparent electrode, was subjected to ultrasonic cleaning in isopropyl alcohol for 5 minutes and then to UV ozone cleaning for 30 minutes. On the thus cleaned glass substrate with the transparent electrode, ND1501 (manufactured by Nissan Chemical Industries, Ltd.) was formed into a 25 nm-thick film by the spin coating method. The film was heated at 230° C. to form a hole-injecting layer. Subsequently, a xylene solution (1.0 wt %) of HT2 disclosed in WO2009/102027 was formed into a film of 30 nm by the spin coating method, heated and dried at 230° C., whereby a hole-transporting layer was formed. Subsequently, as the first emitting layer (green emitting layer) (first organic layer), a xylene solution (1.0 wt %) of EM2 (host material) and GD1 (dopant material) (weight ratio: 90:10) was prepared, and formed into a 60 nm-film by spin coating. The film was dried at 120° C. Subsequently, as the first adjacent layer (second organic layer), as in the case of the material for the second adjacent layer, compound 1 was deposited in a thickness of 5 nm, and then compound 100 was deposited in a thickness of 5 nm, whereby a 10 nm-thick film was formed. Subsequently, EM1 (host material) and BD1 (dopant material) were deposited in a ratio of 97:3, whereby a layer with a thickness of 35 nm (blue common layer) (third organic layer) was formed. Then, ET1 was formed into a 25 nm-thick film by deposition. These layers function as an electron-transporting layer. Thereafter, Li as the reductive dopant (Li source: manufactured by SAES Getters) and Alq were co-deposited to form an Alq:Li film (film thickness: 10 nm) as the electron-injecting layer. On this Alq:Li film, metal Al was deposited to form a metal cathode, and glass-sealed in nitrogen, whereby a green-emitting organic EL device as the first light-emitting device was fabricated.

Current (1 mA/cm$^2$) was flown to the thus fabricated first light-emitting device to evaluate the performance. The light-emitting device emitted green light, and the luminous efficiency was 58 cd/A. Further, current (0.1 to 30 mA/cm$^2$) was flown to the first light-emitting device to confirm a change in chromaticity of emitted color. As a result, it was found that a change in CIE-x (Δx) was 0.010 and a change in CIE-y (Δy) was 0.012. The results are shown in Table 1.

TABLE 1

| | | Second light-emitting device (blue) | | | First light-emitting device (green) | | | |
|---|---|---|---|---|---|---|---|---|
| | Adjacent layer | Emitting layer Host | Luminous efficiency (cd/A) | Life (hr) | Emitting layer Host | Luminous efficiency (cd/A) | Change in chromaticity Δx | Change in chromaticity Δx |
| Ex. 1 | Compound 1/Compound 100 | EM1 | 5.1 | 140 | EM2 | 58 | 0.010 | 0.012 |
| Ex. 2 | Compound 2/Compound 100 | ↑ | 5.3 | 210 | ↑ | 58 | 0.012 | 0.013 |
| Ex. 3 | Compound 3/Compound 100 | ↑ | 6.1 | 100 | ↑ | 52 | 0.018 | 0.023 |
| Ex. 4 | Compound 4/Compound 100 | ↑ | 5.4 | 160 | ↑ | 57 | 0.011 | 0.012 |
| Ex. 5 | Compound 5/Compound 100 | ↑ | 5.1 | 200 | ↑ | 55 | 0.015 | 0.018 |
| Ex. 6 | Compound 1/Compound 101 | ↑ | 5.5 | 150 | ↑ | 59 | 0.011 | 0.013 |
| Ex. 7 | Compound 2/Compound 101 | ↑ | 5.5 | 200 | ↑ | 59 | 0.010 | 0.011 |
| Ex. 8 | Compound 3/Compound 101 | ↑ | 5.7 | 90 | ↑ | 52 | 0.017 | 0.021 |
| Ex. 9 | Compound 4/Compound 101 | ↑ | 5.5 | 180 | ↑ | 57 | 0.011 | 0.012 |
| Ex. 10 | Compound 5/Compound 101 | ↑ | 5.1 | 180 | ↑ | 56 | 0.012 | 0.014 |
| Ex. 11 | Compound 1/Compound 102 | ↑ | 5.8 | 170 | ↑ | 58 | 0.007 | 0.005 |
| Ex. 12 | Compound 2/Compound 102 | ↑ | 6.4 | 280 | ↑ | 58 | 0.009 | 0.007 |
| Ex. 13 | Compound 3/Compound 102 | ↑ | 6.7 | 200 | ↑ | 53 | 0.012 | 0.018 |
| Ex. 14 | Compound 4/Compound 102 | ↑ | 5.0 | 120 | ↑ | 57 | 0.011 | 0.012 |
| Ex. 15 | Compound 5/Compound 102 | ↑ | 5.2 | 200 | ↑ | 55 | 0.012 | 0.014 |
| Ex. 16 | Compound 1/Compound 103 | ↑ | 6.5 | 120 | ↑ | 58 | 0.010 | 0.012 |
| Ex. 17 | Compound 2/Compound 103 | ↑ | 6.5 | 280 | ↑ | 59 | 0.012 | 0.013 |
| Ex. 18 | Compound 3/Compound 103 | ↑ | 6.4 | 200 | ↑ | 52 | 0.016 | 0.021 |
| Ex. 19 | Compound 4/Compound 103 | ↑ | 5.4 | 100 | ↑ | 57 | 0.009 | 0.010 |
| Ex. 20 | Compound 5/Compound 103 | ↑ | 5.9 | 190 | ↑ | 55 | 0.013 | 0.014 |

Examples 2 to 20

A first light-emitting device and a second light-emitting device were producedd and evaluated in the same manner as in Example 1, except that, in Example 1, the first adjacent layer and the second adjacent layer were formed by using compounds shown in Table 1 instead of using compounds 1 and 100. The results are shown in Table 1.

Example 21

[Fabrication of Second Light-emitting Device (Blue Fluorescent Light-emitting Device)]
In the same manner as in Example 1, a blue-emitting organic EL device as the second light-emitting device was fabricated. The results are shown in Table 2.
[Fabrication of First Light-emitting Device (Green Phosphorescent Light-emitting Device: High-molecular Emitting Layer]
A glass substrate measuring 25 mm×75 mm×1.1 mm thick, with an ITO transparent electrode, was subjected to ultrasonic cleaning in isopropyl alcohol for 5 minutes and then to UV ozone cleaning for 30 minutes. On the thus cleaned glass substrate with the transparent electrode, ND1501 (manufactured by Nissan Chemical Industries, Ltd.) was formed into a 25 nm-thick film by the spin coating method. The film was heated at 230° C. to form a hole-injecting layer. Subsequently, a xylene solution (1.0 wt %) of HT2 was formed into a film of 30 nm by the spin coating method, dried at 230° C., whereby a hole-transporting layer was formed. Then, as the first emitting layer (green emitting layer) (first organic layer), as the host material, a xylene solution (1.0 wt %) of EM3 (host material) (weight-average molecular weight: 700000) and GD1 (dopant material) (weight ratio of 90:10) was prepared, and formed into a 60 nm-thick film by spin coating. The film was dried at 120° C. Subsequently, as the first adjacent layer (second organic layer), as in the case of the material for the second adjacent layer, compound 1 was deposited in a thickness of 5 nm, and then compound 100 was deposited in a thickness of 5 nm, whereby a 10 nm-thick film was formed. Subsequently, EM1 (host material) and BD1 (dopant material) were deposited in a ratio of 97:3, whereby a layer with a thickness of 35 nm (blue common layer) (third organic layer) was formed. Then, ET1 was formed into a 25 nm-thick film by deposition. These layers function as an electron-transporting layer. Thereafter, Li as the reductive dopant (Li source: manufactured by SAES Getters) and Alq were co-deposited to form an Alq:Li film (film thickness: 10 nm) as the electron-injecting layer. On this Alq:Li film, metal Al was deposited to form a metal cathode, and glass-sealed in nitrogen, whereby a green-emitting organic EL device as the first light-emitting device was fabricated.

Current (1 mA/cm$^2$) was flown to the thus fabricated first light-emitting device to evaluate the performance. The light-emitting device emitted green light, and the luminous efficiency was 49 cd/A. Further, current (0.1 to 30 mA/cm$^2$) was flown to the first light-emitting device to confirm a change in chromaticity of emitted color. As a result, it was found that a change in CIE-x (Δx) was 0.015 and a change in CIE-y (Δy) was 0.017. The results are shown in Table 2.

TABLE 2

| | | Second light-emitting device (blue) | | | First light-emitting device (green) | | | |
|---|---|---|---|---|---|---|---|---|
| | Adjacent layer | Emitting layer Host | Luminous efficiency (cd/A) | Life (hr) | Emitting layer Host | Luminous efficiency (cd/A) | Change in chromaticity Δx | Change in chromaticity Δx |
| Ex. 21 | Compound 1/Compound 100 | EM1 | 5.1 | 140 | EM3 | 49 | 0.015 | 0.017 |
| Ex. 22 | Compound 2/Compound 100 | ↑ | 5.3 | 210 | ↑ | 47 | 0.013 | 0.014 |
| Ex. 23 | Compound 3/Compound 100 | ↑ | 6.1 | 100 | ↑ | 44 | 0.016 | 0.021 |

TABLE 2-continued

|  | | Second light-emitting device (blue) | | | First light-emitting device (green) | | | |
| --- | --- | --- | --- | --- | --- | --- | --- | --- |
|  | Adjacent layer | Emitting layer Host | Luminous efficiency (cd/A) | Life (hr) | Emitting layer Host | Luminous efficiency (cd/A) | Change in chromaticity Δx | Change in chromaticity Δx |
| Ex. 24 | Compound 4/Compound 100 | ↑ | 5.4 | 160 | ↑ | 48 | 0.013 | 0.015 |
| Ex. 25 | Compound 5/Compound 100 | ↑ | 5.1 | 200 | ↑ | 49 | 0.015 | 0.018 |
| Ex. 26 | Compound 1/Compound 102 | ↑ | 5.8 | 170 | ↑ | 49 | 0.013 | 0.013 |
| Ex. 27 | Compound 2/Compound 102 | ↑ | 6.4 | 280 | ↑ | 48 | 0.012 | 0.013 |
| Ex. 28 | Compound 3/Compound 102 | ↑ | 6.7 | 200 | ↑ | 49 | 0.023 | 0.025 |
| Ex. 29 | Compound 4/Compound 102 | ↑ | 5.0 | 120 | ↑ | 49 | 0.015 | 0.016 |
| Ex. 30 | Compound 5/Compound 102 | ↑ | 5.2 | 200 | ↑ | 44 | 0.018 | 0.020 |
| Ex. 31 | Compound 1/Compound 100 | ↑ | 5.1 | 140 | EM4 | 63 | 0.008 | 0.009 |
| Ex. 32 | Compound 2/Compound 100 | ↑ | 5.3 | 210 | ↑ | 61 | 0.010 | 0.009 |
| Ex. 33 | Compound 3/Compound 100 | ↑ | 6.1 | 100 | ↑ | 53 | 0.019 | 0.021 |
| Ex. 34 | Compound 4/Compound 100 | ↑ | 5.4 | 160 | ↑ | 60 | 0.008 | 0.009 |
| Ex. 35 | Compound 5/Compound 100 | ↑ | 5.1 | 200 | ↑ | 59 | 0.013 | 0.015 |
| Ex. 36 | Compound 1/Compound 102 | ↑ | 5.8 | 170 | ↑ | 62 | 0.008 | 0.009 |
| Ex. 37 | Compound 2/Compound 102 | ↑ | 6.4 | 280 | ↑ | 62 | 0.011 | 0.012 |
| Ex. 38 | Compound 3/Compound 102 | ↑ | 6.7 | 200 | ↑ | 51 | 0.018 | 0.022 |
| Ex. 39 | Compound 4/Compound 102 | ↑ | 5.0 | 120 | ↑ | 58 | 0.009 | 0.010 |
| Ex. 40 | Compound 5/Compound 102 | ↑ | 5.2 | 200 | ↑ | 60 | 0.015 | 0.017 |

Examples 22 to 30

A first light-emitting device and an a second light-emitting device were produced and evaluated in the same manner as in Example 21, except that, in Example 21, the first adjacent layer and the second adjacent layer were formed by using compounds shown in Table 2 instead of using compounds 1 and 100. The results are shown in Table 2.

Example 31

[Fabrication of Second Light-emitting Device (Blue Fluorescent Emitting Device)]

A blue emitting organic EL device as the second light-emitting device was fabricated in the same manner as in Example 1. The results are shown in Table 2.

[Fabrication of First Light-emitting Device (Green Phosphorescent Emitting Device: Mid-molecular Weight Light-emitting Layer)]

A glass substrate measuring 25 mm×75 mm×1.1 mm thick, with an ITO transparent electrode, was subjected to ultrasonic cleaning in isopropyl alcohol for 5 minutes and then to UV ozone cleaning for 30 minutes. On the thus cleaned glass substrate with the transparent electrode, ND1501 (manufactured by Nissan Chemical Industries, Ltd.) was formed into a 25 nm-thick film by the spin coating method. The film was heated at 230° C. to form a hole-injecting layer. Subsequently, a xylene solution (1.0 wt %) of HT2 was formed into a film of 30 nm by the spin coating method, dried at 230° C., whereby a hole-transporting layer was formed. Then, as the first emitting layer (green emitting layer) (first organic layer), a xylene solution (1.0 wt %) of EM4 (host material) and GD1 (dopant material) (90:1) was prepared, and formed into a 60 nm-thick film by spin coating. The film was dried at 120° C. Subsequently, as the first adjacent layer (second organic layer), as in the case of the material for the second adjacent layer, compound 1 was deposited in a thickness of 5 nm, and then compound 100 was deposited in a thickness of 5 nm, whereby a 10 nm-thick film was formed. Subsequently. EM1 (host material) and BD1 (dopant material) were deposited in a ratio of 97:3, whereby a layer with a thickness of 35 nm (blue common layer) (third organic layer) was formed. Then, ET1 was formed into a 25 nm-thick film by deposition. These layers function as an electron-transporting layer. Thereafter, Li as the reductive dopant (Li source: manufactured by SAES Getters) and Alq were co-deposited to form an Alq:Li film (film thickness: 10 nm) as the electron-injecting layer. On this Alq:Li film, metal Al was deposited to form a metal cathode, and glass-sealed in nitrogen, whereby a green-emitting organic EL device as the first light-emitting device was fabricated.

Current (1 mA/cm$^2$) was flown to the thus fabricated first light-emitting device to evaluate the performance. The light-emitting device emitted green light, and the luminous efficiency was 63 cd/A. Further, current (0.1 to 30 mA/cm$^2$) was flown to the first light-emitting device to confirm a change in chromaticity of emitted color. As a result, it was found that a change in CIE-x (Δx) was 0.008 and a change in CIE-y (Δy) was 0.009. The results are shown in Table 2.

Examples 32 to 40

A first light-emitting device and a second light-emitting device were produced and evaluated in the same manner as in Example 31, except that, in Example 31, the first adjacent layer and the second adjacent layer were formed by using compounds shown in Table 2 instead of using compounds 1 and 100. The results are shown in Table 2.

Comparative Examples 1 to 4

A first light-emitting device and a second light-emitting device were produced and evaluated in the same manner as in Example 1, except that the first adjacent layer and the second adjacent layer, which were a single layer, were formed by using the compounds (A to C) shown in Table 3 and the compound 100 alone Instead of the compounds 1 and 100 in Example 1. The results are shown in Table 3.

TABLE 3

| | | Second light-emitting device (blue) | | | First light-emitting device (green) | | | |
|---|---|---|---|---|---|---|---|---|
| | Adjacent layer | Emitting layer Host | Luminous efficiency (cd/A) | Life (hr) | Emitting layer Host | Luminous efficiency (cd/A) | Change in chromaticity Δx | Change in chromaticity Δx |
| Comp. Ex. 1 | Compound A | EM1 | 4.8 | 80 | EM2 | 48 | 0.072 | 0.165 |
| Comp. Ex. 2 | Compound B | ↑ | 2.4 | 1 | — | — | — | — |
| Comp. Ex. 3 | Compound C | ↑ | 0.2 | 1 | — | — | — | — |
| Comp. Ex. 4 | Compound 100 | ↑ | 7.0 | 250 | EM2 | 53 | 0.025 | 0.060 |

From the results shown above, the following was confirmed. In Examples 1 to 40, the second light-emitting device (blue light-emitting device) had a high efficiency and a long life. Further, in the first light-emitting device (green light-emitting device), blue emission hardly appeared in green emission, and a change in chromaticity by current was small, and luminous efficiency of green light was high. In addition, dependency of the host material in the emitting layer (low molecular, mid molecular or high molecular) was small, and hence, a highly efficient, long-lived and high-quality organic EL multicolor light-emitting apparatus was fabricated.

The adjacent layer (second organic layer) formed of the material of the invention was, when used in the second light-emitting device (blue light-emitting device), excellent in properties of injecting and transporting holes to the emitting layer, and had a high efficiency. In addition, due to high resistance to holes and electrons, it is assumed that it have a long life and have excellent performance. When used in the first light-emitting device (green emitting device), it exhibited effects of maintaining a high triplet energy, could prevent diffusion of triplet energy from the red, yellow phosphorescent emitting layer or the green phosphorescent emitting layer to the blue-emitting layer, and hence, blue emission hardly appears in green emission. Therefore, it is assumed that change in chromaticity by current be small, and a high efficiency can be obtained.

On the other hand, in Comparative Examples 2 and 3, the efficiency of the second light-emitting device (blue light-emitting device) was low, and the life was significantly short, and as a result, it was impossible to fabricate a highly efficient, long-lived and high-quality organic EL multicolor light-emitting apparatus.

In Comparative Examples 1 and 4, the efficiency of the second light-emitting device (blue emitting device) was high, and the life thereof was relatively long. In the first light-emitting device (green emitting device), blue emission appeared in green emission, a change in chromaticity by current was large, blue emission was poorly-balanced with green emission, and as a result, a high-quality organic EL multicolor light-emitting apparatus could not be fabricated. The reason therefor is assumed to be diffusion of the triplet energy of the green emitting layer of the first light-emitting device (green emitting device) to the common blue-emitting layer through compound A or 100.

INDUSTRIAL APPLICABILITY

The organic EL multicolor emitting apparatus of the invention can be preferably used in a display for use in commercial or industrial purposes and color displays or the like, and they can be preferably used in a flat panel TV, a note PC, a mobile phone, a display of a game machine, a car-mounted TV or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The specification of the Japanese application claiming priority under the Paris Convention are incorporated herein by reference in its entirety.

The invention claimed is:

1. An organic electroluminescence multicolor light-emitting apparatus comprising:
   a substrate; and
   a first light-emitting device and a second light-emitting device being arranged in parallel on the surface of the substrate;
   wherein the first light-emitting device comprises, between an anode and a cathode, a first organic layer, a second organic layer and a third organic layer in this sequence from the anode side in a direction perpendicular to the surface of the substrate,
   the second light-emitting device comprises, between an anode and a cathode, a second organic layer and a third organic layer in this sequence from the anode side in a direction perpendicular to the surface of the substrate,
   the first organic layer comprises a first emitting dopant,
   the third organic layers comprise a second emitting dopant, and
   the second organic layers independently comprise any one of compounds represented by the following formulas (1) to (6):

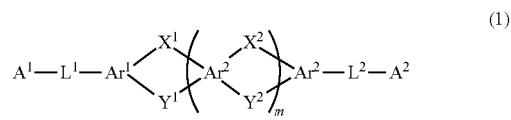

(1)

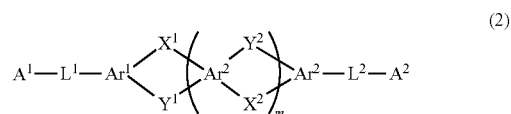

(2)

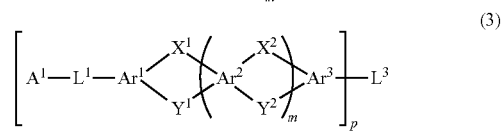

(3)

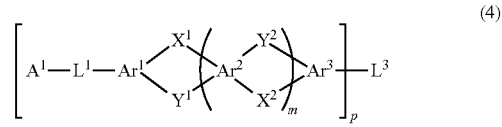

(4)

-continued

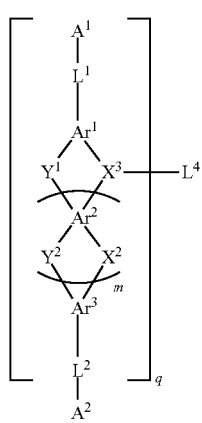

(5)

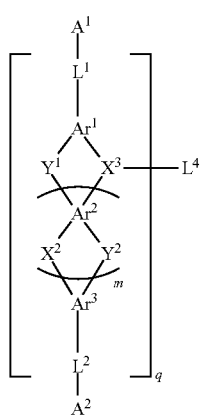

(6)

wherein in the formulas (1) to (6), $Ar^1$, $Ar^2$ and $Ar^3$ are independently a substituted or unsubstituted aromatic hydrocarbon group including 6 ring carbon atoms or a substituted or unsubstituted aromatic heterocyclic group including 6 ring atoms;

in the formulas (1) to (4), $X^1$ is oxygen (O), sulfur (S), >$CR^2R^3$, >$BR^4$, >$SiR^5R^6$, >$C=NR^7$, >$C=CR^8R^9$, >S=O, >$SO_2$, >$PR^{10}$ or >$P(=O)R^{11}$; $X^2$ is oxygen (O), sulfur (S), >N—$R^1$, >$CR^2R^3$, >$SiR^5R^6$, >$C=NR^7$, >$C=CR^8R^9$, >S=O, >$SO_2$, >$PR^{10}$ or >$P(=O)R^{11}$; and $Y^1$ is a single bond, oxygen (O), sulfur (S), >$CR^2R^3$, >$BR^4$, >$SiR^5R^6$, >$C=NR^7$, >$C=CR^8R^9$, >S=O, >$SO_2$, >$PR^{10}$ or >$P(=O)R^{11}$; $Y^2$ is a single bond, oxygen (O), sulfur (S), >N—$R^1$, >$CR^2R^3$, >$BR^4$, >$SiR^5R^6$, >$C=NR^7$, >$C=CR^8R^9$, >S=O, >$SO_2$, >$PR^{10}$ or >$P(=O)R^{11}$;

in the formulas (5) and (6), $X^3$ is >$CR^2$, B (boron), >$SiR^5$, phosphorus (P) or >P=O; $X^2$ is oxygen (O), sulfur (S), >N—$R^1$, >$CR^2R^3$, >$BR^4$, >$SiR^5R^6$, >$C=NR^7$, >$C=CR^8R^9$, >S=O, >$SO_2$, >$PR^{10}$ or >$P(=O)R^{11}$; and $Y^1$ is a single bond, oxygen (O), sulfur (S), >$CR^2R^3$, >$BR^4$, >$SiR^5R^6$, >$C=NR^7$, >$C=CR^8R^9$, >S=O, >$SO_2$, >$PR^{10}$ or >$P(=O)R^{11}$; $Y^2$ is a single bond, oxygen (O), sulfur (S), >N—$R^1$, >$CR^2R^3$, >$BR^4$, >$SiR^5R^6$, >$C=NR^7$, >$C=CR^8R^9$, >S=O, >$SO_2$, >$PR^{10}$ or >$P(=O)R^{11}$;

$R^1$ to $R^{11}$ is a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms;

m is an integer of 1 to 3; and p and q are independently an integer of 2 to 4;

in the formulas (1), (2), (5) and (6), $L^1$ and $L^2$ are independently a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (3) and (4), $L^1$ is a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (3) and (4), $L^3$ is, when p is 2, a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (5) and (6), $L^4$ is, when q is 2, a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20 carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

in the formulas (3) and (4), $L^3$ is, when p is 3, a substituted or unsubstituted trivalent saturated hydrocarbon group including 1 to 20 carbon atoms, a substituted or unsubstituted trivalent cyclic saturated hydrocarbon group including 3 to 20 carbon atoms, a trivalent silyl group or a trivalent substituted silyl group including 3 to 20 carbon atoms, a substituted or unsubstituted trivalent aromatic hydrocarbon group including 6 to 30 ring carbon atoms or a substituted or unsubstituted trivalent aromatic heterocyclic group including 5 to 30 ring atoms;

in the formulas (5) and (6), $L^4$ is, when q is 3, a substituted or unsubstituted trivalent saturated hydrocarbon group including 1 to 20 carbon atoms, a substituted or unsubstituted trivalent cyclic saturated hydrocarbon group including 3 to 20 carbon atoms, a trivalent silyl group or a trivalent substituted silyl group including 3 to 20 carbon atoms, a substituted or unsubstituted trivalent aromatic hydrocarbon group including 6 to 30 ring carbon atoms or a substituted or unsubstituted trivalent aromatic heterocyclic group including 5 to 30 ring atoms;

in the formulas (3) and (4), $L^3$ is, when p is 4, a substituted or unsubstituted tetravalent saturated hydrocarbon group including 1 to 20 carbon atoms, a substituted or unsubstituted tetravalent cyclic saturated hydrocarbon group including 3 to 20 carbon atoms, a tetravalent silyl group or a substituted tetravalent silyl group including 3 to 20 carbon atoms, a substituted or unsubstituted tetravalent aromatic hydrocarbon group including 6 to 30 ring carbon atoms or a substituted or unsubstituted tetravalent aromatic heterocyclic group including 5 to 30 ring atoms;

in the formulas (5) and (6), $L^4$ is, when q is 4, a substituted or unsubstituted tetravalent saturated hydrocarbon group including 1 to 20 carbon atoms, a substituted or unsubstituted tetravalent cyclic saturated hydrocarbon group including 3 to 20 carbon atoms, a tetravalent silyl group or a substituted tetravalent silyl group including 3 to 20 carbon atoms, a substituted or unsubstituted tetravalent aromatic hydrocarbon group including 6 to 30 ring carbon atoms or a substituted or unsubstituted tetravalent aromatic heterocyclic group including 5 to 30 ring atoms;

in the formulas (1), (2), (5) and (6), $A^1$ and $A^2$ are independently a hydrogen atom, a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms;

in the formulas (3) and (4), $A^1$ is a hydrogen atom, a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms, or a substituted or unsubstituted aromatic heterocyclic group including 5 to 30 ring atoms.

2. The organic electroluminescence multicolor light-emitting apparatus according to claim 1, wherein m of the compound represented by the formulas (1) to (6) is 1 and $Y^1$ and $Y^2$ are a single bond.

3. The organic electroluminescence multicolor light-emitting apparatus according to claim 1, wherein the compound represented by the formula (1) or (2) is a compound represented by the following formulas (7) to (12):

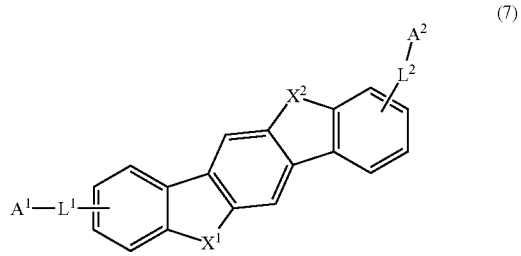

(7)

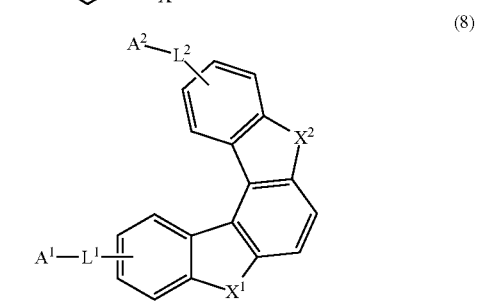

(8)

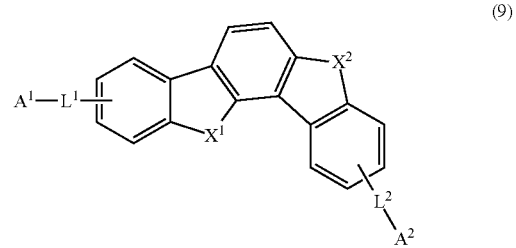

(9)

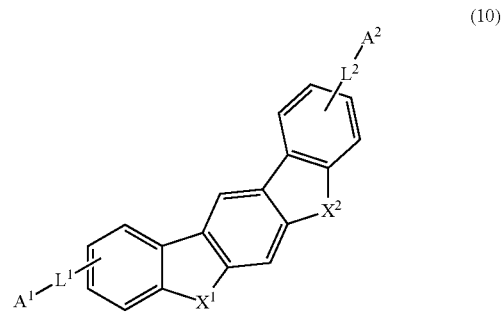

(10)

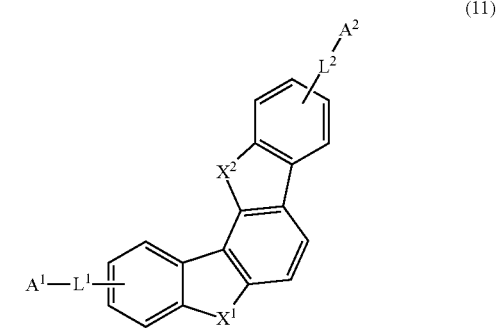

(11)

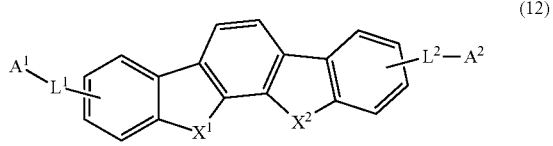

(12)

wherein $A^1$, $A^2$, $L^1$, $L^2$, $X^1$ and $X^2$ are independently the same as $A^1$, $A^2$, $L^1$, $L^2$, $X^1$ and $X^2$ in the formula (1).

4. The organic electroluminescence multicolor light-emitting apparatus according to claim 1, wherein the compound represented by the formula (3) or (4) is a compound represented by the following formulas (13) to (18):

(13)
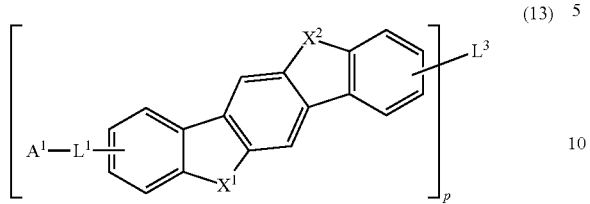

(14)
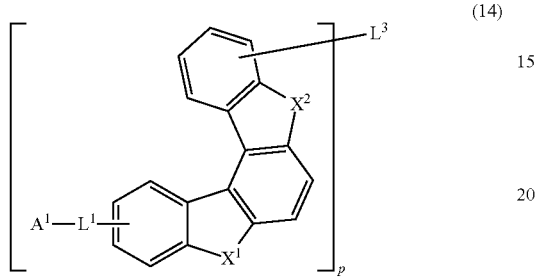

(15)
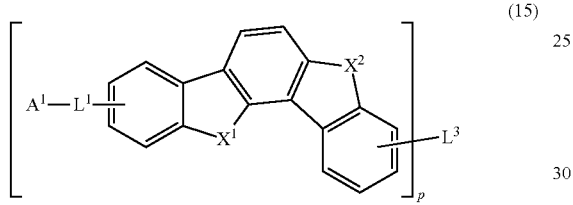

(16)
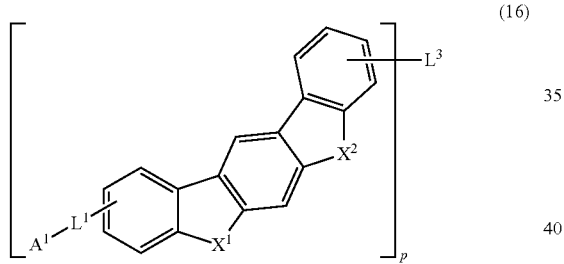

(17)
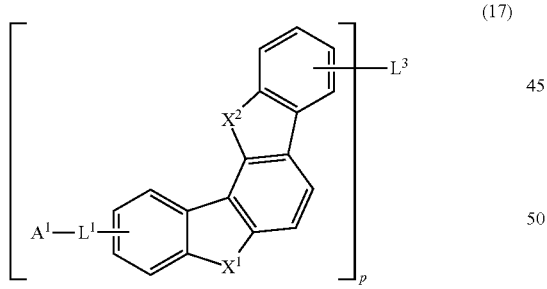

(18)
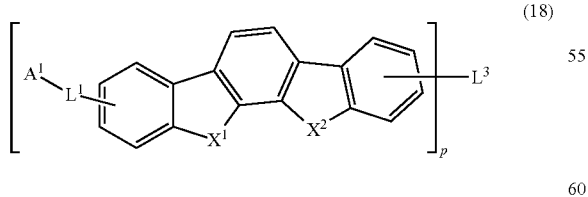

wherein $A^1$, $L^1$, $L^3$, $X^1$, $X^2$ and p are independently the same as $A^1$, $L^1$, $L^3$, $X^1$, $X^2$ and p in the formula (3).

5. The organic electroluminescence multicolor light-emitting apparatus according to claim 1, wherein the compound represented by the formula (5) or (6) is a compound represented by the following formulas (19) to (24):

(19)
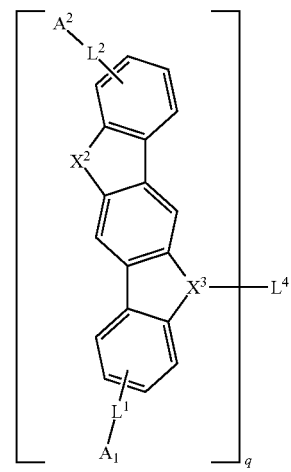

(20)
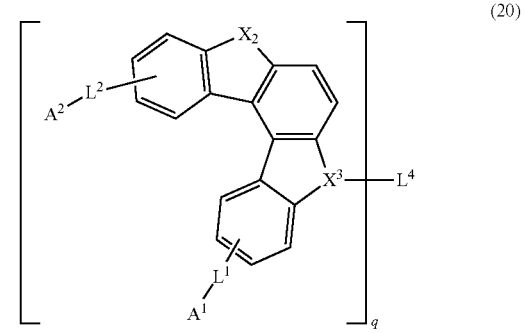

(21)
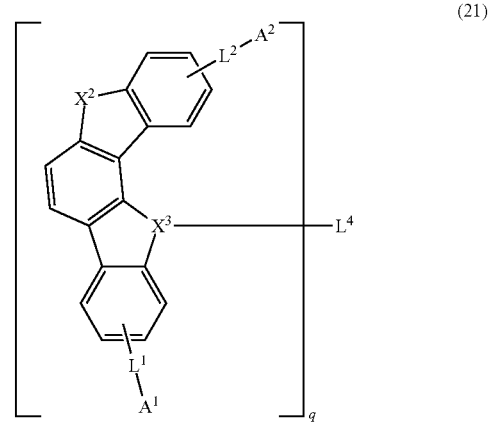

-continued (22)

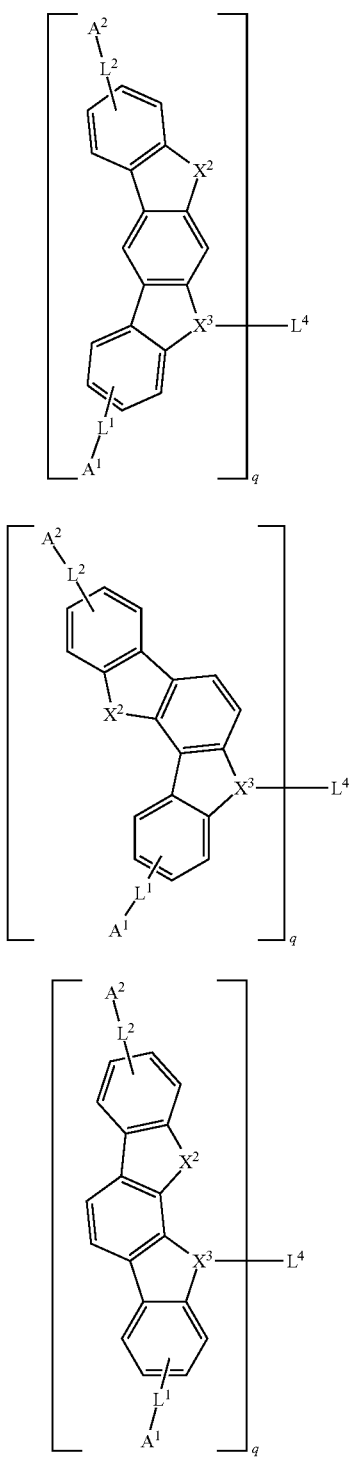

(23)

(24)

wherein $A^1$, $A^2$, $L^1$, $L^2$, $L^4$, $X^2$ $X^3$ and q are independently the same as $A^1$, $A^2$, $L^1$, $L^2$, $L^4$, $X^2$, $X^3$ and q in the formula (5).

6. The organic electroluminescence multicolor light-emitting apparatus according to claim 1, wherein $X^1$ is oxygen (O) or sulfur (S), or $X^2$ is an element or a group selected from oxygen (O), sulfur (S) and >N—$R^1$ (wherein $R^1$ is the same as $R^1$ in the formulas (1) to (6)).

7. The organic electroluminescence multicolor light-emitting apparatus according to claim 6, wherein $X^1$ or $X^2$ is oxygen (O).

8. The organic electroluminescence multicolor light-emitting apparatus according to claim 6, wherein $R^1$ in the >N—$R^1$ is a group including a fused aromatic hydrocarbon skeleton including 10 to 30 ring carbon atoms or a group including an aromatic heterocyclic skeleton including 9 to 30 ring atoms.

9. The organic electroluminescence multicolor light-emitting apparatus according to claim 1, wherein p and q are 2.

10. The organic electroluminescence multicolor light-emitting apparatus according to claim 1, wherein at least one of $A^1$ and $A^2$ in the formula (1) or (2) is a group including a fused aromatic hydrocarbon skeleton including 10 to 30 ring carbon atoms or a group including an aromatic heterocyclic skeleton including 9 to 30 ring atoms.

11. The organic electroluminescence multicolor light-emitting apparatus according to claim 1, wherein $L^4$ in the formula (5) or (6) is a group including a fused aromatic hydrocarbon skeleton including 10 to 30 ring carbon atoms or a group including an aromatic heterocyclic skeleton including 9 to 30 ring atoms.

12. The organic electroluminescence multicolor light-emitting apparatus according to claim 10, wherein $Y^1$ and $Y^2$ are a single bond.

13. The organic electroluminescence multicolor light-emitting apparatus according to claim 1, wherein at least one of $A^1$ and $A^2$ as well as $R^1$ are a group selected from a naphthyl group, an anthracenyl group, a phenanthrenyl group, a naphthacenyl group, a benzophenanthrenyl group, a dibenzophenanthrenyl group, a chrysenyl group, a benzochrysenyl group, dibenzochrysenyl group, a fluoranthenyl group, a benzofluoranthenyl group, a triphenylenyl group, a benzotriphenylenyl group, a dibenzotriphenylenyl group, a picenyl group, a benzopicenyl group, a dibenzopicenyl group, a fluorenyl group, a 9,9-dimethylfluorenyl group, a 9,9-diphenylfluorenyl group and a 9,9-spirobifluorenyl group.

14. The organic electroluminescence multicolor light-emitting apparatus according to claim 1, wherein $L^4$ is a group selected from a q-valent residue of naphthalene, anthracene, phenanthrene, naphthacene, benzophenanthrene, dibenzophenanthrene, chrysene, benzochrysene, dibenzochrysene, fluoranthene, benzofluoranthene, triphenylene, benzotriphenylene, dibenzotriphenylene, picene, benzopicene, dibenzopicene, 9,9-diphenylfluorene and 9,9-spirobifluorene.

15. The organic electroluminescence multicolor light-emitting apparatus according to claim 1, wherein the second organic layer further comprises a hole-transporting material.

16. The organic electroluminescence multicolor light-emitting apparatus according to claim 1, wherein the second organic layer is formed of at least a layer comprising the compound represented by the formulas (1) to (6) and a layer comprising a hole-transporting material.

17. The organic electroluminescence multicolor light-emitting apparatus according to claim 15, wherein the hole-transporting material comprises an amine skeleton or a carbazole skeleton.

18. The organic electroluminescence multicolor light-emitting apparatus according to claim 1, wherein the second organic layer of the first light-emitting device and the second organic layer of the second light-emitting device comprise the same compound.

19. The organic electroluminescence multicolor light-emitting apparatus according to claim 1, wherein the film thickness of the second organic layer of the first light-emitting device and the film thickness of the second organic layer of the second light-emitting device are the same.

20. The organic electroluminescence multicolor light-emitting apparatus according to claim 1, wherein the first organic layer is a red, yellow or green phosphorescent emitting layer and the third organic layer is a blue fluorescent emitting layer.

21. The organic electroluminescence multicolor light-emitting apparatus according to claim 1, wherein the first organic layer is a layer formed by a coating method and the third organic layer is a layer formed by a deposition method.

22. The organic electroluminescence multicolor light-emitting apparatus according to claim 1, comprising a hole-injecting and transporting layer formed by a coating method on the anode side of the second organic layer of the second light-emitting device.

23. An organic electroluminescence multicolor light-emitting apparatus comprising:
- a substrate; and
- a first light-emitting device and a second light-emitting device being arranged in parallel on the surface of the substrate;
- wherein the first light-emitting device comprises, between an anode and a cathode, a first organic layer, a second organic layer and a third organic layer in this sequence from the anode side in a direction perpendicular to the surface of the substrate,
- the second light-emitting device comprises, between an anode and a cathode, a second organic layer and a third organic layer in this sequence from the anode side in a direction perpendicular to the surface of the substrate,
- the first organic layer comprises a first emitting dopant,
- the third organic layers comprise a second emitting dopant, and
- the second organic layers independently comprise any one of compounds represented by the following formulas (1) and (2):

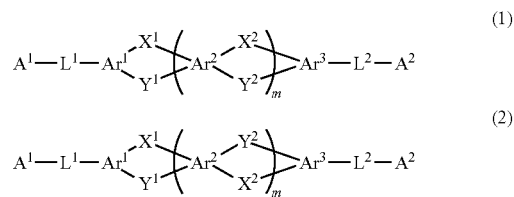

wherein $Ar^1$, $Ar^2$ and $Ar^3$ are independently a substituted or unsubstituted aromatic hydrocarbon group including 6 ring carbon atoms or a substituted or unsubstituted aromatic heterocyclic group including 6 ring atoms;

$X^1$ and $X^2$ are independently oxygen (O), sulfur (S), or $>N-R^1$, and $Y^1$ and $Y^2$ are a single bond;

$R^1$ is a dibenzofuranyl group or benzophenanthrenyl group;

m is 1;

$L^1$ and $L^2$ are independently a single bond, a substituted or unsubstituted alkylene group including 1 to 20 carbon atoms, a substituted or unsubstituted cycloalkylene group including 3 to 20 carbon atoms, a divalent silyl group or a divalent substituted silyl group including 3 to 20carbon atoms, a substituted or unsubstituted divalent aromatic hydrocarbon group including 6 to 30 ring carbon atoms or a substituted or unsubstituted divalent aromatic heterocyclic group including 5 to 30 ring atoms;

$A^1$ and $A^2$ are independently a hydrogen atom, a substituted or unsubstituted alkyl group including 1 to 20 carbon atoms, a substituted or unsubstituted cycloalkyl group including 3 to 20 carbon atoms, a substituted or unsubstituted alkoxy group including 1 to 20 carbon atoms, a substituted or unsubstituted aralkyl group including 7 to 24 carbon atoms, a silyl group or a substituted silyl group including 3 to 20 carbon atoms, a substituted or unsubstituted aromatic hydrocarbon group including 6 to 30 ring carbon atoms or a substituted or unsubstituted aromatic heterocyclic group including 5 to 30 ring atoms.

* * * * *

UNITED STATES PATENT AND TRADEMARK OFFICE
CERTIFICATE OF CORRECTION

PATENT NO. : 9,647,220 B2
APPLICATION NO. : 14/442652
DATED : May 9, 2017
INVENTOR(S) : Tadahiko Yoshinaga et al.

It is certified that error appears in the above-identified patent and that said Letters Patent is hereby corrected as shown below:

In the Claims

Column 146, Line 50:
Please replace formula (1):

" "

With the correct formula (1) as shown below:

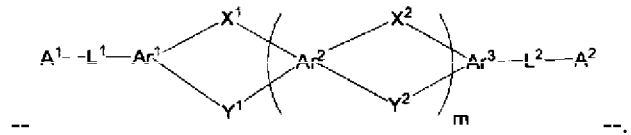
-- --.

Column 146, Line 55:
Please replace formula (2):

" "

With the correct formula (2) as shown below:

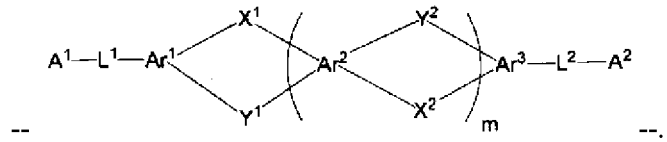
-- --.

Column 147, Line 62:
Please replace "$R^1$ to $R^{11}$ is a substituted or unsubstituted alkyl group" with --$R^1$ to $R^{11}$ are independently a substituted or unsubstituted alkyl group--.

Signed and Sealed this
Twenty-sixth Day of September, 2017

Joseph Matal
Performing the Functions and Duties of the
Under Secretary of Commerce for Intellectual Property and
Director of the United States Patent and Trademark Office